(12) United States Patent
Kirshenbaum et al.

(10) Patent No.: US 12,281,180 B2
(45) Date of Patent: Apr. 22, 2025

(54) PEPTOID-PEPTIDE MACROCYCLES, PHARMACEUTICAL COMPOSITIONS AND METHODS OF USING THE SAME

(71) Applicant: New York University, New York, NY (US)

(72) Inventors: Kent Kirshenbaum, New York, NY (US); Susan Logan, New York, NY (US); Timothy Craven, Seattle, WA (US); Amanda Kasper, New York, NY (US); Richard A. Bonneau, New York, NY (US); Jeffrey A Schneider, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 17/259,914

(22) PCT Filed: Jul. 12, 2019

(86) PCT No.: PCT/US2019/041674
§ 371 (c)(1),
(2) Date: Jan. 12, 2021

(87) PCT Pub. No.: WO2020/014652
PCT Pub. Date: Jan. 16, 2020

(65) Prior Publication Data
US 2021/0269482 A1 Sep. 2, 2021

Related U.S. Application Data

(60) Provisional application No. 62/796,460, filed on Jan. 24, 2019, provisional application No. 62/697,893, filed on Jul. 13, 2018.

(51) Int. Cl.
| | | |
|---|---|---|
| C07K 7/56 | (2006.01) | |
| A61P 35/00 | (2006.01) | |
| C07K 5/083 | (2006.01) | |
| A61K 38/00 | (2006.01) | |

(52) U.S. Cl.
CPC .............. *C07K 7/56* (2013.01); *A61P 35/00* (2018.01); *C07K 5/0806* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 5,525,590 A | * | 6/1996 | Bollinger | A61P 31/12 530/321 |
| 2007/0099917 A1 | * | 5/2007 | Nice | A61P 17/06 514/266.4 |
| 2013/0310375 A1 | | 11/2013 | Cheng et al. | |

FOREIGN PATENT DOCUMENTS

| | | |
|---|---|---|
| WO | 2014/145389 A1 | 9/2014 |
| WO | 2015/153560 A1 | 10/2015 |

OTHER PUBLICATIONS

Titlestad K ('Cleavage of linear tetrapeptides into two cyclic dipeptides' Chemical Communications 1971 v23 pp. 1527-1529) (Year: 1971).*
STN entry for Titlestad with RN 30270-82-7, 1972, 1 page (Year: 1972).*
Vollrath et al. ('Twice tied tight: enforcing conformational order in bicyclic peptoid oligomers' Chem Sci v3 2012 pp. 2726-2731) (Year: 2012).*
Vippagunta et al. ('Crystalline solids' Advanced Drug Delivery Reviews v48 2001 pp. 3-26) (Year: 2001).*
Registry No. 241148-10-7, entered STN Sep. 24, 1999, 1 page (Year: 1999).*
Registry No. 944251-03-0, entered STN Aug. 8, 2007, 2 pages (Year: 2007).*
Yelamanchi et al. ('A pathway map of glutamate metabolism' J Cell Commun Signal v10 2016 pp. 69-75) (Year: 2016).*
Thakkar, A., et al., High-Throughput Sequencing of Peptoids and Peptide-Peptoid Hybrids by Partial Edman Degradation and Mass Spectrometry, Journal of Combinatorial Chemistry, 2009, vol. 11, No. 2, pp. 1-18.
Rady, I., et al., Melittin, a major peptide component of bee venom, and its conjugates in cancer therapy, Cancer Letters, May 20, 2017, vol. 402, pp. 1-31.
Culf, A.S., et al., Solid-Phase Synthesis of N-Substituted Glycine Oligomers (alpha-peptoids) and Derivatives, Molecules, Aug. 4, 2010, vol. 15, pp. 5282-5335.
Webster, A.M., et al., Recent Advances in the Synthesis of Peptoid Macrocycles, Chemistry: A European Journal, Jan. 22, 2018, vol. 24, No. 30, pp. 7560-7573.
D'Amato, A., et al., Cyclic Peptides as Topological Templates: Synthesis via Central to Conformational Chirality Induction, Organic Letters, Jan. 17, 2018, vol. 20, No. 3, pp. 640-643.
D'Amato, A., et al., Conformational isomerism in cyclic peptoids and its specification, Organic Biomolecular Chemistry, Nov. 16, 2017, vol. 15, pp. 9932-9942.
Shin, S.B.Y., et al., Cyclic Peptoids, J. Am. Chem. Soc., Feb. 27, 2007, vol. 129, No. 11, pp. 3218-3225.

\* cited by examiner

*Primary Examiner* — Ronald T Niebauer
(74) *Attorney, Agent, or Firm* — Hodgson Russ LLP

(57) ABSTRACT

Provided are peptoid-peptide macrocycles. The peptoid-peptide macrocycles may have inhibitory activity towards the Wnt signaling pathway. The Wnt signaling pathway is associated with cancer and other diseases and conditions. Such diseases include, for example, pulmonary fibrosis. Also described are methods of making the peptoid-peptide macrocycles, compositions containing the peptoid-peptide macrocycles, and methods of using the peptoid-peptide macrocycles.

9 Claims, 19 Drawing Sheets
Specification includes a Sequence Listing.

Figure 14

PEPTOID-PEPTIDE MACROCYCLES, PHARMACEUTICAL COMPOSITIONS AND METHODS OF USING THE SAME

CROSS REFERENCE TO RELATED APPLICATIONS

This applications claims priority to U.S. Provisional Application No. 62/697,893, filed on Jul. 13, 2018, and U.S. Provisional Application No. 62/796,460, filed on Jan. 24, 2019, the disclosures of which are herein incorporated by reference.

STATEMENT REGARDING FEDERALLY SPONSORED RESEARCH OR DEVELOPMENT

This invention was made with government support under grant no. 1152317 awarded by the National Science Foundation. The government has certain rights in the invention.

SEQUENCE LISTING

The instant application contains a Sequence Listing, which has been submitted electronically in txt format and is hereby incorporated by reference in its entirety. The .txt copy, created on Aug. 16, 2022, is named "058636_00317_Seq_ID_ST25.txt" and is 4,340 bytes.

BACKGROUND OF THE DISCLOSURE

Despite an extensive effort to develop inhibitors of protein-protein interactions (PPIs), there has been little success translating such compounds to the clinic. Interactions between proteins frequently play key roles in the biochemical pathways that drive disease states. Unfortunately, these proteins are often not amenable to drug targeting using typical small molecules as therapeutic candidates. Peptides are peptidomimetic oligomers that have demonstrated a range of biological activities and have the potential to inhibit PPIs by mimicking protein secondary structure motifs.

Protein-protein interactions (PPIs) provide the structural and functional basis for many critical biological processes. Extensive efforts have been made to identify small molecules or peptides capable of inhibiting particular PPIs that play a role in the pathogenesis of disease. Despite these important advances, additional design strategies are urgently needed. Small molecules may lack sufficient surface area to abrogate protein-protein binding effectively, as these interfaces are typically broad and flat. In addition, peptides often lack desirable pharmacological characteristics and are readily susceptible to degradation in vivo. These shortcomings can potentially be addressed by development of peptidomimetic oligomers that exhibit steric and chemical complementarity with protein surfaces. Such molecules may populate an attractive "middle ground" between small molecules and biomacromolecular therapeutics. Crafting peptidomimetics suitable for targeting PPIs is a formidable and intriguing challenge, however, as potent and specific binding likely necessitates identifying conformationally ordered oligomers capable of presenting diverse functional groups in a predictable orientation.

'Foldamers' are sequence-specific oligomers that can mimic a range of secondary structure motifs that are ubiquitous in proteins and oligonucleotides. One particularly promising class of foldamers are termed "peptoids", which are composed of sequences of N-substituted glycine monomer units. Although peptoids are oligo-amides, like native peptides, the side chains project from the backbone amide nitrogens instead of the α-carbon. This backbone modification confers peptoids with a broad resistance to proteolytic cleavage. Peptoid synthesis efficiently employs the use of myriad primary amines as "submonomer" reagents, leading to rapid solid-phase generation of oligomers that exhibit extraordinary chemical diversity and tunable physicochemical properties. These synthetic and structural features endow peptoids with the capability to satisfy the physicochemical requirements for a variety of biomedical applications. Peptoid sequences comprised of bulky chiral side chains have the capacity to adopt a stable helical secondary structure, although some conformational heterogeneity is evident in solution. The crystal structure of one linear peptoid homopentamer composed of bulky chiral side chains exhibited a helical conformation resembling that of a polyproline type I helix. Oligopeptide sequences incorporating repeating units of two bulky chiral side chains and a cationic side chain can form facially amphiphilic helical structures. Recent studies describe antimicrobial activities generated from facially amphiphilic helical peptoids. These peptoid oligomers are reported to be good functional mimics of maganin-2 amide, a peptide antimicrobial agent from *Xenopus* skin.

The preponderance of synthetic drug molecules discovered to date have been small molecules that typically bind to discrete binding pockets on individual proteins. Advances in molecular pharmacology will greatly benefit from the ability to bind to protein surfaces in a manner that would inhibit protein-protein interactions. This will require the design of new drug molecules that can bind the flat, extended surface areas that are characteristic of protein-protein binding interfaces. Small molecules are generally incapable of establishing sufficient binding strength to enable binding to these extended surfaces.

It is therefore important to identify synthetic oligomers, such as peptidomimetics, that can recapitulate the binding modes of structural motifs presented at protein interfaces. Unconstrained polypeptide segments themselves are poor candidates, as they are typically conformationally labile and susceptible to proteolytic degradation. In addition, peptides can exhibit poor cell-uptake characteristics.

Macrocyclic oligomers can address many of these challenges, and constitute a promising class of molecules for drug discovery. The presence of the macrocyclic constraint can enforce conformational ordering and enhance binding energies. For some classes of oligomeric molecules, the folding properties may be sufficiently well understood to allow for the predictable design of particular monomer sequences that will be pre-organized to establish favorable building interactions with a specified protein target. Oligomers of N-substituted glycine, known as "peptoids," are a family of peptidomimetic oligomers with the capacity to self-assemble into ordered secondary structures. A variety of bioactivities have been described for peptoids, and they constitute one of the most promising classes of "foldamer" molecules. The conformational properties of peptoids have been extensively evaluated and they are highly amenable to structure prediction and computational design. A number of high-resolution structures have been obtained for various peptoid sequences, varying from dimers to 16mer molecules. Notably, many of the solved structures have been of macrocyclic peptoids, indicative of the importance of the covalent constraint to establish conformational ordering. In addition, peptoids and peptide-peptoid hybrids have been observed to display improved cell permeability properties in comparison to the corresponding peptide oligomer analogs.

Prostate cancer is the most common form of male cancer and the third most common cause of male cancer-related death. While patients with localized disease have a positive prognosis, those with metastatic disease have a five year survival of 30%. The main therapeutic target in prostate cancer is the androgen receptor (AR). Unfortunately, most patients treated with anti-androgens will develop resistance and continued disease progression, a state known as metastatic castration resistant prostate cancer (mCRPC). Second generation anti-androgens, including Enzalutamide and Abiraterone, have been developed but extend life expectancy on average less than 6 months, as resistance can continue to develop. There are multiple mechanisms of resistance, such as gene amplification or alternative splicing of the androgen receptor (AR). Additionally, activation of auxiliary pathways can be oncogenic and/or upregulate AR signaling. For instance, the AR gene is under transcriptional control of the Wnt signaling pathway. The central Wnt regulator, β-catenin, can also interact with AR and act as a co-activator.

The Wnt/wingless (wg) proteins are a family of conserved signaling molecules that have been shown to regulate a plethora of fundamental developmental and cell biological processes, including cell proliferation, differentiation and cell polarity. Mutations in the Wnt genes or in those genes encoding regulators of the Wnt/wg signaling pathway can cause devastating birth defects, including debilitating abnormalities of the central nervous system, axial skeleton, limbs, and occasionally other organs. Aberrant Wnt signaling has also been linked to human diseases, such as, for example, hepatic, colorectal, breast and skin cancers.

Recent genome-wide sequencing studies found the Wnt signaling pathway to be mutated in upwards of 20% of tumors from patients with mCRPC, making it one of the most mutated pathways after the AR itself along with the tumor suppressors P53 and PTEN. The most common Wnt mutations found were in adenomatous polyposis coli (APC) or the phosphorylation domain of β-catenin, both of which cause the constitutive stabilization of β-catenin. Following its stabilization, β-catenin translocates to the nucleus where it binds the T-cell factor (TCF) family of transcription factors. This causes a conformational change in TCF that activates transcription of a set of genes involved in cell proliferation and differentiation. β-catenin contains three domains, an unstructured N-terminal regulatory domain, an unstructured C-terminal transactivation domain, and an alpha-helical armadillo domain that encompasses the majority of the protein. β-catenin interacts with most of its binding partners including TCF, APC, Axin, E-cadherin, and the AR through the armadillo domain. While the protein contacts partially overlap, there are distinct differences that can potentially enable specific inhibition of one PPI without affecting the others. A co-crystal structure of β-catenin and TCF shows there is a unique β-hairpin loop motif in TCF that binds to a cleft in the β-catenin armadillo domain.

The Wnt signaling pathway is dysregulated in several cancer subtypes, including, for example: colorectal cancer and melanoma. β-catenin:TCF protein-protein interactions are distal components of the Wnt signaling pathway. Upon binding, β-catenin:TCF complexes turn on transcription of several anti-apoptotic and anti-cell-cycle arrest proteins, thereby driving cancer formation. Components of the Wnt signaling pathway, specifically the interaction of β-catenin and the Androgen Receptor (AR), are also dysregulated in prostate cancer. Targeting these interactions is of great interest to the scientific community, but the lack of a well-defined TCF binding mode/pocket on the surface of β-catenin has prevented much success in this endeavor.

In view of the foregoing, an ongoing and unmet need exists for therapeutic agents, and corresponding pharmaceutical compositions and related methods of treatment that address conditions causally related to protein-protein interactions, such as aberrant Wnt pathway activity and CRT activity.

SUMMARY OF THE DISCLOSURE

Disclosed herein are peptoid-containing macrocycles (e.g., peptoid-peptide macrocycles) that, in various examples, address outstanding challenges in molecular pharmacology, including targets that are currently considered "undruggable." The peptoid-peptide macrocycles may be referred to as "compounds" or "macrocycles."

The macrocycles of the present disclosure comprise substituted hybrid peptoid-peptide macrocycles. The macrocycles may have inhibitory activity towards the Wnt signaling pathway. Accordingly, the peptoid-peptide macrocycles of the disclosure may have anticancer activity.

In one aspect, the present disclosure relates to macrocycles where at least one of the peptoid monomers is replaced with an amino acid. In a particular embodiment thereof, the amino acid is a D-isomer of the amino acid. The resulting macrocycles are referred to as peptoid-peptide macrocycles.

More particularly, the present disclosure relates to peptoid-peptide macrocycles, according to formula A:

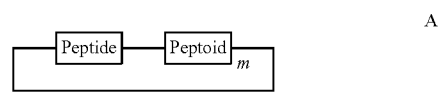

where "Peptide" is a single amino acid residue, "Peptoid" is N-substituted amino acid residue, and m is an integer from 2-20; or a pharmaceutically acceptable salt, solvate or prodrug thereof; and stereoisomers, isotopic variants and tautomers thereof.

In an aspect, the disclosure provides a pharmaceutical composition comprising a pharmaceutically acceptable carrier and a pharmaceutically effective amount of the peptoid-peptide macrocycles of the disclosure.

In yet another method of treatment aspect, this disclosure provides a method of treating a mammal susceptible to or afflicted with a condition that gives rise to increased cellular proliferation or a transformed phenotype, or that relates to dysregulation of Wnt/wg signaling. The present macrocycles may be used as anti-proliferative agents that reduce proliferative levels (potentially to normal levels for a particular cell type), and/or anti-transformed phenotype agents that restore, at least in part, normal phenotypic properties of a particular cell type. Accordingly, the present macrocycles have use for the treatment of cancers and hyperproliferative disorders relating to aberrant Wnt/wg signaling.

BRIEF DESCRIPTION OF THE DRAWINGS

For a fuller understanding of the nature and objects of the disclosure, reference should be made to the following detailed description taken in conjunction with the accompanying figures.

Figure 14:
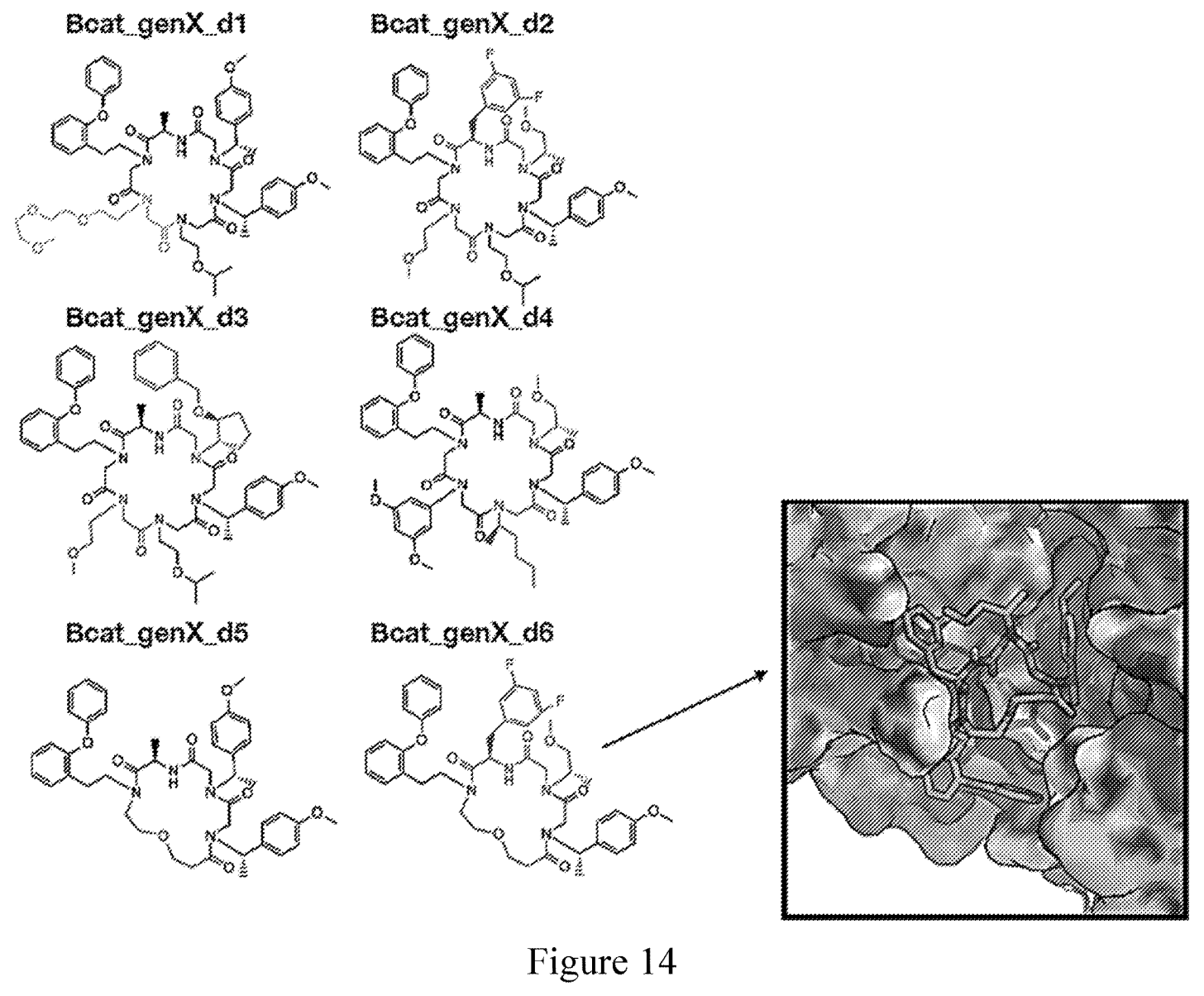

FIG. 14 shows covalent B-catenin binder design.

DETAILED DESCRIPTION OF THE DISCLOSURE

Figure 1:
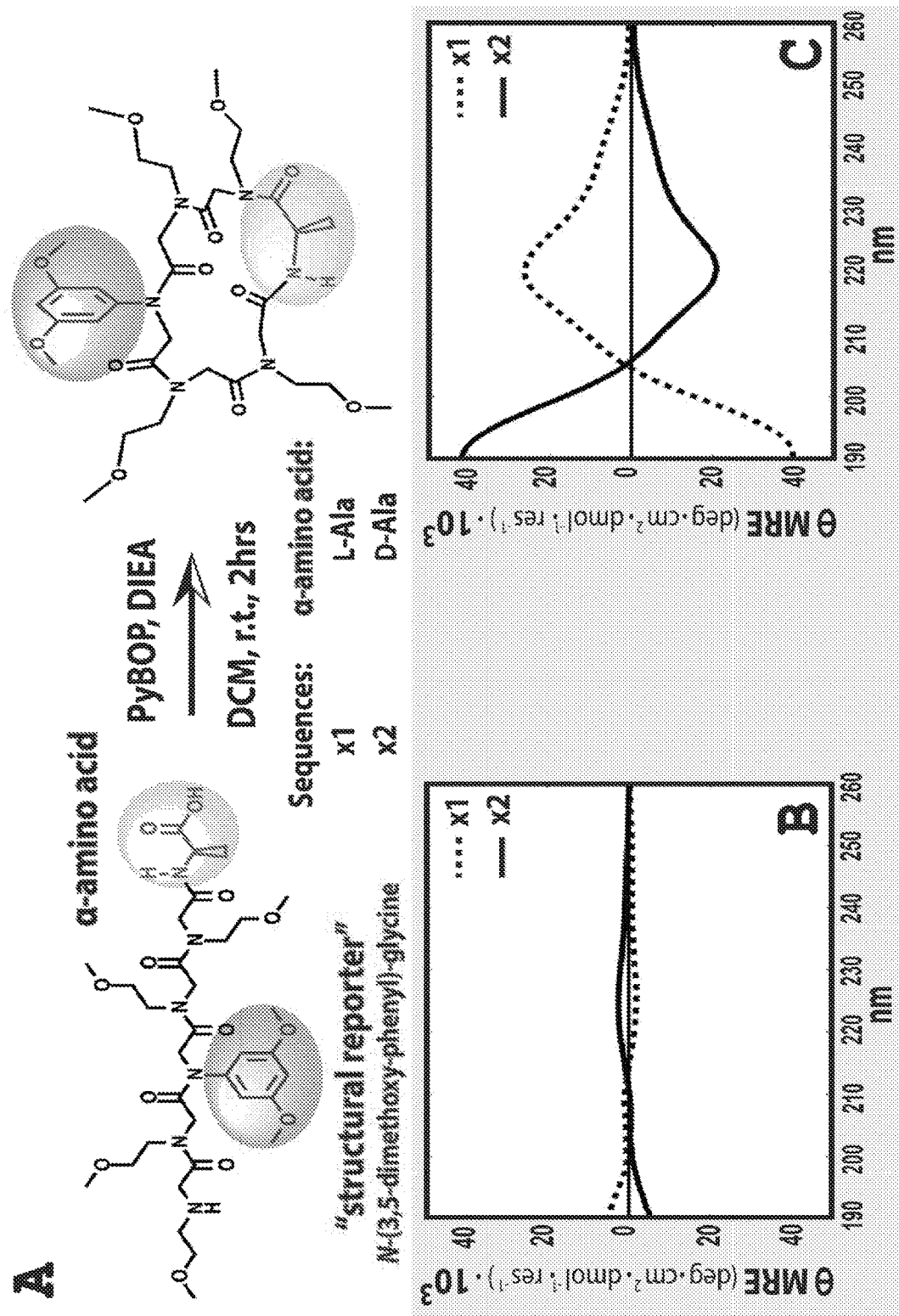
FIG. 1 shows monitoring structure before and after head-to-tail macrocyclization. (A) Cyclization scheme starting with a linear peptoid-peptide hybrid sequence (left panel) and proceeding through macrocylization utilizing PyBOP and DIEA. (B) Far-UV CD spectrum of linear compounds (100 mM, 1 mm path length, ACN). (C) Far-UV CD spectrum of cyclic compounds (100 mM, 1 mm path length, ACN).

Although claimed subject matter will be described in terms of certain embodiments/examples, other embodiments/examples, including embodiments/examples that do not provide all of the benefits and features set forth herein, are also within the scope of this disclosure. Various structural, logical, and process step may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range. As an illustrative example, any range provided herein includes all values that fall within the ranges to the tenth decimal place, unless indicated otherwise.

Disclosed herein are peptoid-containing macrocycles (e.g., peptoid-peptide macrocycles) that, in various examples, address outstanding challenges in molecular pharmacology, including targets that are currently considered "undruggable." The peptoid-peptide macrocycles may be referred to as "compounds" or "macrocycles."

Utilizing a biomimetic strategy in molecular pharmacology, presented is a demonstration on how computational tools can be used to model the structure of synthetic peptide mimics, enabling the design of folded molecules that inhibit protein-protein interactions. Interactions between the proteins β-catenin and TCF, an important step in the Wnt signaling pathway that is associated with several cancer types, were targeted. This effort resulted in the successful design of a peptoid-peptide hybrid macrocycle complimentary to the β-catenin surface which inhibits Wnt signaling and successfully blocks growth of prostate cancer cells.

Disclosed herein is the in silico design of a macrocycle primarily composed of peptoid residues that targets Wnt signaling via inhibition of the interaction between β-catenin and the T-Cell Factor (TCF) family of transcription factors. The β-catenin:TCF PPI plays a critical role in the Wnt signaling pathway downstream of mutations that are found to constitutively activate the pathway in multiple cancers, including prostate cancer.

Definitions

The following terms are intended to have the meanings presented therewith below and are useful in understanding the description and intended scope of the present disclosure.

When describing subject matter the present disclosure, which may include compounds, pharmaceutical compositions containing such compounds and methods of using such compounds and compositions, the following terms, if present, have the following meanings unless otherwise indicated. It should also be understood that when described herein any of the groups/moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

As used herein, unless otherwise stated, the term "group" refers to a chemical entity that has one terminus that can be covalently bonded to other chemical species. Examples of groups include, but are not limited to:

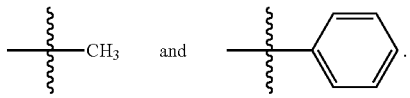

As used herein, unless otherwise stated, the term "moiety" refers to a chemical entity that has two or more termini that can be covalently bonded to other chemical species. Examples of moieties include, but are not limited to:

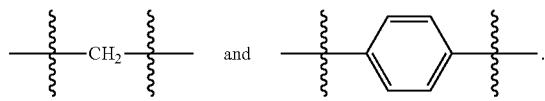

"Acyl" or "Alkanoyl" refers to a radical-$C(O)R^{20}$, where $R^{20}$ is hydrogen, $C_1$-$C_8$ alkyl ($C_1$, $C_2$, $C_3$, $C_4$, $C_5$, $C_6$, $C_7$, or $C_8$), $C_3$-$C_{10}$ cycloalkyl ($C_3$, $C_4$, $C_5$, $C_6$, $C_7$, $C_8$, $C_9$, or $C_{10}$), $C_3$-$C_{10}$ cycloalkylmethyl ($C_3$, $C_4$, $C_5$, $C_6$, $C_7$, $C_8$, $C_9$, or $C_{10}$), 4-10 membered heterocycloalkyl (4, 5, 6, 7, 8, 9, or 10), aryl, arylalkyl, 5-10 membered heteroaryl or heteroarylalkyl (5, 6, 7, 8, 9, or 10) as defined herein. Representative examples include, but are not limited to, formyl, acetyl, cyclohexylcarbonyl, cyclohexylmethylcarbonyl, benzoyl and benzylcarbonyl. Exemplary 'acyl' groups/moieties include, but are not limited to, —C(O)H, —C(O)—$C_1$-$C_8$ alkyl, —C(O)—$(CH_2)_t(C_6$-$C_{10}$ aryl), —C(O)—$(CH_2)_t$(5-10 membered heteroaryl), —C(O)—$(CH_2)_t(C_3$-$C_{10}$ cycloalkyl), and —C(O)—$(CH_2)_t$(4-10 membered heterocycloalkyl), wherein t is an integer from 0 to 4 (0, 1, 2, 3, or 4).

"Substituted Acyl" or "Substituted Alkanoyl" refers to a radical-$C(O)R^{21}$, wherein $R^{21}$ is independently $C_1$-$C_8$ alkyl ($C_1$, $C_2$, $C_3$, $C_4$, $C_5$, $C_6$, $C_7$, or $C_8$), substituted with halo or hydroxy; or $C_3$-$C_{10}$ cycloalkyl ($C_3$, $C_4$, $C_5$, $C_6$, $C_7$, $C_8$, $C_9$, or $C_{10}$), 4-10 membered heterocycloalkyl (4, 5, 6, 7, 8, 9, or 10), $C_6$-$C_{10}$ aryl ($C_6$, $C_7$, $C_8$, $C_9$, or $C_{10}$), arylalkyl, 5-10 membered heteroaryl or heteroarylalkyl (5, 6, 7, 8, 9, or 10), each of which is substituted with unsubstituted $C_1$-$C_4$ alkyl ($C_1$, $C_2$, $C_3$, or $C_4$), halo, unsubstituted $C_1$-$C_4$ alkoxy ($C_1$, $C_2$, $C_3$, or $C_4$), unsubstituted $C_1$-$C_4$ haloalkyl ($C_1$, $C_2$, $C_3$, or $C_4$), unsubstituted $C_1$-$C_4$ hydroxyalkyl ($C_1$, $C_2$, $C_3$, or $C_4$), or unsubstituted $C_1$-$C_4$ haloalkoxy or hydroxy ($C_1$, $C_2$, $C_3$, or $C_4$).

"Alkoxy" refers to the group-$OR^{29}$ where $R^{29}$ is $C_1$-$C_8$ alkyl. Non-limiting examples of alkoxy groups are methoxy, ethoxy, n-propoxy, isopropoxy, n-butoxy, tert-butoxy, sec-butoxy, n-pentoxy, n-hexoxy, 1,2-dimethylbutoxy, and the like. In an example, alkoxy groups are lower alkoxy, i.e., with 1 and 6 carbon atoms (1, 2, 3, 4, 5, or 6). In another example, alkoxy groups have 1 to 4 carbon atoms (1, 2, 3, or 4).

"Substituted alkoxy" refers to an alkoxy group substituted with one or more of those groups recited in the definition of "substituted" herein, and particularly refers to an alkoxy group having 1 or more substituents, for instance from 1 to 5 substituents (1, 2, 3, 4, or 5), and particularly from 1 to 3 substituents (1, 2, or 3), in particular 1 substituent, chosen from amino, substituted amino, $C_6$-$C_{10}$ aryl ($C_6$, $C_7$, $C_8$, $C_9$, or $C_{10}$), aryloxy, carboxyl, cyano, $C_3$-$C_{10}$ cycloalkyl ($C_3$, $C_4$, $C_5$, $C_6$, $C_7$, $C_8$, $C_9$, or $C_{10}$), 4-10 membered heterocycloalkyl (4, 5, 6, 7, 8, 9, or 10), halogen, 5-10 membered heteroaryl (5, 6, 7, 8, 9, or 10), hydroxyl, nitro, thioalkoxy, thioaryloxy, thiol, alkyl-S(O)—, aryl-S(O)—, alkyl-$S(O)_2$— and aryl-S$(O)_2$—, and the like. In an example, "substituted alkoxy" groups are-O—$(CH_2)_t(C_6$-$C_{10}$ aryl), —O—$(CH_2)_t$(5-10 membered heteroaryl), —O—$(CH_2)_t(C_3$-$C_{10}$ cycloalkyl), and —O—$(CH_2)_t$(4-10 membered heterocycloalkyl), wherein t is an integer from 0 to 4 (0, 1, 2, 3, or 4) and any aryl, heteroaryl, cycloalkyl or heterocycloalkyl groups present, may themselves be substituted by unsubstituted $C_1$-$C_4$ alkyl ($C_1$, $C_2$, $C_3$, or $C_4$), halo, unsubstituted $C_1$-$C_4$ alkoxy ($C_1$, $C_2$, $C_3$, or $C_4$), unsubstituted $C_1$-$C_4$ haloalky ($C_1$, $C_2$, $C_3$, or $C_4$)l, unsubstituted $C_1$-$C_4$ hydroxyalkyl ($C_1$, $C_2$, $C_3$, or $C_4$), or unsubstituted $C_1$-$C_4$ haloalkoxy or hydroxy ($C_1$, $C_2$, $C_3$, or $C_4$). In another example, "substituted alkoxy" groups are $OCF_3$, $OCH_2CF_3$, $OCH_2Ph$, $OCH_2$-cyclopropyl, $OCH_2CH_2OH$, and $OCH_2CH_2NMe_2$.

"Alkyl" means straight or branched hydrocarbon having 1 to 20 carbon atoms, (1, 2, 3, 4, 5, 6, 7, 8, 9, 10, 11, 12, 13, 14, 15, 16, 17, 18, 19, or 20). In an example, an alkyl group/moiety has 1 to 12 carbon atoms (1, 2, 3, 4, 5, 6, 7, 8, 9, 10, 11, or 12). In another example, an alkyl group/ moiety is a lower alkyl group/moiety that has 1 to 6 carbon atoms (1, 2, 3, 4, 5, or 6). In another example, an alkyl group/moiety has 1 to 4 carbon atoms (1, 2 3, or 4). Examples of straight chained groups include, but are not limited to, methyl, ethyl, n-propyl, and n-butyl. Branched means that one or more lower alkyl groups such as methyl, ethyl, propyl or butyl is attached to a linear alkyl group/ moiety, exemplary branched groups include isopropyl, iso-butyl, t-butyl and isoamyl.

"Substituted alkyl" refers to an alkyl group/moiety as defined above substituted with one or more of those groups recited in the definition of "substituted" herein, and, in non-limiting examples, refers to an alkyl group having 1 or more substituents, for instance from 1 to 5 substituents, and particularly from 1 to 3 substituents (1, 2, or 3), in particular 1 substituent, chosen from acyl, acylamino, acyloxy (—O-acyl or —OC(O)$R^{20}$), alkoxy, alkoxycarbonyl, alkoxycarbonylamino (—NR"-alkoxycarbonyl or —NH—C(O)—O$R^{27}$), amino, substituted amino, aminocarbonyl (carbamoyl or amido or —C(O)—NR"$_2$), aminocarbonylamino (—NR"—C(O)—NR"$_2$), aminocarbonyloxy (—O—C(O)—NR"$_2$), aminosulfonyl, sulfonylamino, aryl, aryloxy, azido, carboxyl, cyano, cycloalkyl, halogen, hydroxy, heteroaryl, nitro, thiol, —S-alkyl, —S-aryl, —S(O)-alkyl, —S(O)-aryl, —S(O)$_2$-alkyl, and —S(O)$_2$-aryl. In an example, "substituted alkyl" refers to a $C_1$-$C_8$ ($C_1$, $C_2$, $C_3$, $C_4$, $C_5$, $C_6$, $C_7$, or $C_8$) alkyl group substituted with halo, cyano, nitro, trifluoromethyl, trifluoromethoxy, azido, —NR"'SO$_2$R", —SO$_2$NR"R", —C(O)R", —C(O)OR", —OC(O)R",-NR"'C(O)R", —C(O)NR"R", —NR"R", or —(CR"R"")$_m$OR"; wherein each R" is independently chosen from H, $C_1$-$C_8$ alkyl ($C_1$, $C_2$, $C_3$, $C_4$, $C_5$, $C_6$, $C_7$, or $C_8$), —(CH$_2$)$_t$($C_6$-$C_{10}$ aryl) ($C_6$, $C_7$, $C_8$, $C_9$, or $C_{10}$), —(CH$_2$)$_t$(5-10 membered heteroaryl) ($C_5$, $C_6$, $C_7$, $C_8$, $C_9$, or $C_{10}$), —(CH$_2$)$_t$($C_3$-$C_{10}$ cycloalkyl) ($C_3$, $C_4$, $C_5$, $C_6$, $C_7$, $C_8$, $C_9$, or $C_{10}$), and —(CH$_2$)$_t$(4-10 membered heterocycloalkyl) (4, 5, 6, 7, 8, 9, or 10), wherein t is an integer from 0 to 4 (0, 1, 2, 3, or 4) and any aryl, heteroaryl, cycloalkyl or heterocycloalkyl groups present, may themselves be substituted by unsubstituted $C_1$-$C_4$ alkyl ($C_1$, $C_2$, $C_3$, or $C_4$), halo ($C_1$, $C_2$, $C_3$, or $C_4$), unsubstituted $C_1$-$C_4$ alkoxy ($C_1$, $C_2$, $C_3$, or $C_4$), unsubstituted $C_1$-$C_4$ haloalkyl ($C_1$, $C_2$, $C_3$, or $C_4$), unsubstituted $C_1$-$C_4$ hydroxyalkyl ($C_1$, $C_2$, $C_3$, or $C_4$), or unsubstituted $C_1$-$C_4$ haloalkoxy or hydroxy ($C_1$, $C_2$, $C_3$, or $C_4$). Each of R'" and R"" independently represents H or $C_1$-$C_8$ alkyl ($C_1$, $C_2$, $C_3$, $C_4$, $C_5$, $C_6$, $C_7$, or $C_8$).

"Aralkyl" or "arylalkyl" refers to an alkyl group/moiety, as defined above, substituted with one or more aryl groups/ moieties, as defined above. Particular aralkyl or arylalkyl groups are alkyl groups substituted with one aryl group.

"Substituted aralkyl" or "substituted arylalkyl" refers to an alkyl group/moiety, as defined above, substituted with one or more aryl groups/moieties; and at least one of the aryl groups/moieties present, may themselves be substituted by unsubstituted $C_1$-$C_4$ alkyl ($C_1$, $C_2$, $C_3$, or $C_4$), halo, cyano, unsubstituted $C_1$-$C_4$ alkoxy ($C_1$, $C_2$, $C_3$, or $C_4$), unsubstituted $C_1$-$C_4$ haloalkyl ($C_1$, $C_2$, $C_3$, or $C_4$), unsubstituted $C_1$-$C_4$ hydroxyalkyl ($C_1$, $C_2$, $C_3$, or $C_4$), or unsubstituted $C_1$-$C_4$ haloalkoxy or hydroxy ($C_1$, $C_2$, $C_3$, or $C_4$).

"Aryl" refers to a monovalent aromatic hydrocarbon group/moiety derived by the removal of one hydrogen atom from a single carbon atom of a parent aromatic ring system. In particular aryl, refers to an aromatic ring structure, mono-cyclic or poly-cyclic that includes from 5 to 12 ring members (5, 6, 7, 8, 9, 10, 11, or 12), or, more particularly, 5 to 10 members (5, 6, 7, 8, 9, or 10). For example, where the aryl group/moiety is a monocyclic ring system it preferentially contains 6 carbon atoms. Typical aryl groups/ moieties include, but are not limited to, groups/moieties derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene and trinaphthalene. For example, aryl groups include phenyl, naphthyl, indenyl, and tetrahydronaphthyl.

"Substituted aryl" refers to an aryl group/moiety substituted with one or more of those groups recited in the definition of 'substituted' herein, and particularly refers to an aryl group/moiety that may optionally be substituted with 1 or more substituents, for instance from 1 to 5 substituents (1, 2, 3, 4, or 5), particularly 1 to 3 substituents (1, 2, or 3), in particular 1 substituent. In an example, "substituted aryl" refers to an aryl group substituted with one or more of groups selected from halo, $C_1$-$C_8$ alkyl ($C_1$, $C_2$, $C_3$, $C_4$, $C_5$, $C_6$, $C_7$, or $C_8$), $C_1$-$C_8$ haloalkyl ($C_1$, $C_2$, $C_3$, $C_4$, $C_5$, $C_6$, $C_7$, or $C_8$), cyano, hydroxy, $C_1$-$C_8$ alkoxy ($C_1$, $C_2$, $C_3$, $C_4$, $C_5$, $C_6$, $C_7$, or $C_8$), amino, and the like. Non-limiting examples of representative substituted aryls include the following:

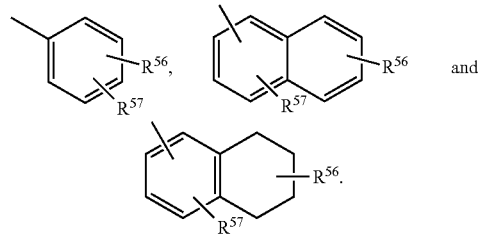

In these formulae, one of $R^{56}$ and $R^{57}$ may be hydrogen and at least one of $R^{56}$ and $R^{57}$ is each independently chosen from $C_1$-$C_8$ alkyl ($C_1$, $C_2$, $C_3$, $C_4$, $C_5$, $C_6$, $C_7$, or $C_8$), $C_1$-$C_8$ haloalkyl ($C_1$, $C_2$, $C_3$, $C_4$, $C_5$, $C_6$, $C_7$, or $C_8$), 4-10 membered heterocycloalkyl (4, 5, 6, 7, 8, 9, or 10), alkanoyl, $C_1$-$C_8$ alkoxy ($C_1$, $C_2$, $C_3$, $C_4$, $C_5$, $C_6$, $C_7$, or $C_8$), heteroaryloxy, alkylamino, arylamino, heteroarylamino, NR$^{58}$COR$^{59}$, NR$^{58}$SOR$^{59}$NR$^{58}$SO$_2$R$^{59}$, COOalkyl, COOaryl, CONR$^{58}$R$^{59}$, CONR$^{58}$OR$^{59}$, NR$^{58}$R$^{59}$, SO$_2$NR$^{58}$R$^{59}$, S-alkyl, SOalkyl, SO$_2$alkyl, Saryl, SOaryl, SO$_2$aryl, or $R^{56}$ and $R^{57}$ may be joined to form a cyclic ring (saturated or unsaturated) from 5 to 8 atoms (5, 6, 7, or 8), optionally containing one or more heteroatoms selected from the group N, O or S. $R^{60}$ and $R^{61}$ are independently hydrogen, $C_1$-$C_8$ alkyl ($C_1$, $C_2$, $C_3$, $C_4$, $C_5$, $C_6$, $C_7$, or $C_8$), $C_1$-$C_4$ haloalkyl ($C_1$, $C_2$, $C_3$, or $C_4$), $C_3$-$C_{10}$ cycloalkyl ($C_3$, $C_4$, $C_5$, $C_6$, $C_7$, $C_8$, $C_9$, or $C_{10}$), 4-10 membered heterocycloalkyl (4, 5, 6, 7, 8, 9, or 10), $C_6$-$C_{10}$ aryl ($C_6$, $C_7$, $C_8$, $C_9$, or $C_{10}$), substituted aryl, 5-10 membered heteroaryl (5, 6, 7, 8, 9, or 10).

"Heteroaryl" refers to an aromatic monocycle or polycycle that includes one or more heteroatoms and 5 to 12 ring members (5, 6, 7, 8, 9, 10, 11, or 12), or, more particularly, 5 to 10 ring members (5, 6, 7, 8, 9, or 10). The heteroaryl group/moiety can be, for example, but not limited to, a five membered or six membered monocyclic ring or a bicyclic structure formed from fused five and six membered rings or two fused six membered rings or two fused five membered rings. Each ring may contain up to four heteroatoms typically selected from nitrogen, sulfur and oxygen. In an example, the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups/moieties include, but are not limited to, pyrrole, furan, thiophene, imidazole, furazan, oxazole, oxadiazole, oxatriazole, isoxazole, thiazole, isothiazole, pyrazole, triazole and tetrazole groups. Examples of six membered monocyclic heteroaryl groups/moieties include, but are not limited to, pyridine, pyrazine, pyridazine, pyrimidine and triazine. Particular examples of bicyclic heteroaryl groups containing a five membered ring fused to another five membered ring include but are not limited to imidazothiazole and imidazoimidazole. Examples of bicyclic heteroaryl groups/moieties containing a six membered ring fused to a five membered ring include, but are not limited to, benzofuran, benzothiophene, benzimidazole, benzoxazole, isobenzoxazole, benzisoxazole, benzthiazole, benzisothiazole, isobenzofuran, indole, isoindole, isoindolone, indolizine, indoline, isoindoline, purine (e.g., adenine, guanine), indazole, pyrazolopyrimidine, triazolopyrimidine, benzodioxole and pyrazolopyridine groups. Particular examples of bicyclic heteroaryl groups/moieties containing two fused six membered rings include, but are not limited to, quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups/moieties are those derived from thiophene, pyrrole, benzothiophene, benzofuran, indole, pyridine, quinoline, imidazole, oxazole and pyrazine. Examples of representative heteroaryls include, but are not limited to, the following:

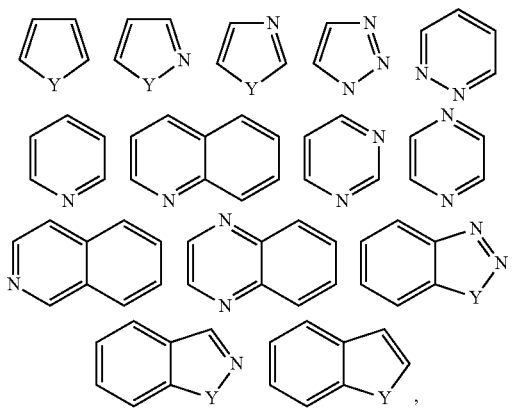

where each Y is selected from carbonyl, N, $NR^{65}$, O and S; and $R^{65}$ is independently hydrogen, $C_1$-$C_8$ alkyl ($C_1$, $C_2$, $C_3$, $C_4$, $C_5$, $C_6$, $C_7$, or $C_8$), $C_3$-$C_{10}$ cycloalkyl ($C_3$, $C_4$, $C_5$, $C_6$, $C_7$, $C_8$, $C_9$, or $C_{10}$), 4-10 membered heterocycloalkyl (4, 5, 6, 7, 8, 9, or 10), $C_6$-$C_{10}$ aryl ($C_6$, $C_7$, $C_8$, $C_9$, or $C_{10}$), and 5-10 membered heteroaryl (5, 6, 7, 8, 9, or 10).

Examples of representative aryl having hetero atoms containing substitution include, but are not limited to, the following:

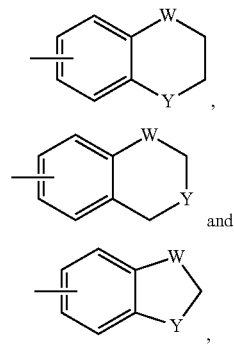

where each W is selected from $C(R^{66})_2$, $NR^{66}$, O and S; and each Y is selected from carbonyl, $NR^{66}$, O and S; and $R^{66}$ is independently hydrogen, $C_1$-$C_8$ alkyl ($C_1$, $C_2$, $C_3$, $C_4$, $C_5$, $C_6$, $C_7$, or $C_8$), $C_3$-$C_{10}$ cycloalkyl ($C_3$, $C_4$, $C_5$, $C_6$, $C_7$, $C_8$, $C_9$, or $C_{10}$), 4-10 membered heterocycloalkyl (4, 5, 6, 7, 8, 9, or 10), $C_6$-$C_{10}$ aryl ($C_6$, $C_7$, $C_8$, $C_9$, or $C_{10}$), and 5-10 membered heteroaryl (5, 6, 7, 8, 9, or 10).

"Unnatural amino acids" means amino acids and corresponding peptoid oligomers that are synthesized from single amino acid starting materials. Such unnatural amino acids may be prepared and used individually in accordance with the present disclosure, or may incorporated into existing proteins. This method may be used to create analogs with unnatural amino acids. A general method for site-specific incorporation of unnatural amino acids into proteins is described in Christopher J. Noren, Spencer J. Anthony-Cahill, Michael C. Griffith, Peter G. Schultz, Science, 244: 182-188 (April 1989). Examples of unnatural amino acids include, but are not limited to:

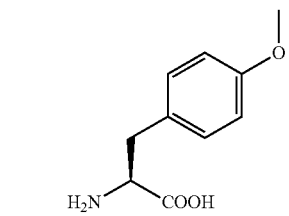

1

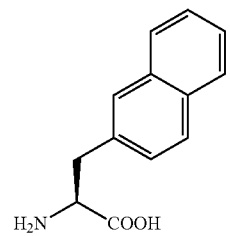

2

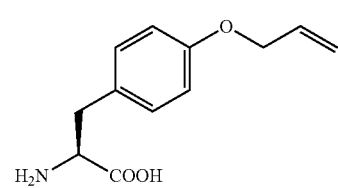

3

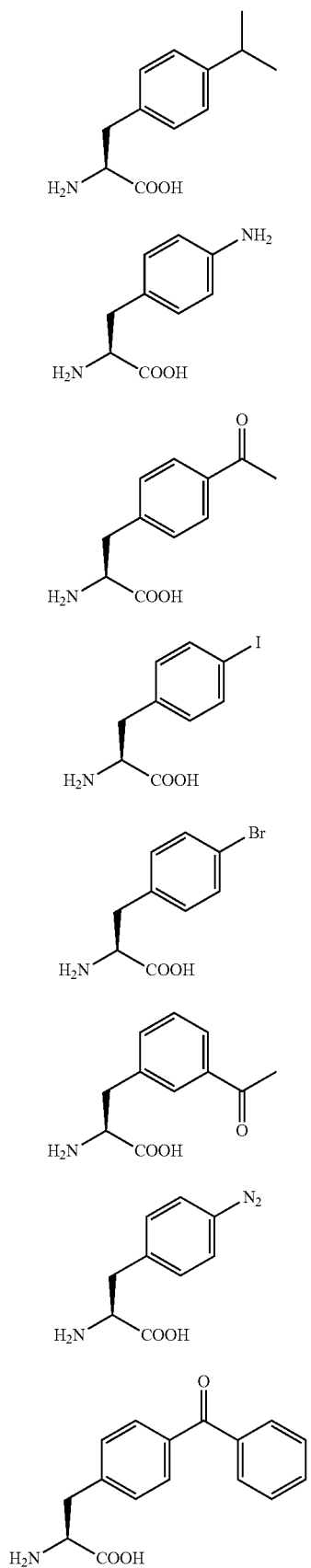
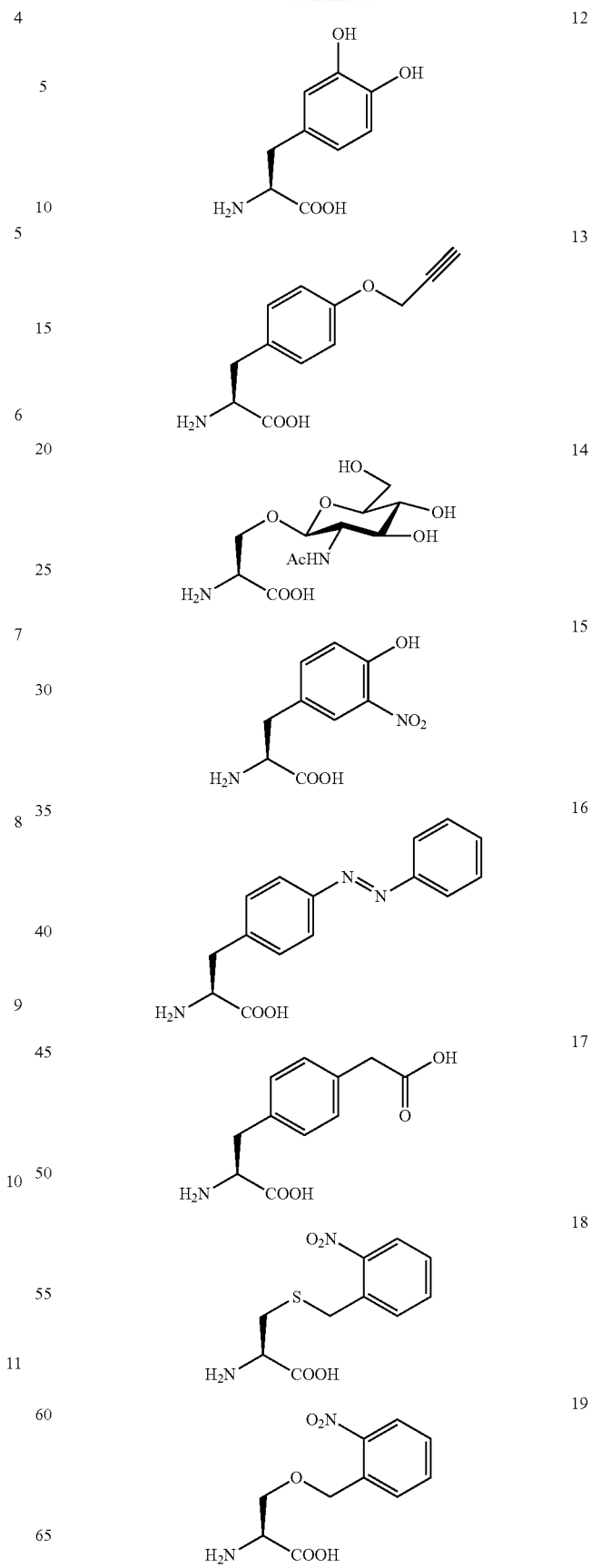

-continued

20
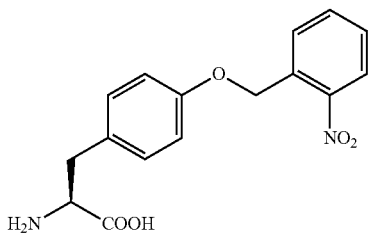

21
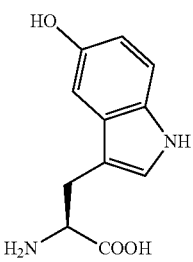

22
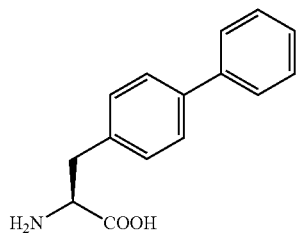

23
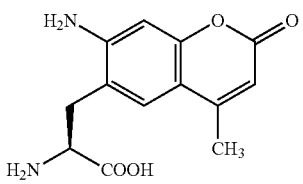

24
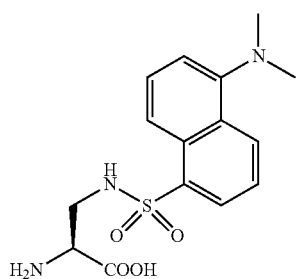

25
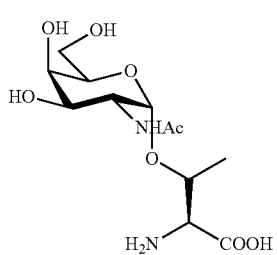

-continued

26
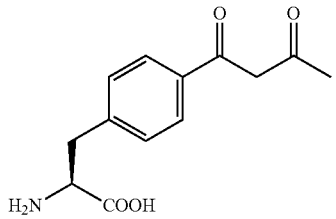

27
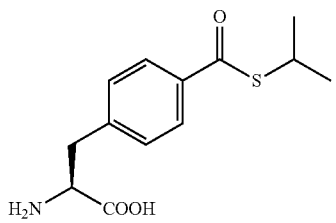

28
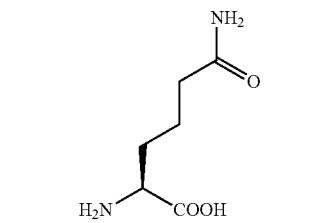

29
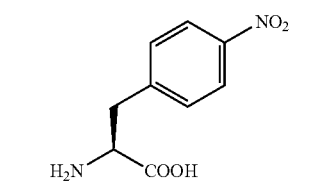

30
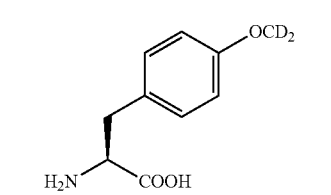

31
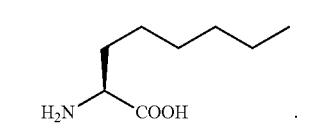

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable vehicle" refers to a diluent, adjuvant, excipient or carrier with which a compound of the disclosure is administered.

"Preventing" or "prevention" refers to a reduction in risk of acquiring a disease or disorder (i.e., causing at least one of the clinical symptoms of the disease not to develop in a subject not yet exposed to or predisposed to the disease, and not yet experiencing or displaying symptoms of the disease).

"Prodrugs" refers to compounds, including derivatives of the compounds provided herein, which have cleavable groups and become by solvolysis or under physiological conditions the compounds provided herein which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds provided herein may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "patient" and "subject" are used interchangeably herein. Accordingly, a subject can be a mammal, in a particular embodiment a human, or a bird, a reptile, an amphibian, or a plant.

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane that are likewise formed by treatment with acid or base. Tautomeric forms may be relevant to the attainment of the optimal chemical reactivity and biological activity of a compound of interest.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both.

Other derivatives of the compounds provided herein may have activity in both their acid and acid derivative forms, but the acid sensitive form may offer advantages of solubility, tissue compatibility, or delayed release in mammalian organisms (see Bundgard, H., Design of Prodrugs, pp. 7-9, 21-24, Elsevier, Amsterdam 1985). Prodrugs include, but are not limited to, acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds provided herein are preferred prodrugs. In some cases it is desirable to prepare double ester type prodrugs such as (acyloxy)alkyl esters or ((alkoxycarbonyl)oxy)alkylesters. Preferred are the $C_1$-$C_8$ alkyl ($C_1$, $C_2$, $C_3$, $C_4$, $C_5$, $C_6$, $C_7$, or $C_8$), $C_2$-$C_8$ alkenyl ($C_2$, $C_3$, $C_4$, $C_5$, $C_6$, $C_7$, or $C_8$), aryl, $C_7$-$C_{12}$ substituted aryl ($C_7$, $C_8$, $C_9$, $C_{10}$, $C_{11}$, or $C_{12}$), and $C_7$-$C_{12}$ arylalkyl esters ($C_1$, $C_8$, $C_9$, $C_{10}$, $C_{11}$, or $C_{12}$) of the compounds provided herein.

As used herein, the term "isotopic variant" refers to a compound that comprises an unnatural proportion of an isotope of one or more of the atoms that constitute such compound. For example, an "isotopic variant" of a compound can comprise an unnatural proportion of one or more non-radioactive isotopes, such as, for example, deuterium ($^2$H or D), carbon-13 ($^{13}$C), nitrogen-15 ($^{15}$N), or the like. It will be understood that, in a compound comprising an unnatural proportion of an isotope, any example of an atom where present, may vary in isotope composition. For example, any hydrogen may be $^2$H/D, or any carbon may be $^{13}$C, or any nitrogen may be $^{15}$N, and that the presence and placement of such atoms may be determined within the skill of the art. Likewise, provided herein are methods for preparation of isotopic variants with radioisotopes, in the instance for example, where the resulting compounds may be used for drug and/or substrate tissue distribution studies. The radioactive isotopes tritium, i.e., $^3$H, and carbon-14, i.e., $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy. All isotopic variants of the compounds provided herein, radioactive or not, are intended to be encompassed within the scope provided herein.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The Peptoid Oligomers

As set forth earlier herein, the macrocycles of the present disclosure comprise substituted hybrid peptoid-peptide macrocycles. The macrocycles may have inhibitory activity towards the Wnt signaling pathway. Accordingly, the peptoid-peptide macrocycles of the disclosure may have anticancer activity.

The present disclosure provides peptoid-based macrocycles that can bind to the surface of the protein β-catenin to modulate the Wnt signaling pathway within cells and to establish a modality for treatment of cancer and other disease states related to aberrant Wnt signaling.

Accordingly, the present disclosure has determined that peptoid-peptide macrocycles may be prepared that exhibit inhibitory activity of the Wnt signaling pathway.

As demonstrated herein, peptoid-peptide macrocycles of the present disclosure may exhibit anticancer activity. These findings lead to novel peptoid oligomers that are promising candidates for therapeutic use. It also leads to pharmaceutical compositions comprising the peptoid-peptide macrocycles of the present disclosure as active ingredients and to their use to treat, prevent, or ameliorate a range of conditions associated with Wnt signaling pathway.

In one aspect, the present disclosure relates to macrocycles where at least one of the peptoid monomers is replaced with an amino acid. In a particular embodiment thereof, the amino acid is a D-isomer of the amino acid. The resulting macrocycles are referred to as peptoid-peptide macrocycles.

More particularly, the present disclosure relates to peptoid-peptide macrocycles, according to formula A:

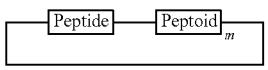
A where "Peptide" is a single amino acid residue, "Peptoid" is N-substituted amino acid residue, and m is an integer from 2-20; or a pharmaceutically acceptable salt, solvate or prodrug thereof; and stereoisomers, isotopic variants and tautomers thereof, provided that i) the compound is other than:

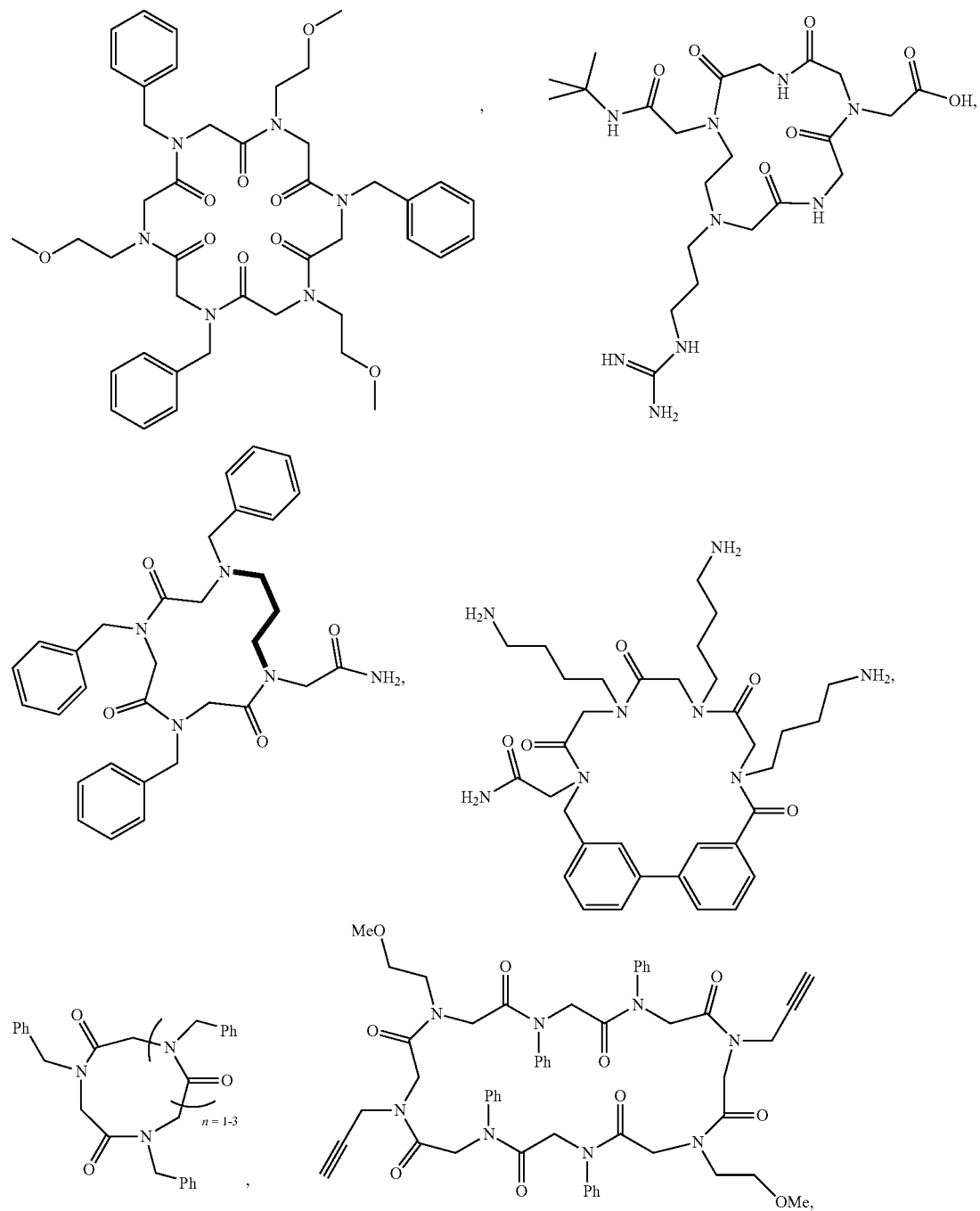

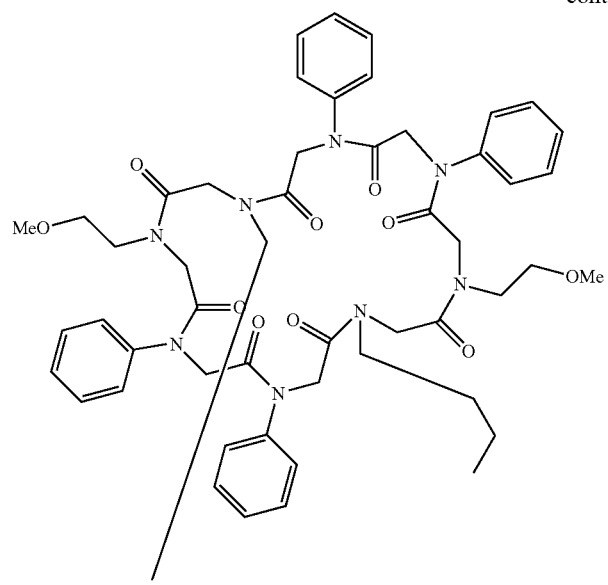
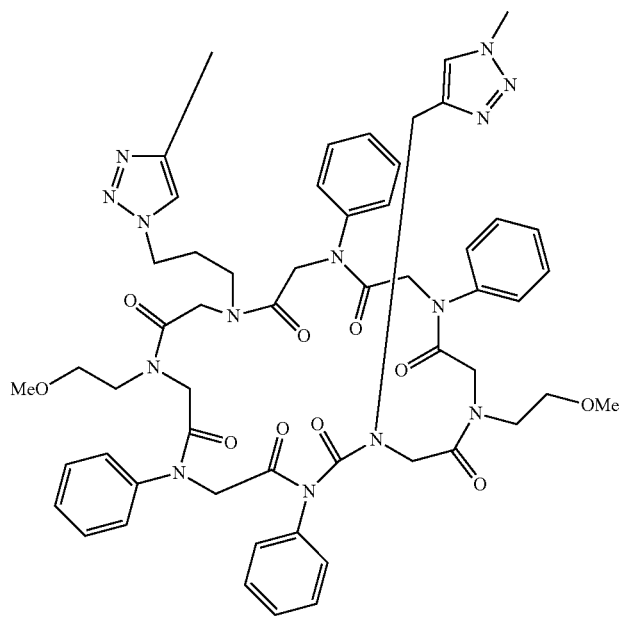

-continued
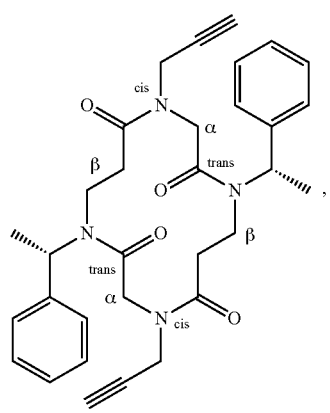
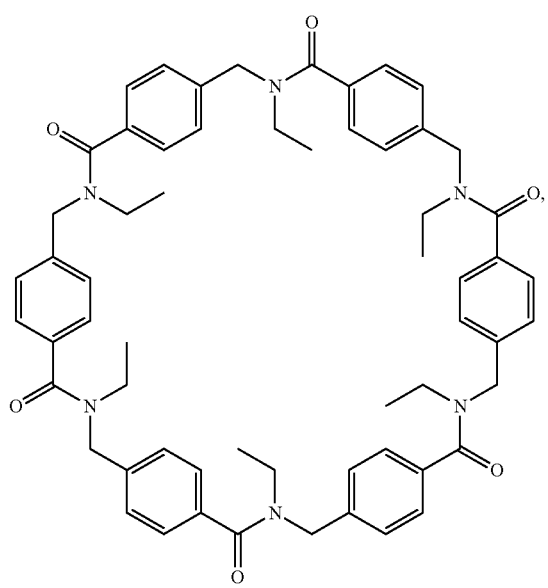
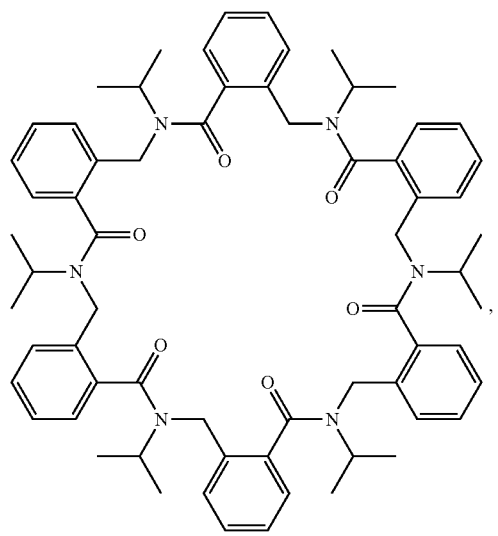
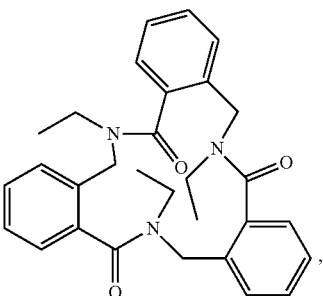
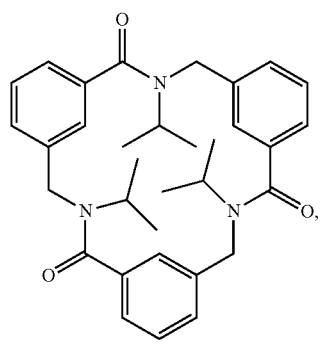
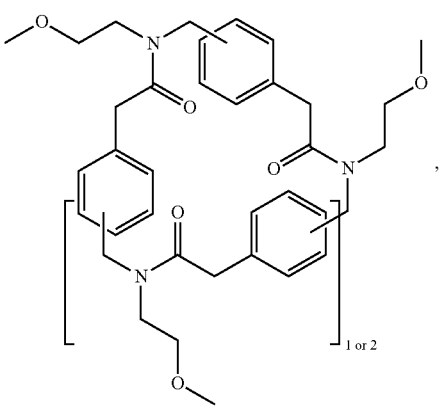

-continued
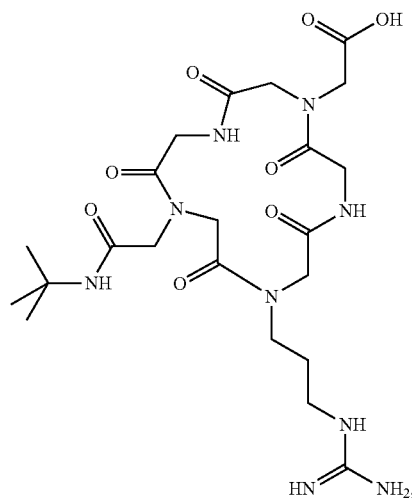
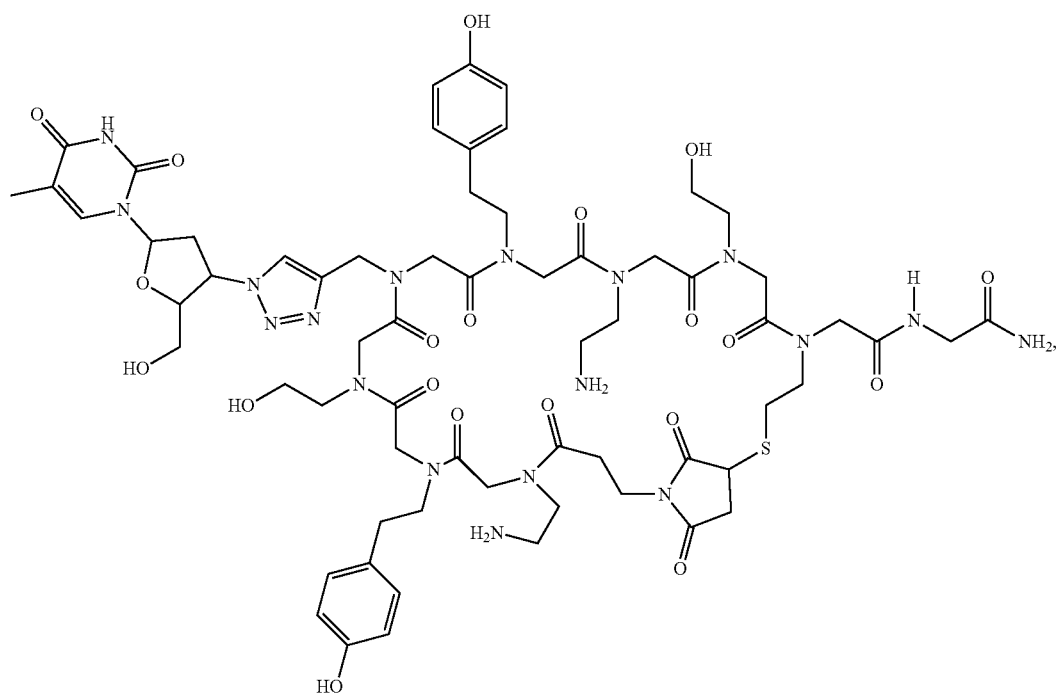

-continued
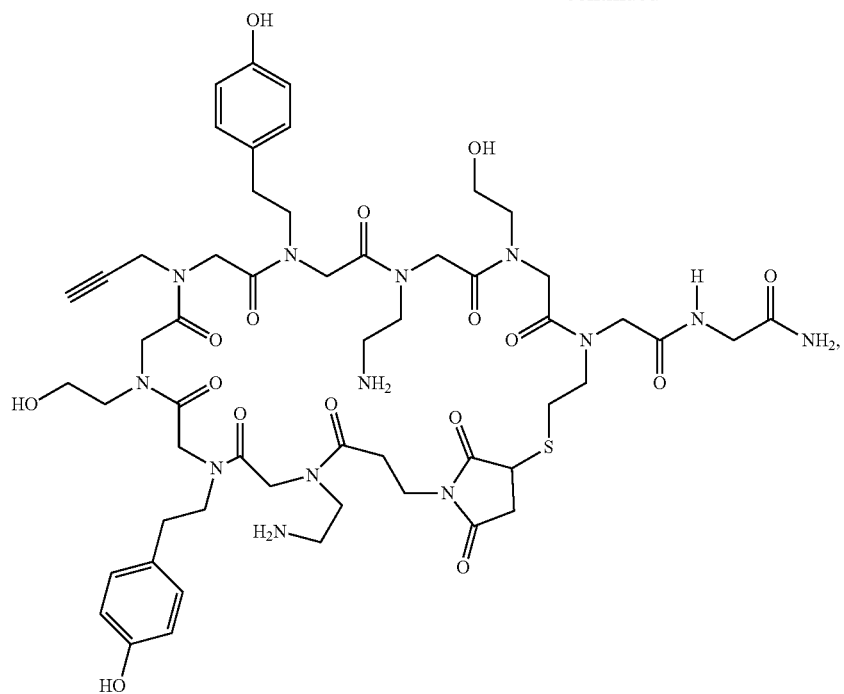
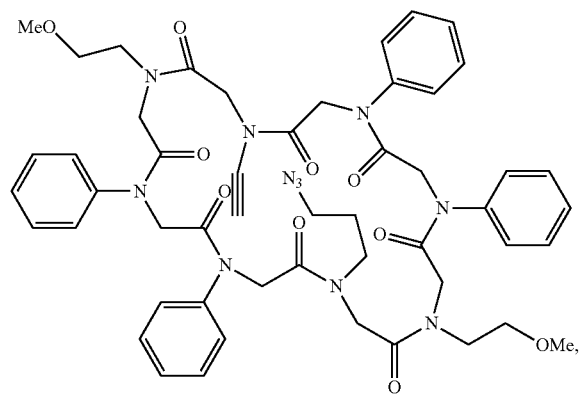
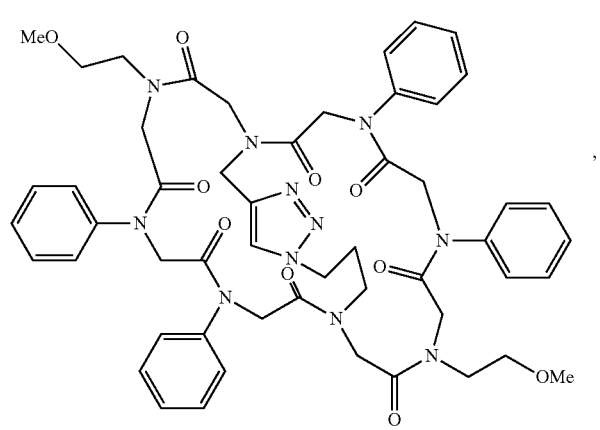
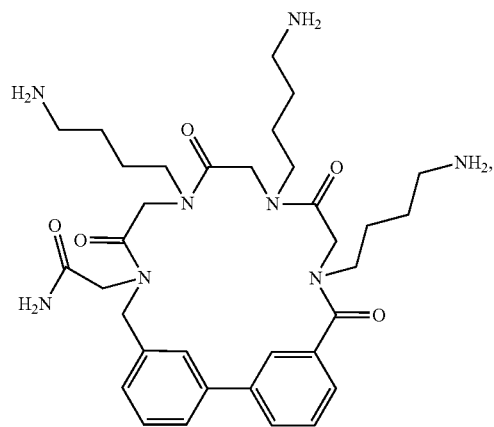

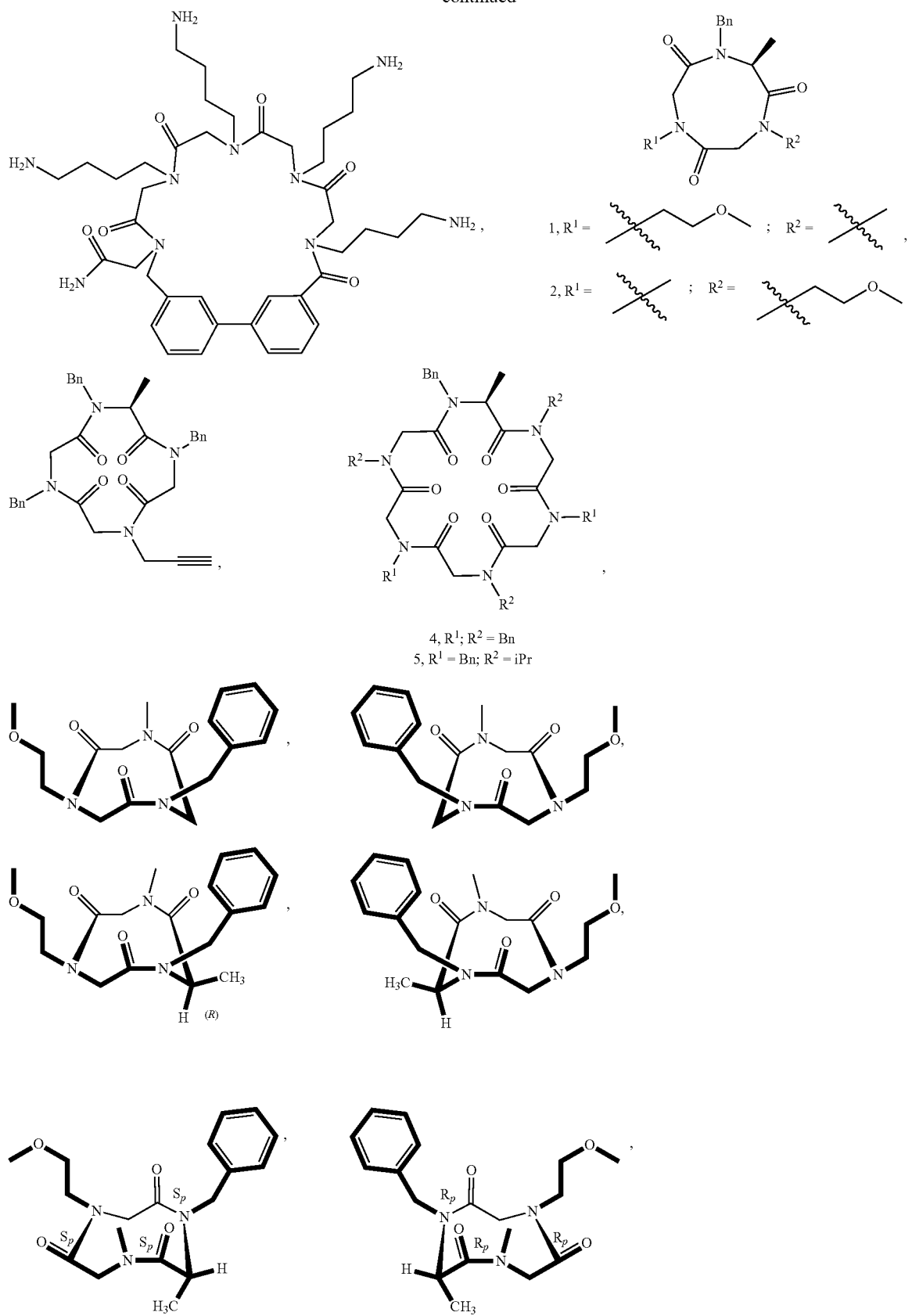

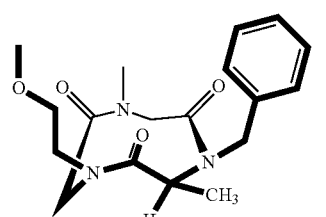
,
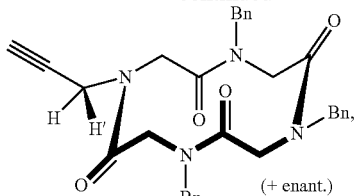
(+ enant.)
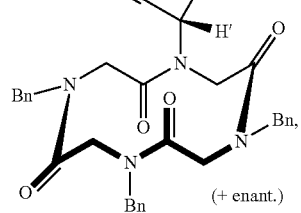
(+ enant.)
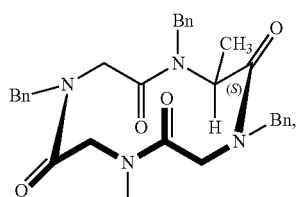
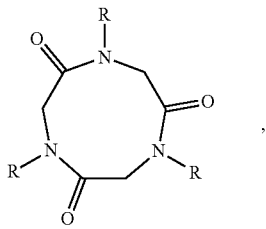
,
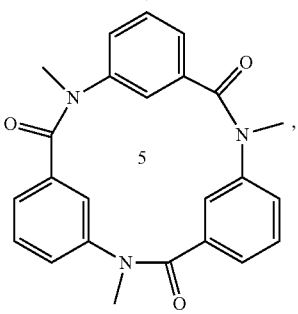
 1
 2
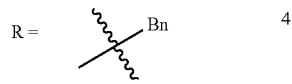 3
R = Bn  4
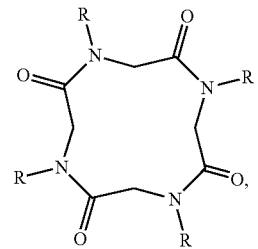
,
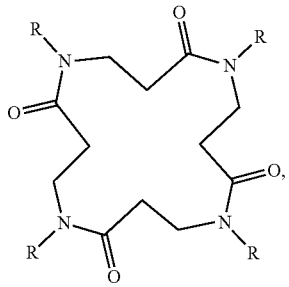
 7
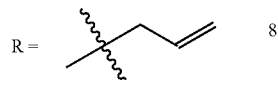 8
R = Bn  9
R = (structure) 10

-continued
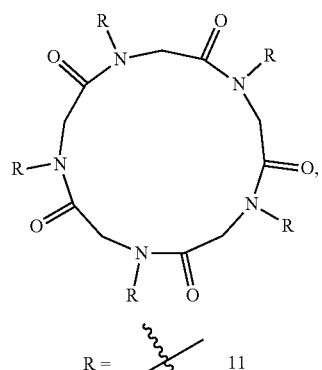
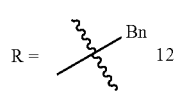
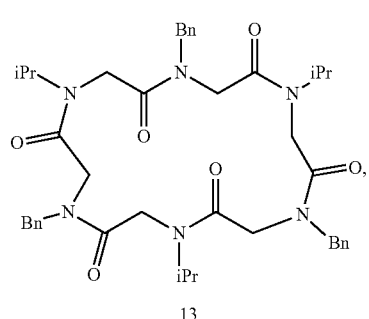
13
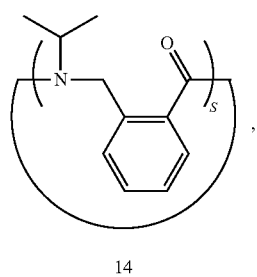
14
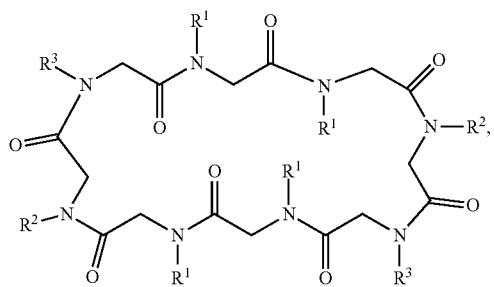
15
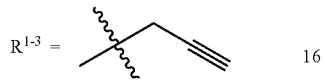
16
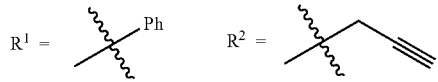
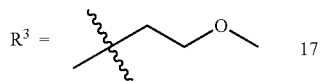
17

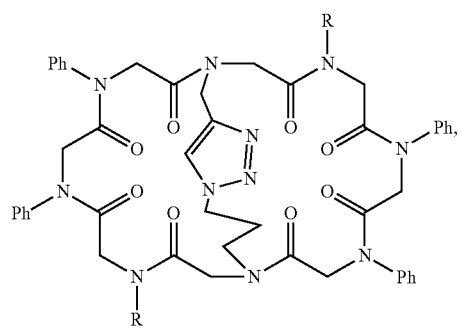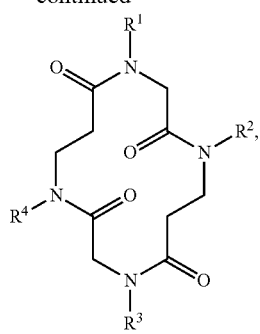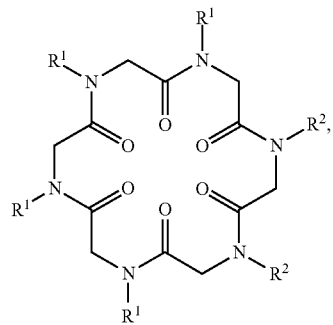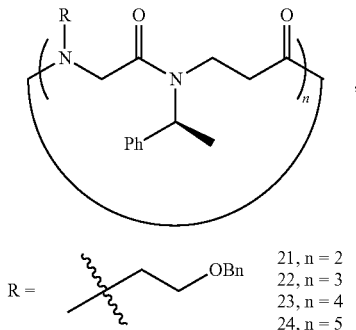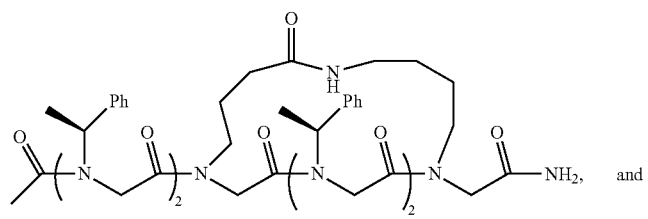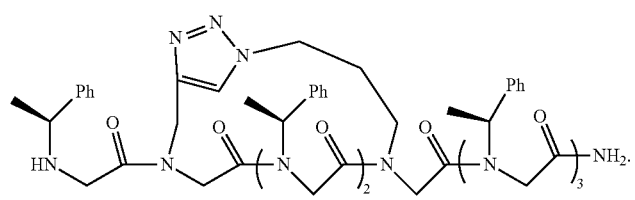

In another aspect, the present disclosure provides methods to treat, prevent or ameliorate a range of conditions associated with the Wnt signaling pathway using peptoid-peptide macrocycles described herein.

In one embodiment, peptoid-peptide macrocycle is according to formula I, where "Peptide" refers to glycine, D-alanine, D-valine, D-leucine, D-isoleucine, D-tyrosine, D-proline, D-serine, D-glutamic acid, D-tryptophan, D-phenylalanine, D-methionine, D-arginine, D-histidine, D-glutamine, D-lysine, D-aspartic acid, D-threonine, D-cysteine, or D-asparagine.

In one embodiment, peptoid-peptide macrocycle is according to formula I, where "Peptide" refers to glycine, L-alanine, L-valine, L-leucine, L-isoleucine, L-tyrosine, L-proline, L-serine, L-glutamic acid, L-tryptophan, L-phenylalanine, L-methionine, L-arginine, L-histidine, L-glutamine, L-lysine, L-aspartic acid, L-threonine, L-cysteine, or L-asparagine.

In one embodiment, "Peptide" refers to D-alanine. In another embodiment, "Peptoid" is N-substituted glycine.

In another embodiment, "Peptide" is

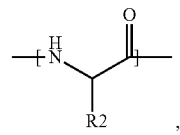

where $R^2$ is selected from substituted or unsubstituted alkyl. The stereochemistry at the alpha carbon is R or S.

In another embodiment, "Peptide" is

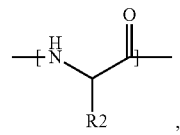

where the moiety —NH—CH($R^2$)—C(O)— is an amino acid residue. A peptide comprises a plurality of amino acid residues. The stereochemistry at the alpha carbon is R or S.

In one particular embodiment, $R^2$ is H or Me.

In an embodiment, $R^2$ is the side chain of a canonical, natural amino acid, or unnatural amino acid as disclosed herein.

In another embodiment, "Peptide" comprises canonical amino acid residues, natural amino acid residues, unnatural amino acid residues, beta-amino acid residues, gamma-amino acid residues, oligo-urea residues, aromatic oligoamide residues, or a combination thereof.

In one embodiment, peptoid-peptide macrocycle is according to formula I, "Peptoid" is an N-substituted amino acid residue, and the N-substitution is selected from substituted or unsubstituted alkyl, substituted or unsubstituted cycloalkyl, substituted or unsubstituted heterocycloalkyl, substituted or unsubstituted aryl, and substituted or unsubstituted heteroaryl. In a particular embodiment, "Peptoid" is an N-substituted amino acid residue, and the amino acid residue is a glycine residue.

In another embodiment, "Peptoid" is a plurality of peptoid residues (e.g., N-substituted glycine residues), beta-peptoid residues, alpha-beta alternating peptoid residues, azapeptoid residues, aminoxypeptoid residues, ureapeptoid residues, or a combination thereof.

In another embodiment, "Peptoid" is

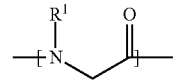

where $R^1$ is selected from substituted or unsubstituted alkyl, substituted or unsubstituted cycloalkyl, substituted or unsubstituted heterocycloalkyl, substituted or unsubstituted aryl, and substituted or unsubstituted heteroaryl, and the entire moiety is referred to as a peptoid residue. "Peptoid" may comprise a plurality of residues that are the same or different. Examples of peptoid residues include, but are not limited to, "N-meo": N-(methoxy-ethyl)-glycine, "N-mpe": N-(4-methoxy-phenyl-ethyl)-glycine, "N-dmp": N-(3,5-dimethoxy-phenyl)-glycine, "N-Smpe": N—((S)-4-methoxy-phenyl-ethyl)-glycine, "N-Sfpe": N—((S)-4-fluoro-phenyl-ethyl)-glycine, "N-mpp": N-(2-phenoxy-phenyl-ethyl)-glycine, "N-ipp": N-(isopropoxy-propyl)-glycine, and "N-mop": N-(methoxy-propyl)-glycine. Examples of $R^1$ substitutents include, but are not limited to, methoxy-ethyl; 4-methoxy-phenyl-ethyl; 3,5-dimethoxy-phenyl; (S)-4-methoxy-phenyl-ethyl; (S)-4-fluoro-phenyl-ethyl; 2-phenoxy-phenyl-ethyl; isopropoxy-propyl; and methoxy-propyl. Additional non-limiting examples of peptoid residues include the peptoid residues of the following compounds:

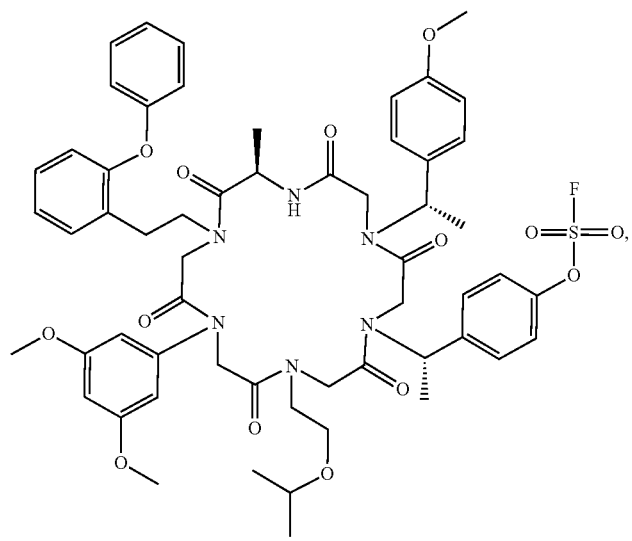
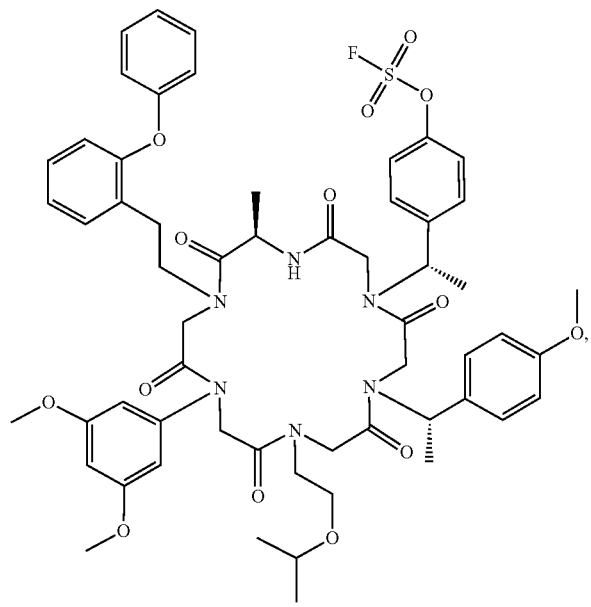
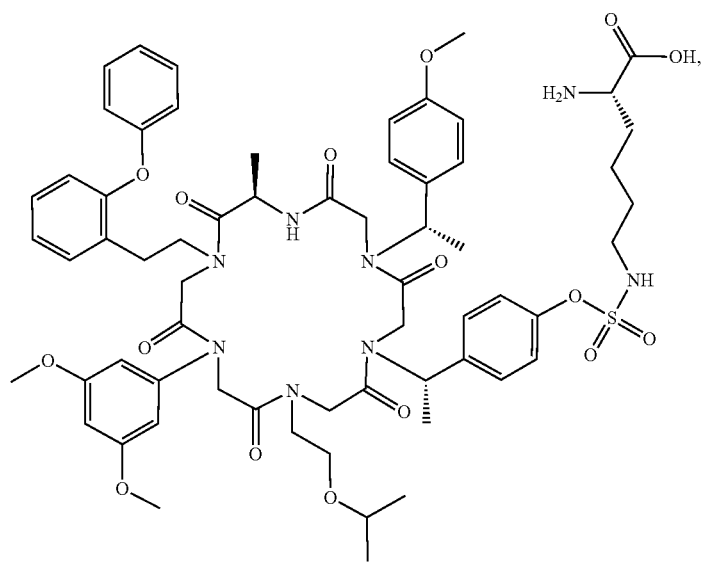

-continued
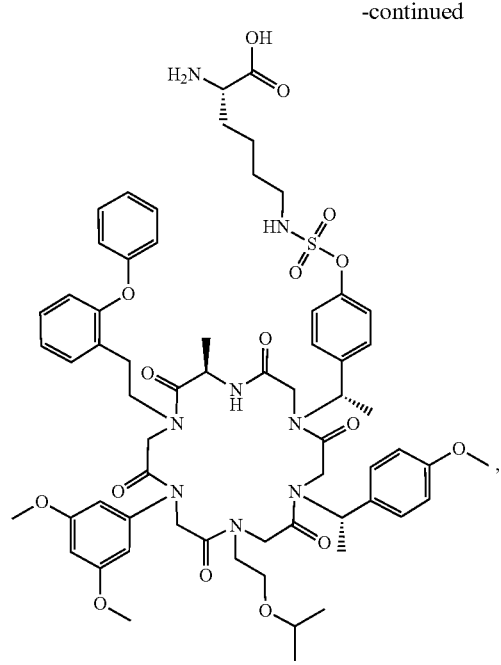
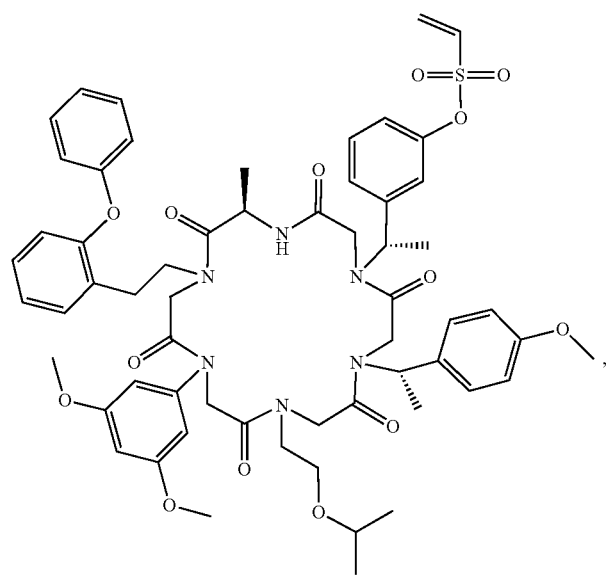

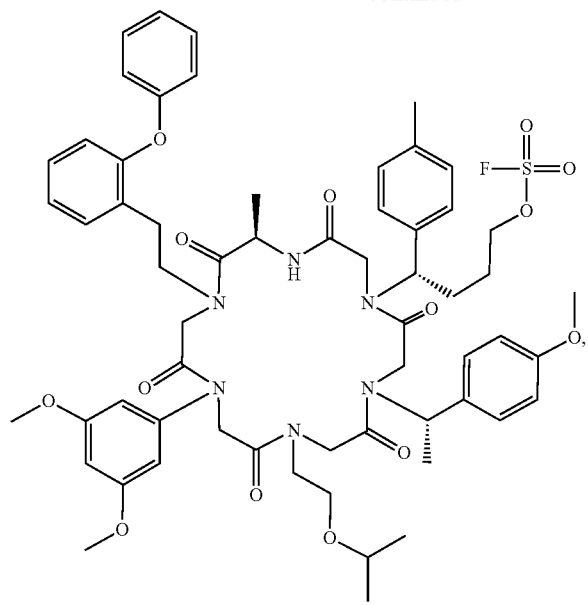
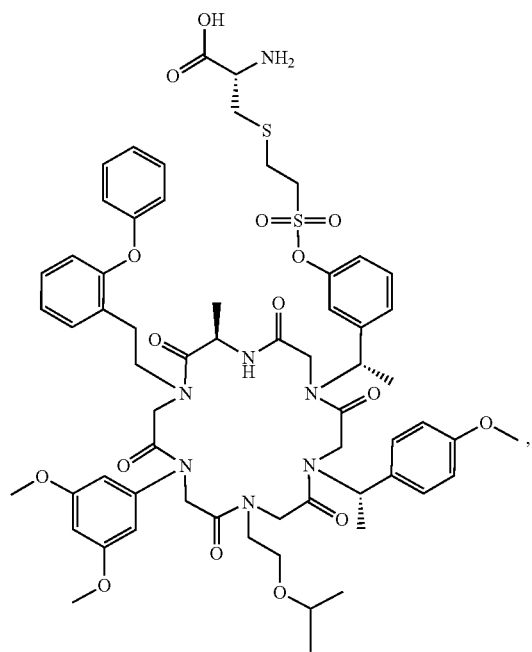

-continued
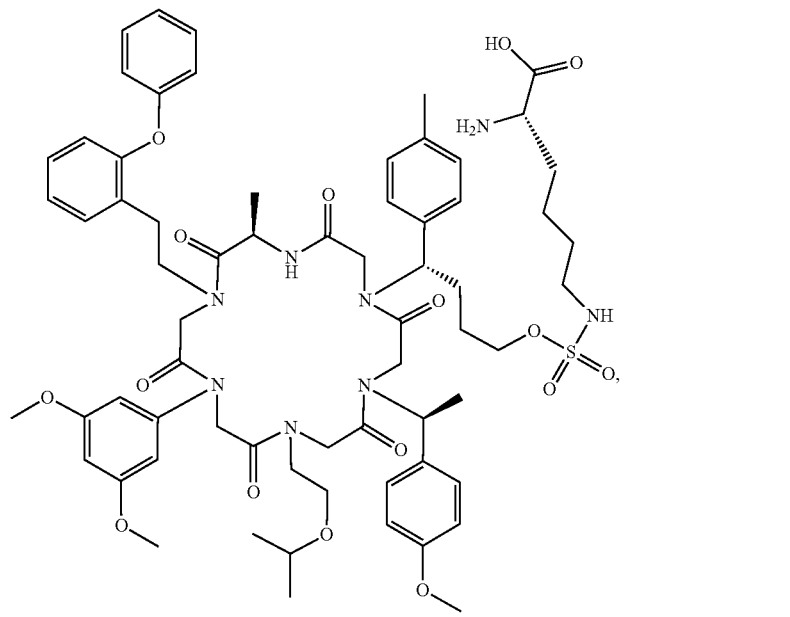
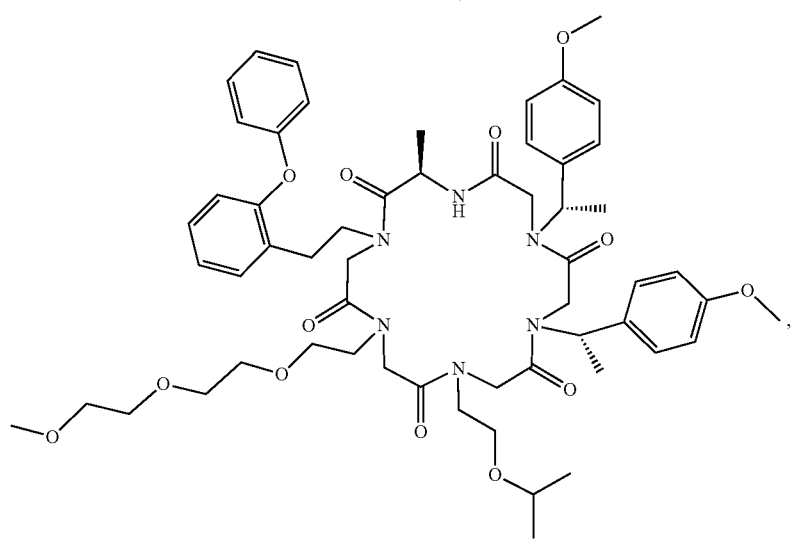
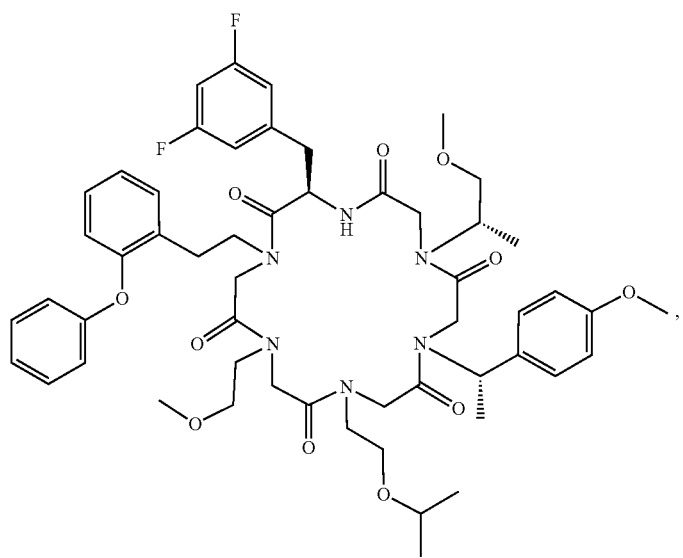

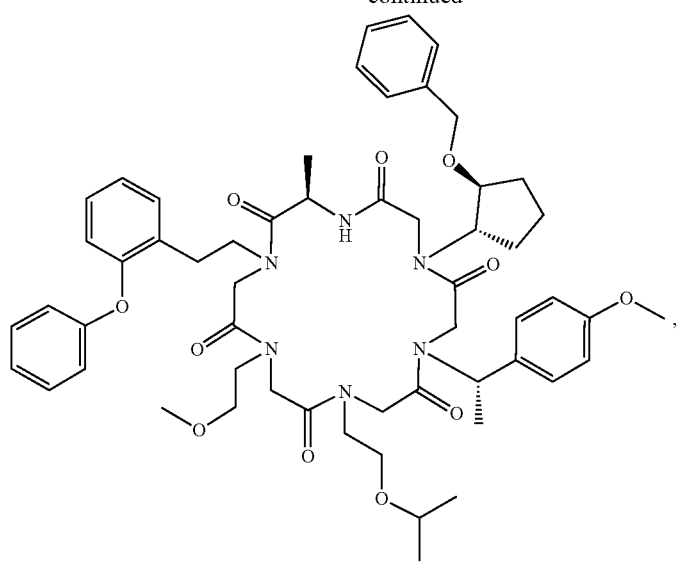
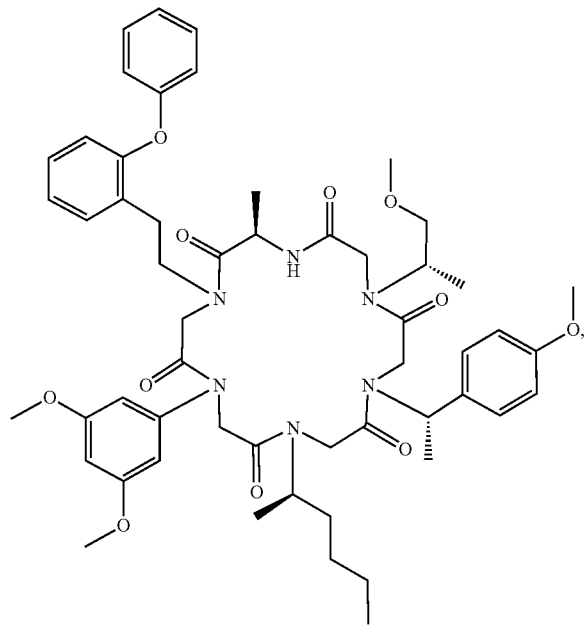
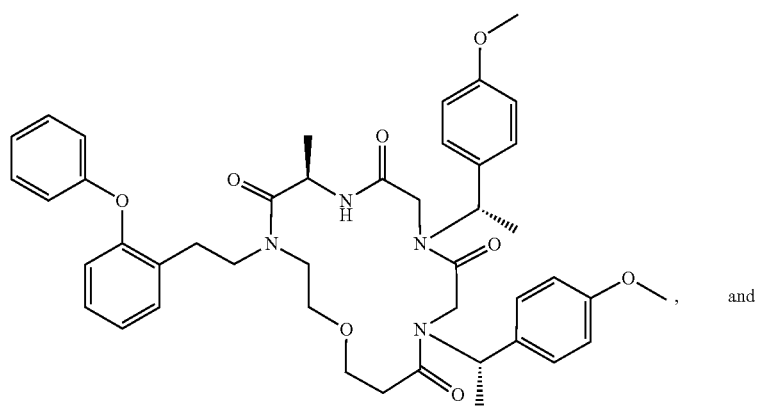

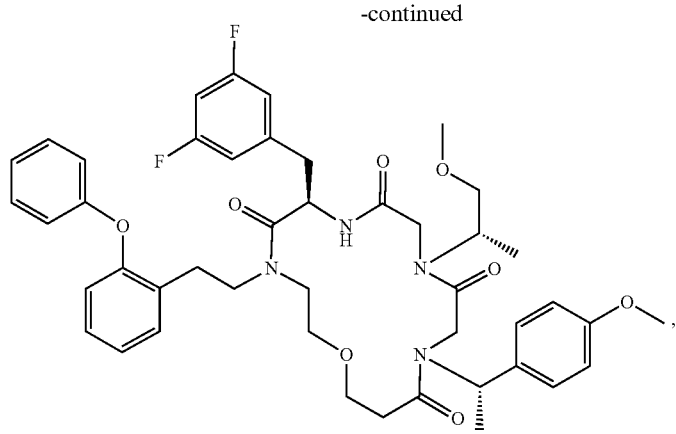

which are also peptoid-peptide macrocycles of the present disclosure.

In an example, the amine submonomers are used to generate N-substituted residues (e.g., peptoid residues). As an illustrative example, an amine submonomer is incorporated as follows:

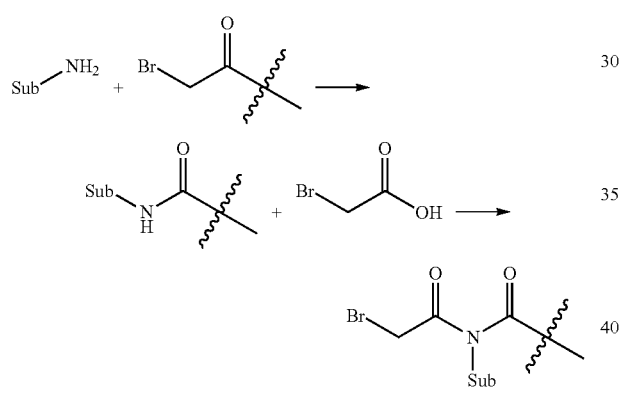

where sub is the remainder of the submonomer. Examples of amine submonomers include, but are not limited to, the following:

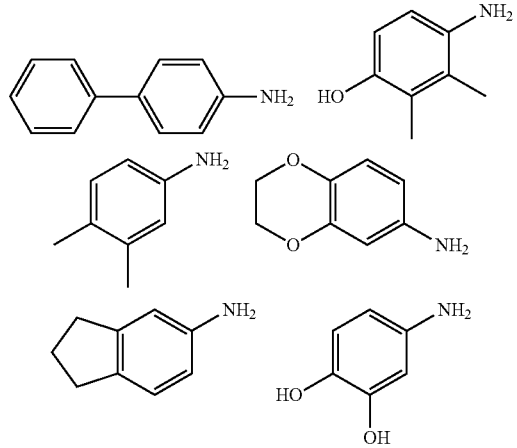

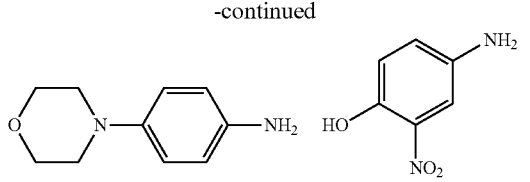

Needs KI additive and MCA

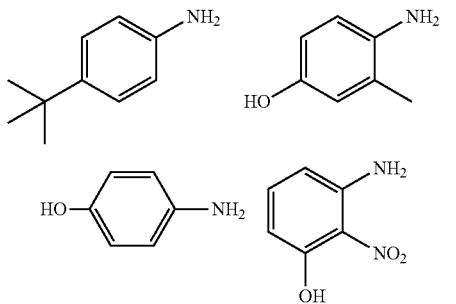

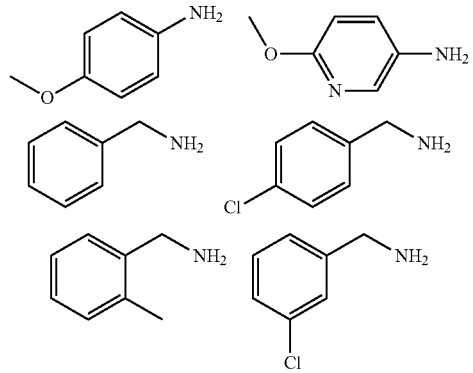

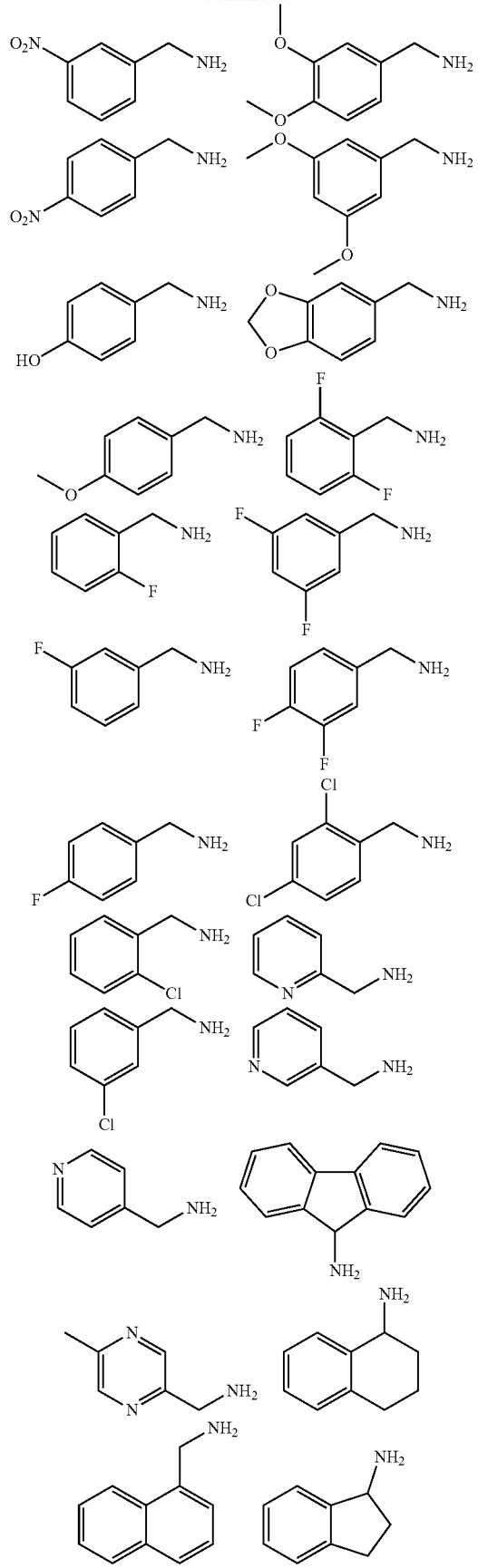
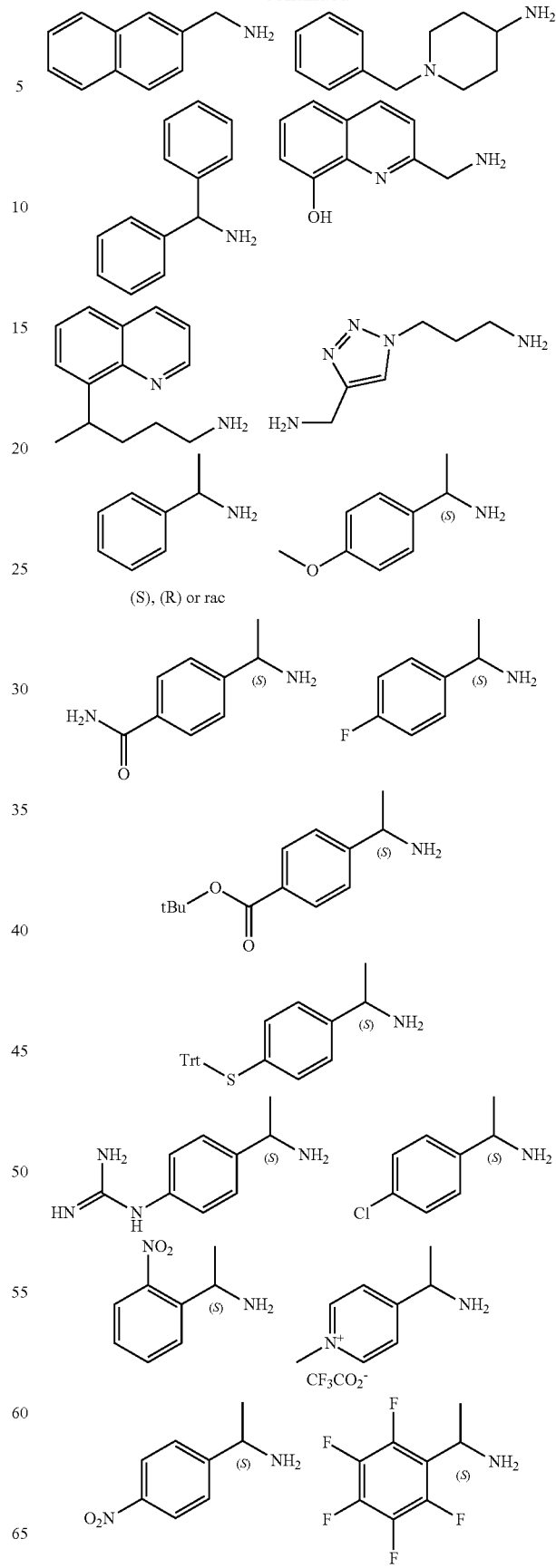

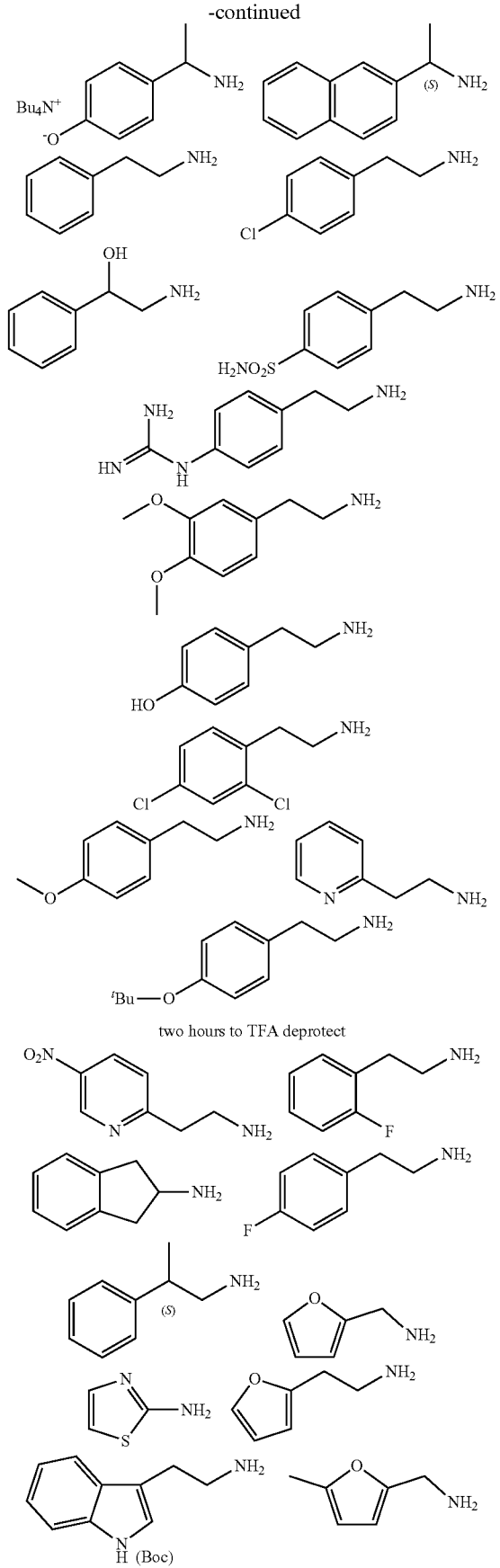
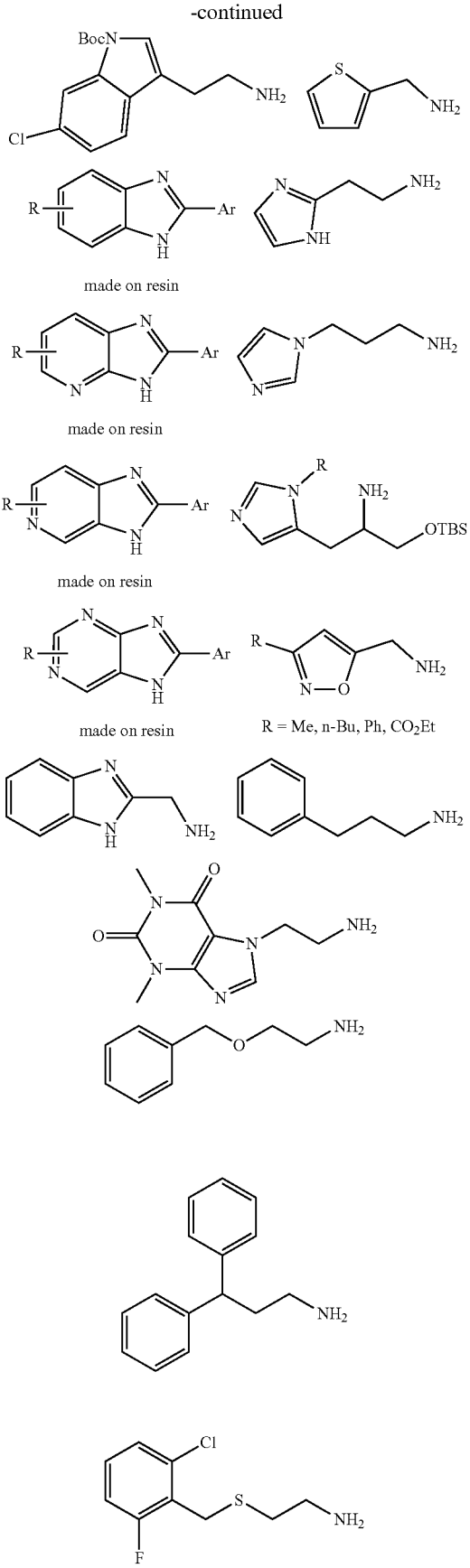

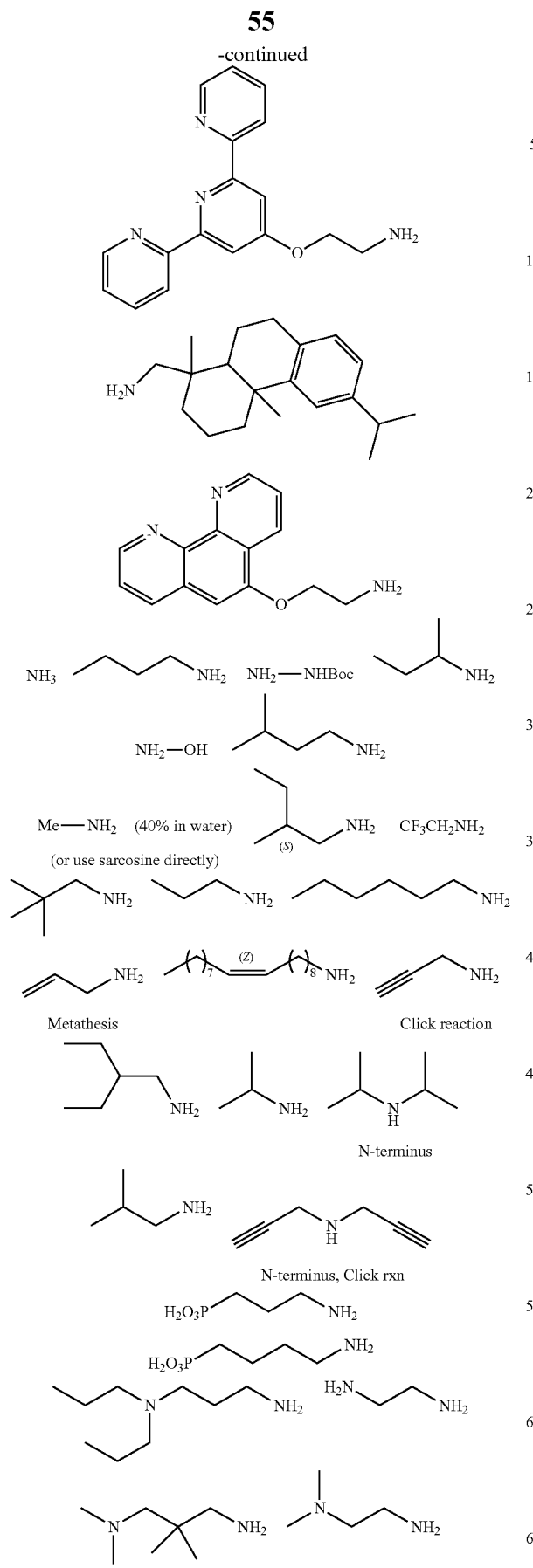
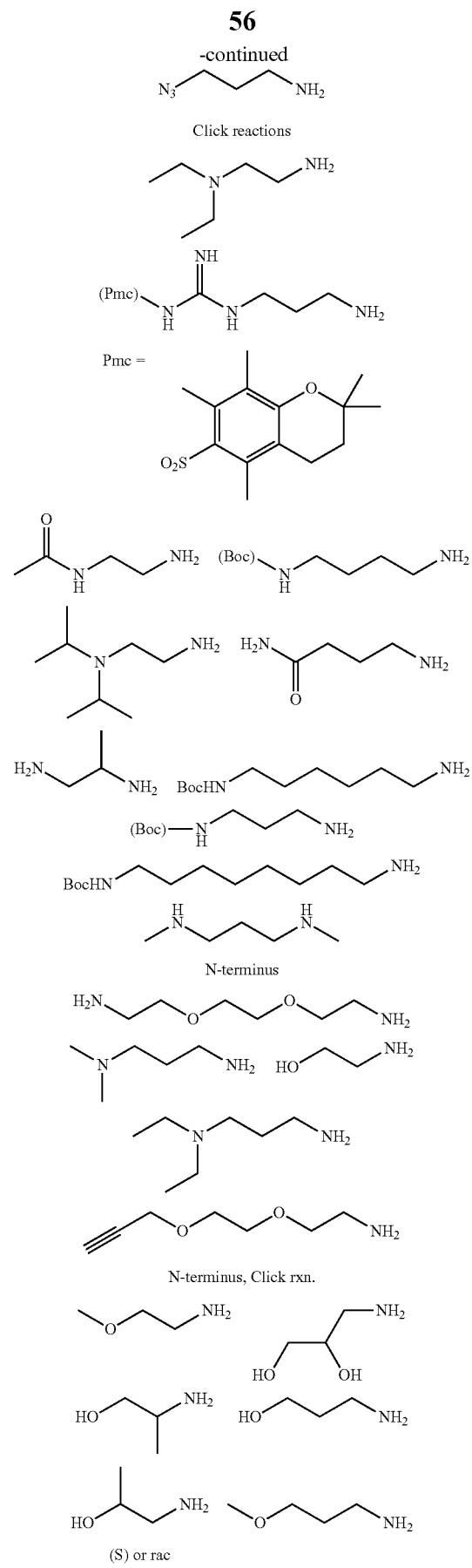

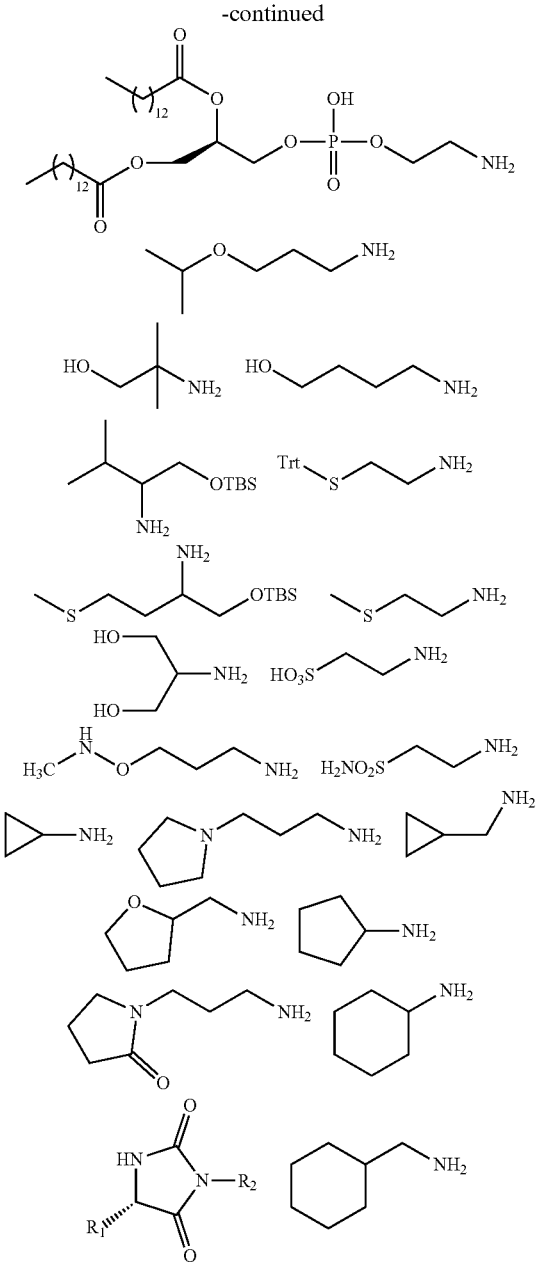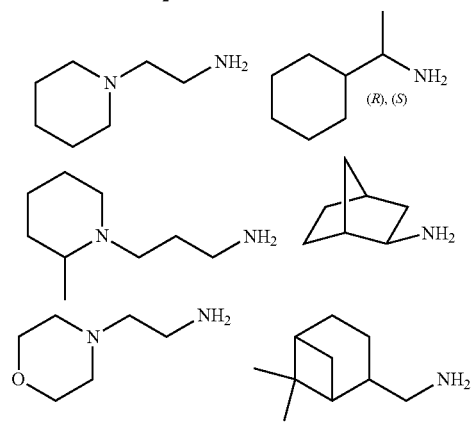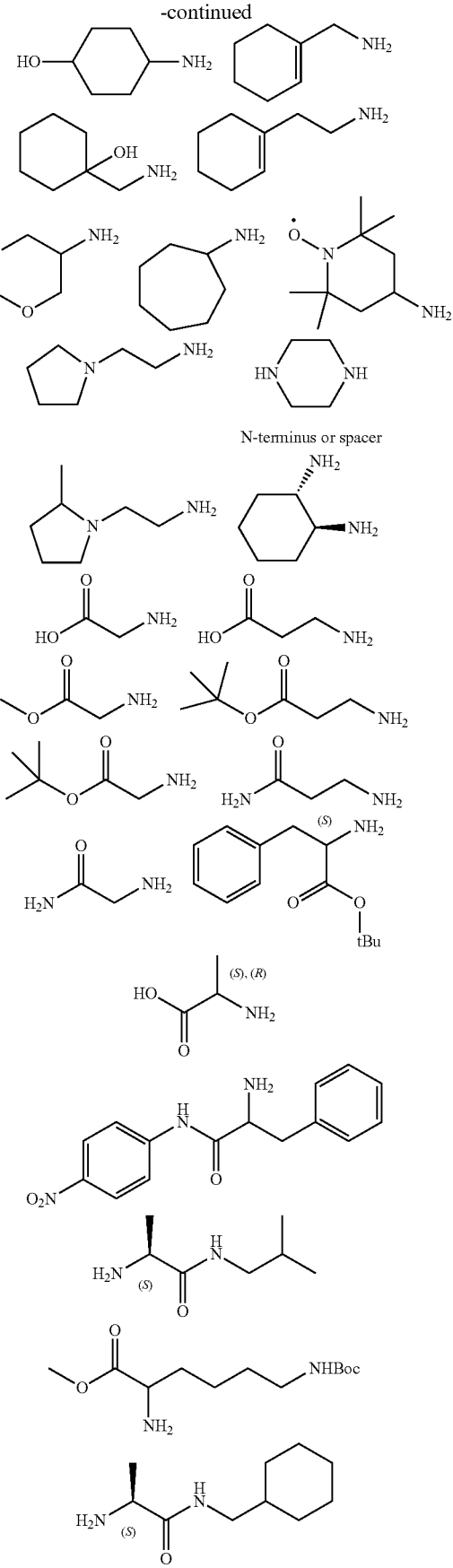

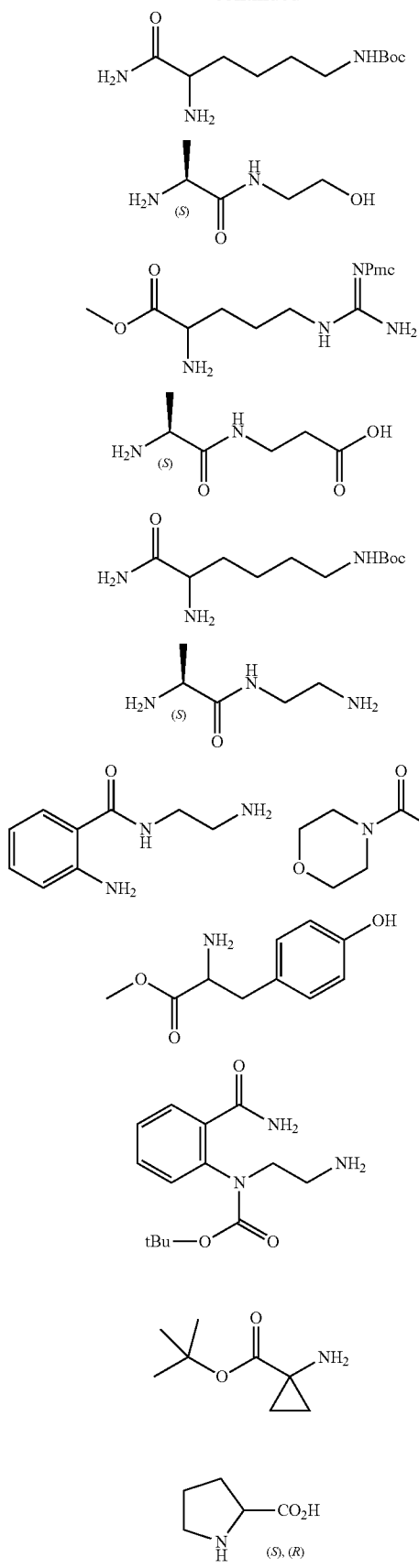
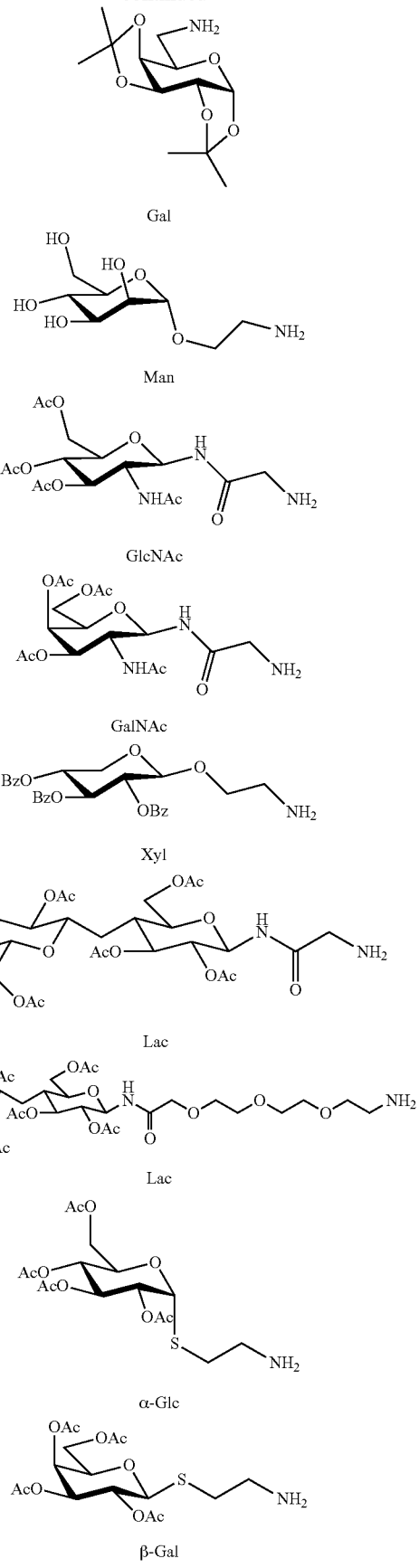

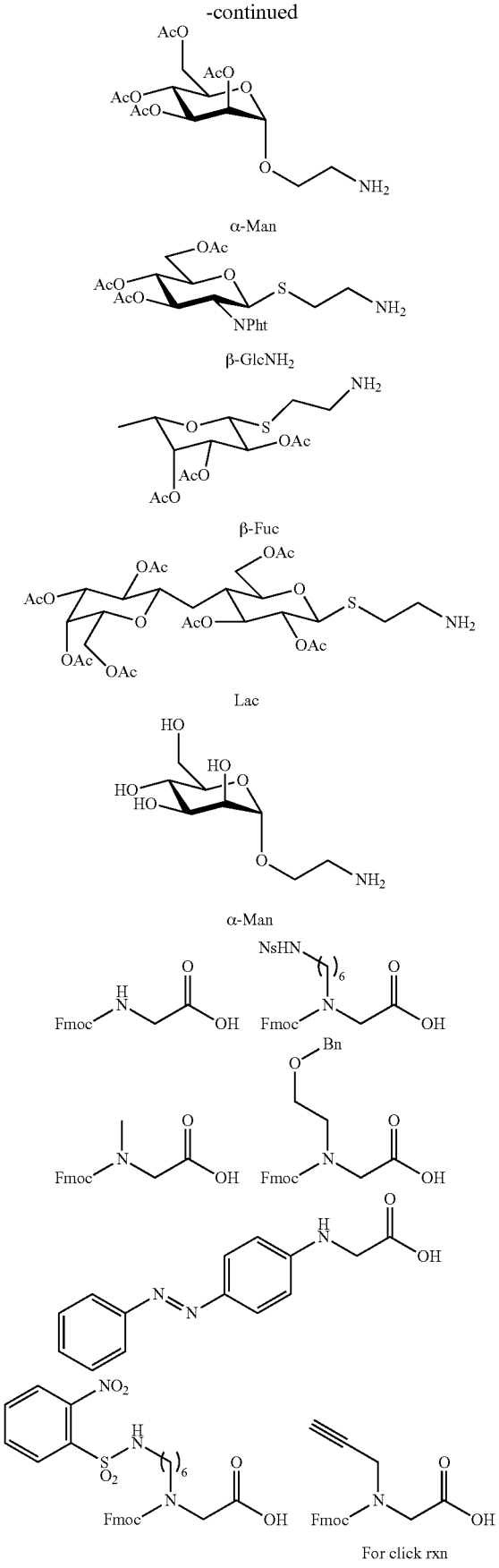
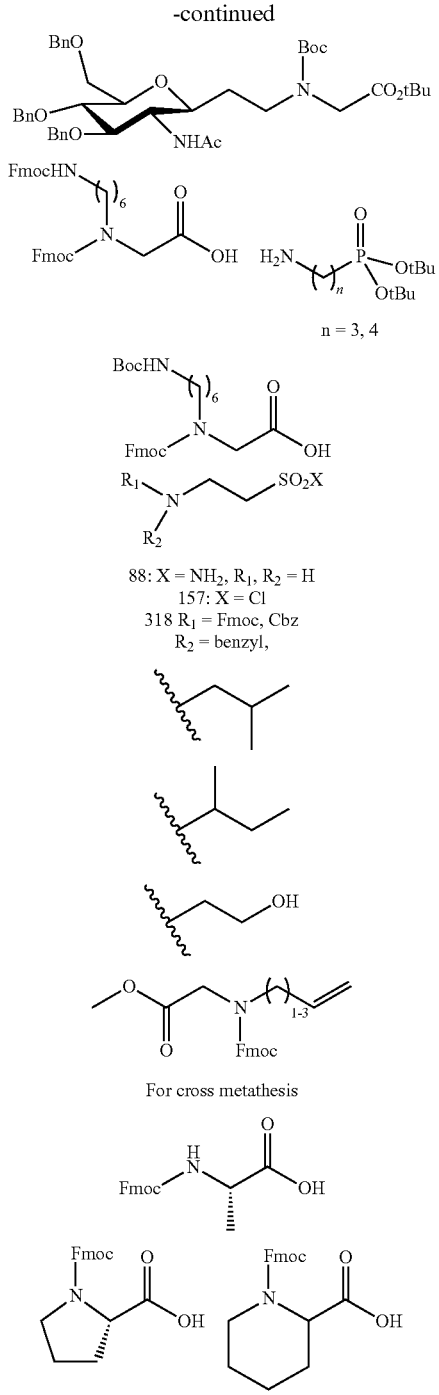
In an embodiment, "Peptoid" comprises peptoid residues, beta-peptoid residues; alpha-beta alternating peptoid residues, azapeptoid residues, aminoxypeptoid residues, ureapeptoid residues, or combinations thereof.
In another embodiment, the peptoid-peptide macrocycle is according to formula I:

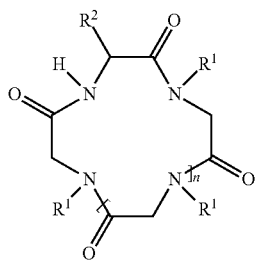

or a pharmaceutically acceptable salt, solvate or prodrug thereof; and stereoisomers, isotopic variants and tautomers thereof; wherein the moiety —NH—CH(R$^2$)—C(O)— is an amino acid residue; each R$^1$ is independently substituted or unsubstituted alkyl, substituted or unsubstituted cycloalkyl, substituted or unsubstituted heterocycloalkyl, substituted or unsubstituted aryl, or substituted or unsubstituted heteroaryl; the subscript n is an integer from 0 to 20 (e.g., 0-15), including all integer values and ranges therebetween; and provided that i) the compound is other than (e.g., the compound (e.g., peptoid-peptide macrocycle) is not one or more or all of these):

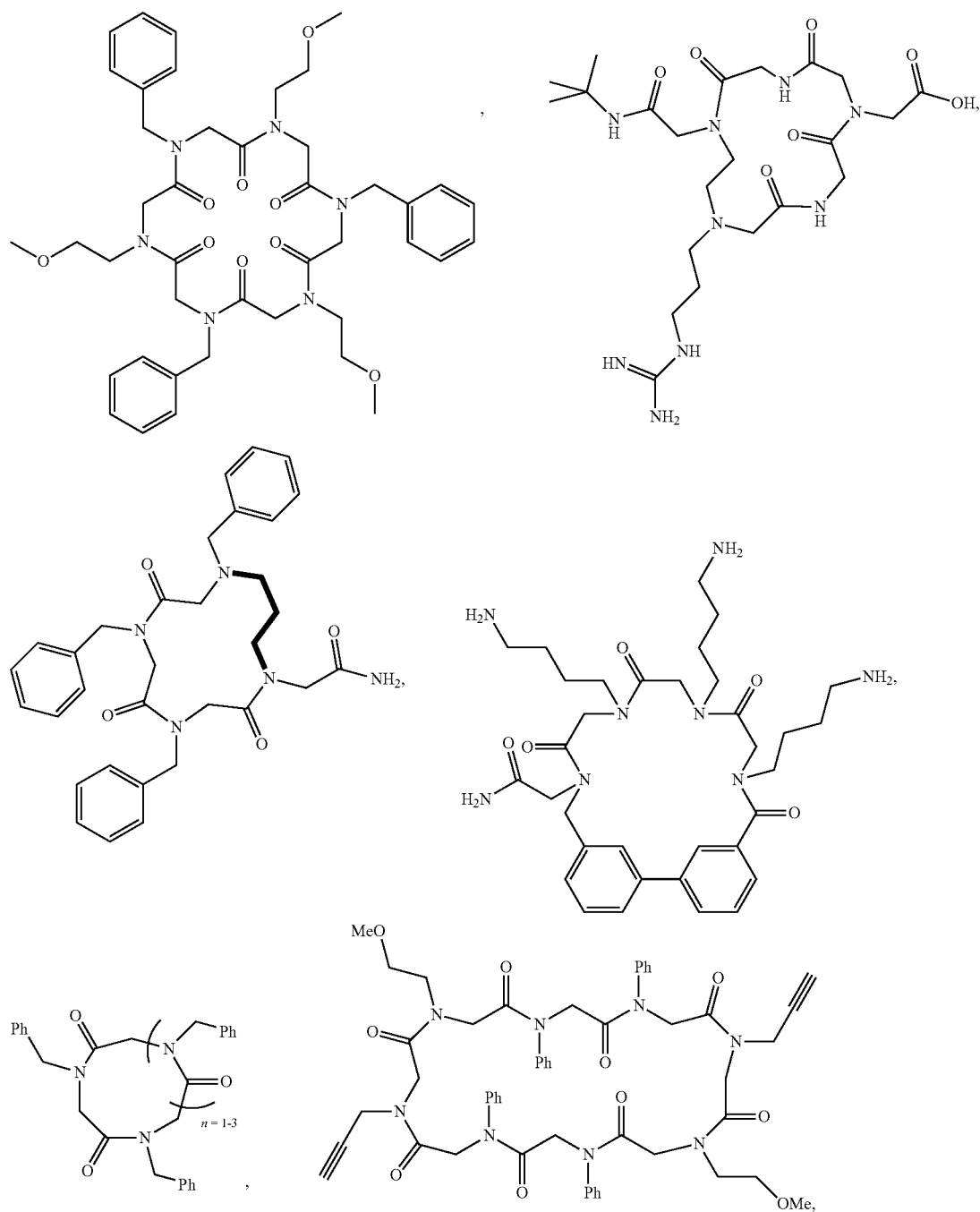

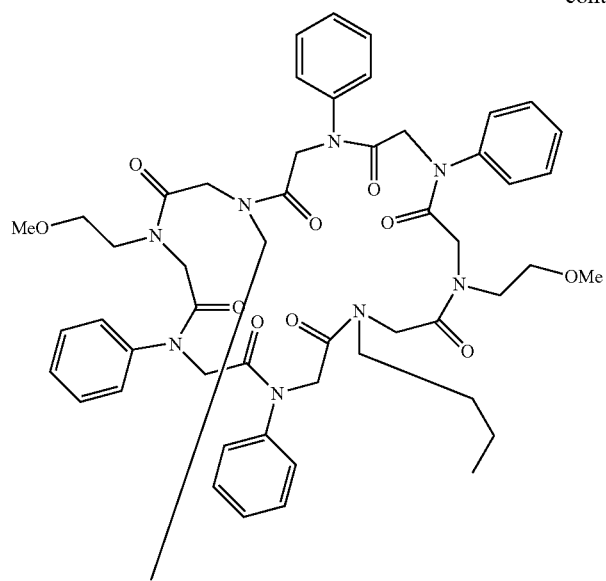
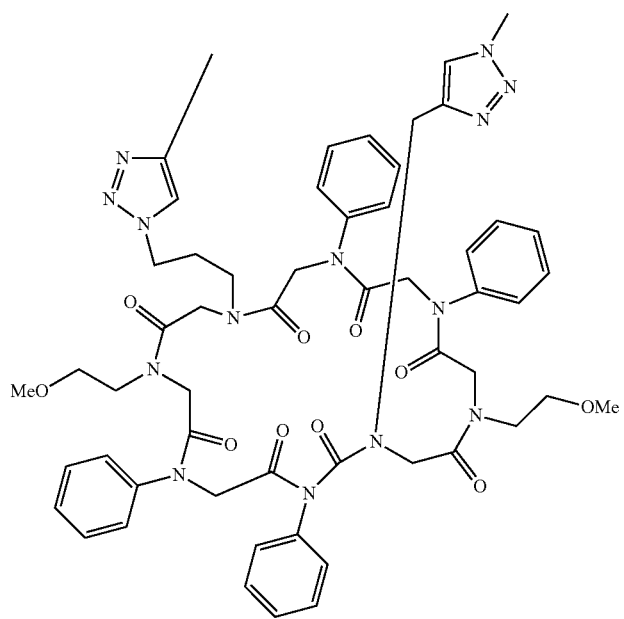

-continued
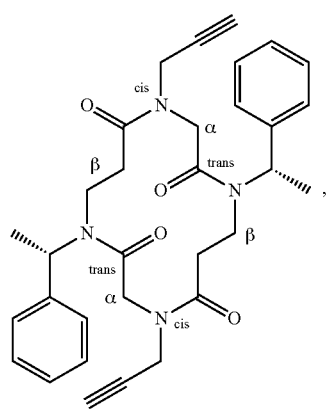 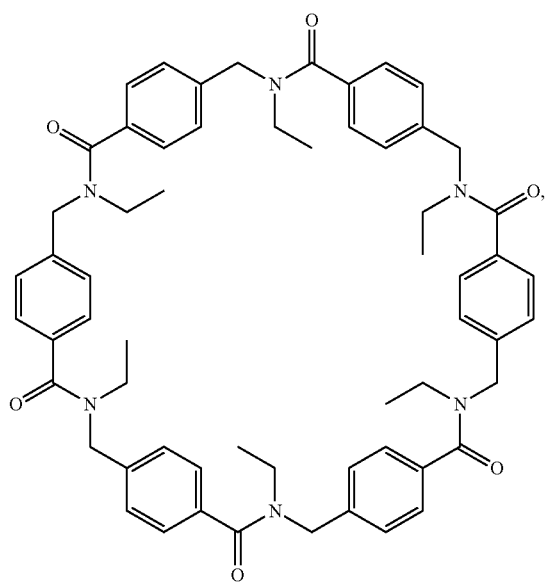
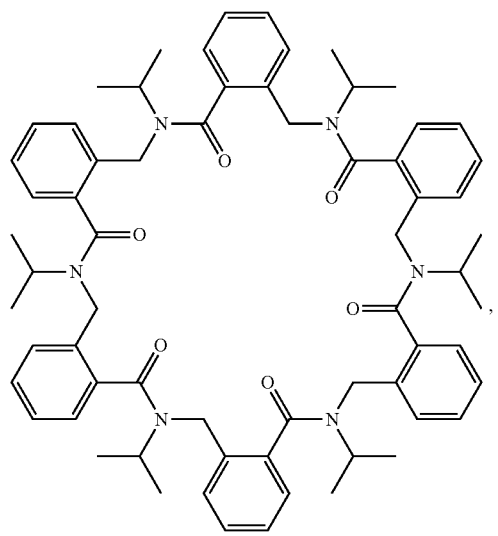 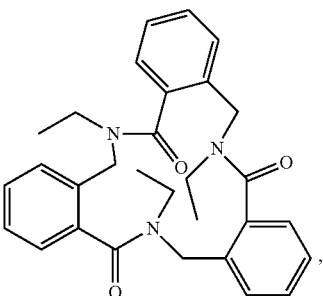
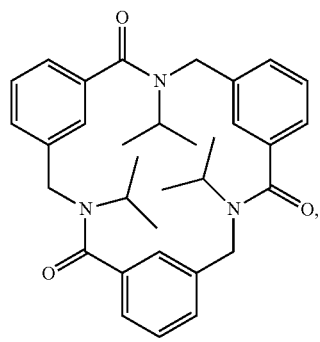 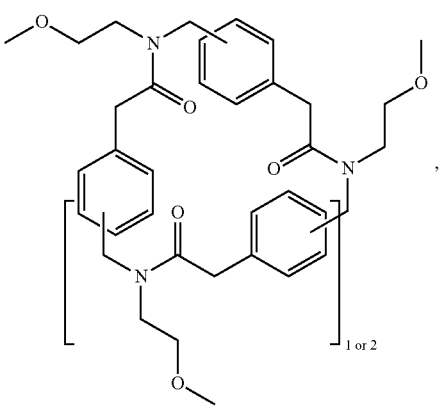

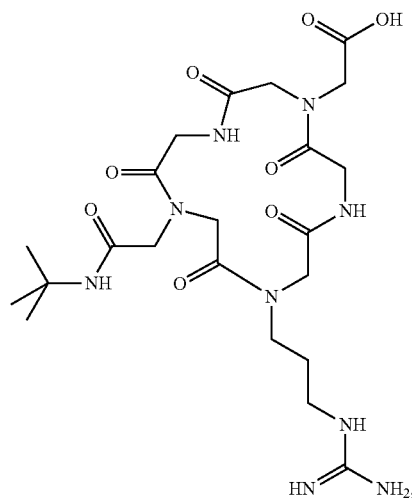
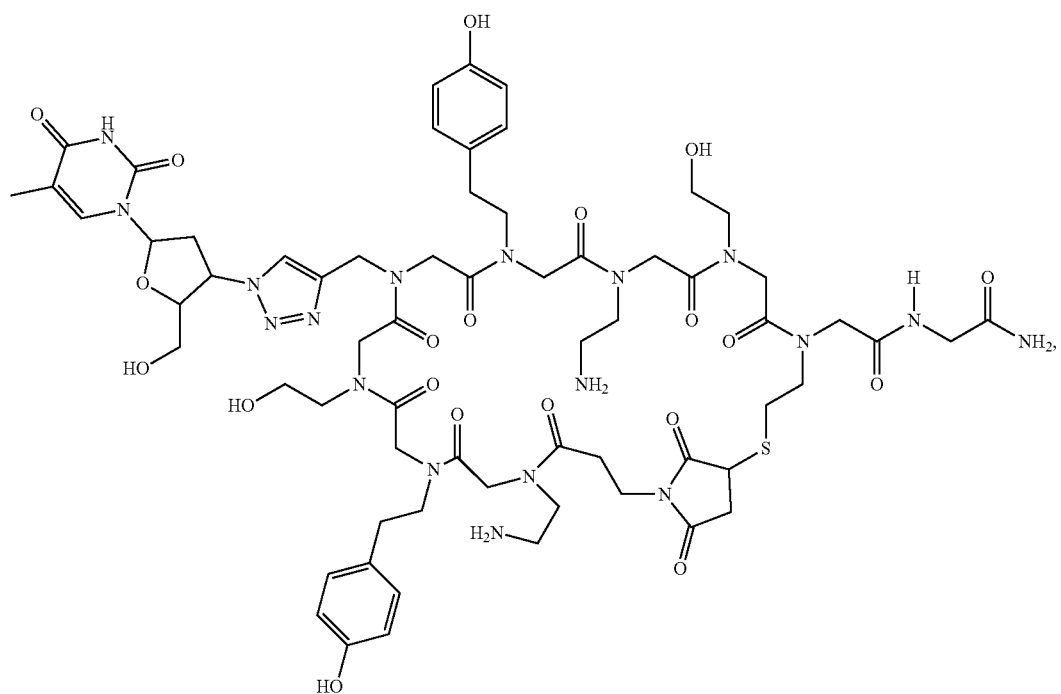

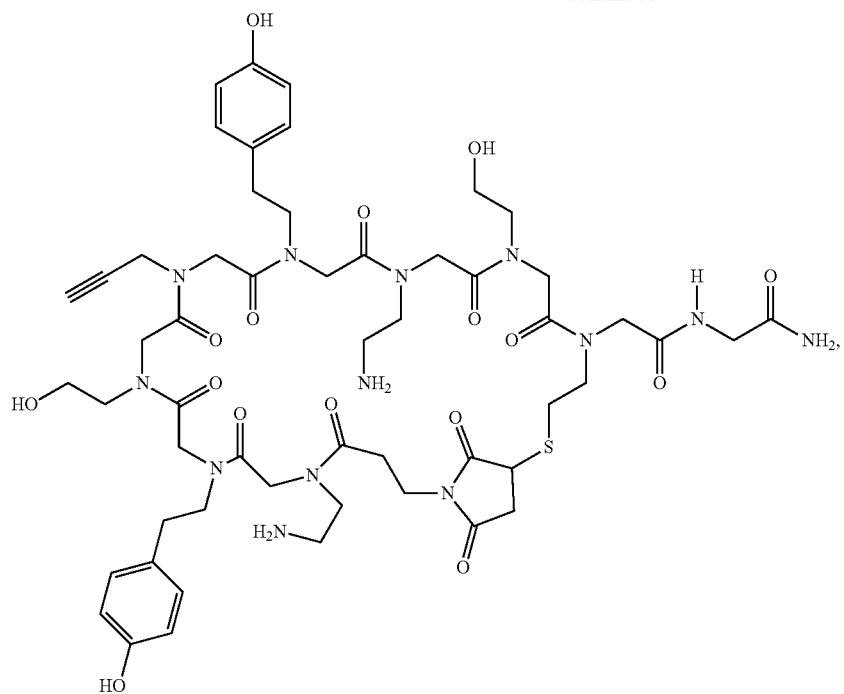
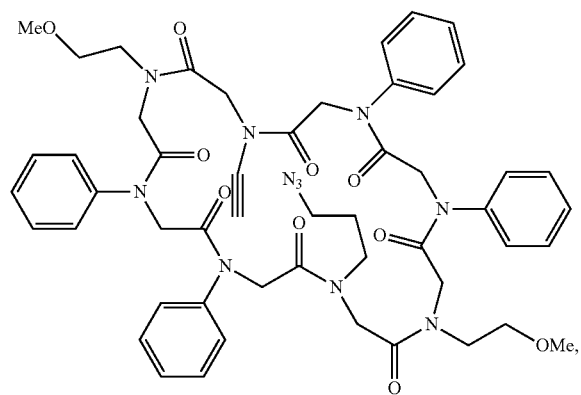
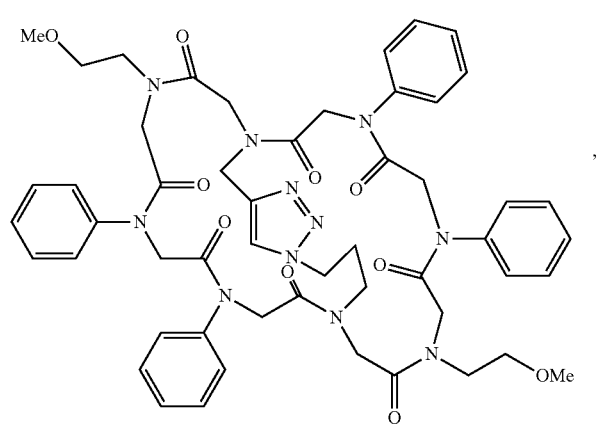
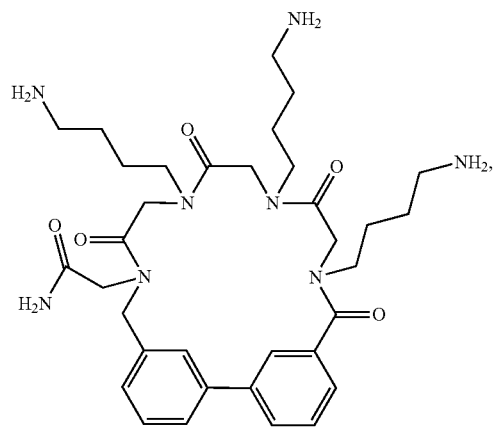

73
74
-continued
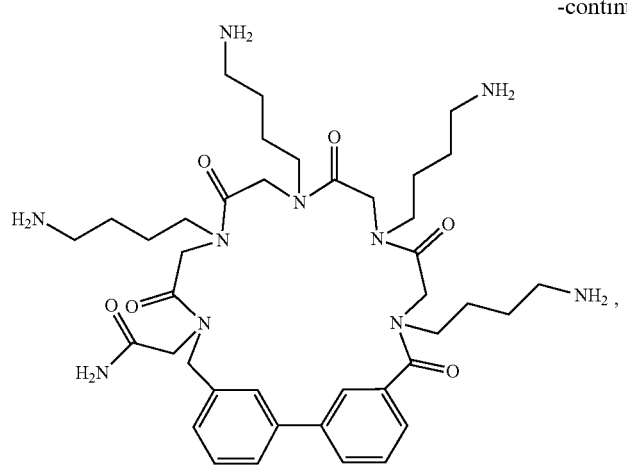
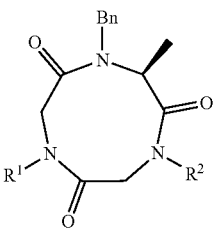
1, $R^1 = $ ⸺O⸺ ; $R^2 = $ ⸺,
2, $R^1 = $ ⸺ ; $R^2 = $ ⸺O⸺,
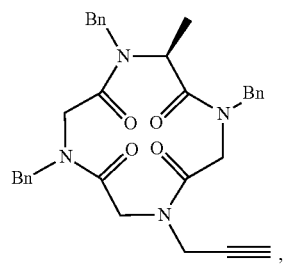
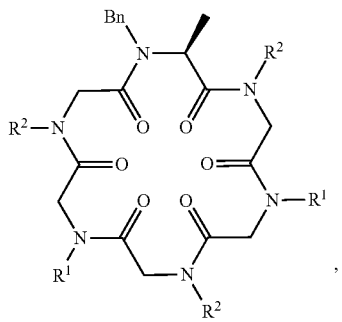
4, $R^1$; $R^2 = $ Bn
5, $R^1 = $ Bn; $R^2 = $ iPr
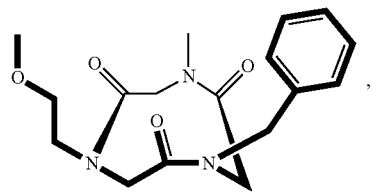
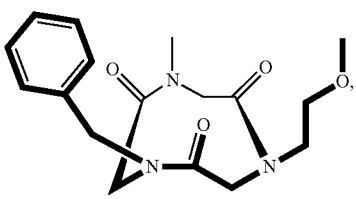
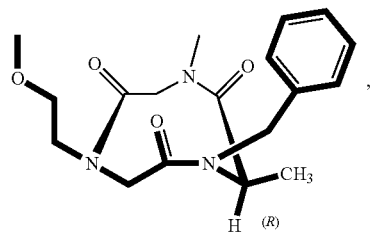
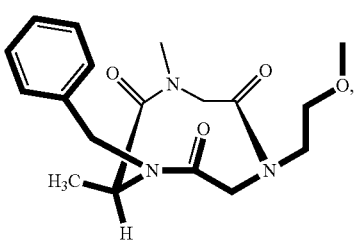
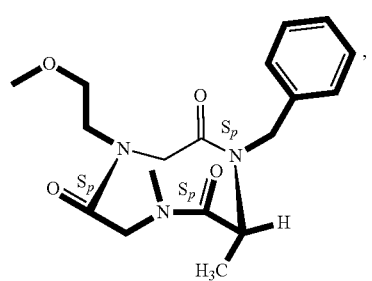
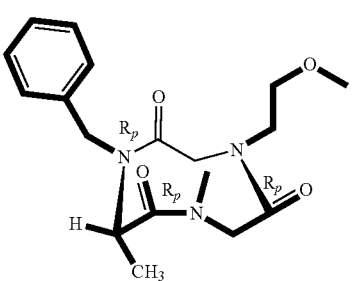

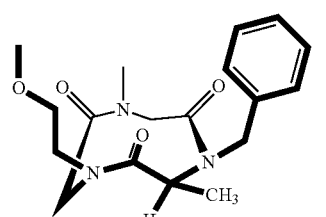
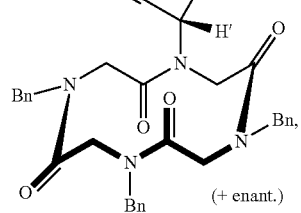
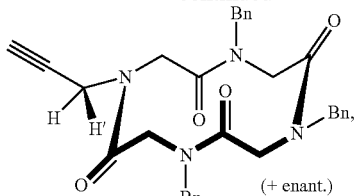
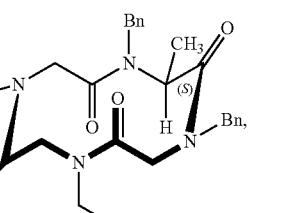
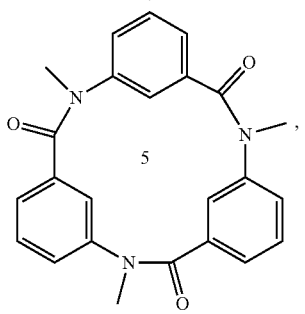
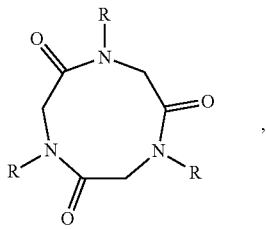
R =    1
R =    2
R =    3
R = 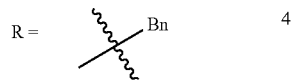   4
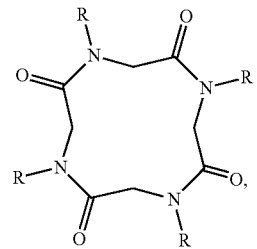
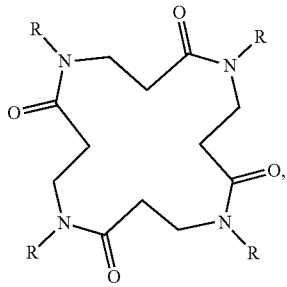
R =    7
R =    10
R =    8
R = 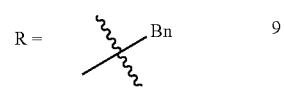   9

-continued
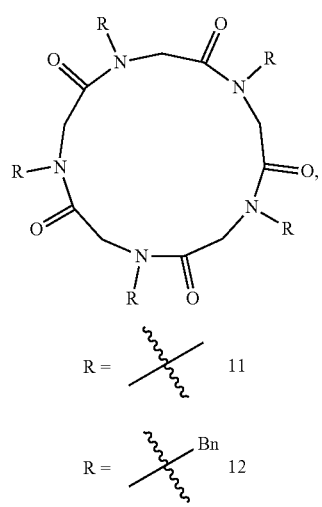
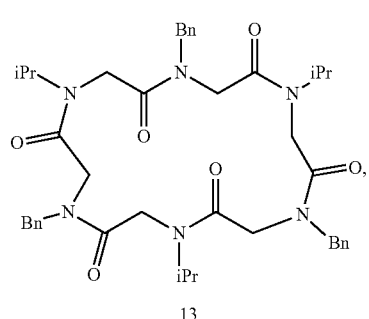
R = 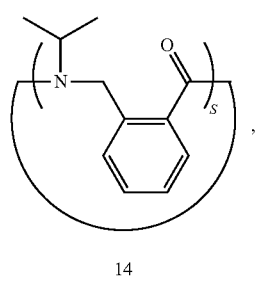 11, 12
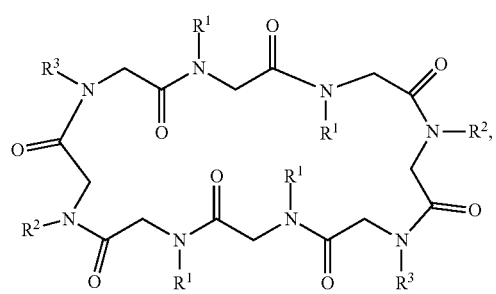
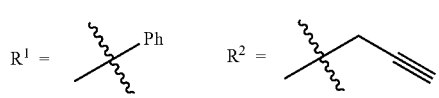

-continued
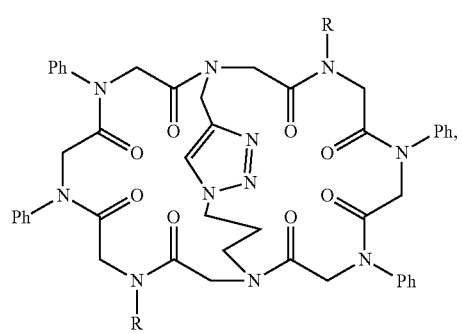
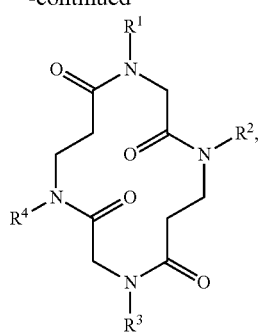
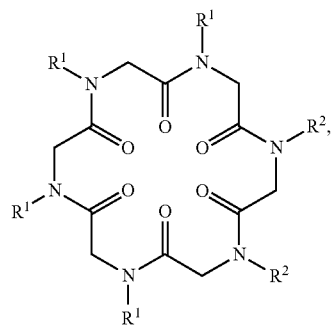
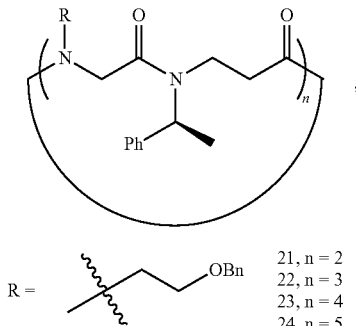
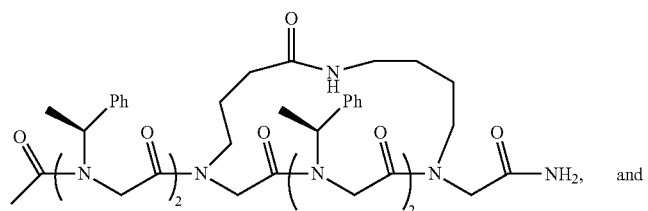
and
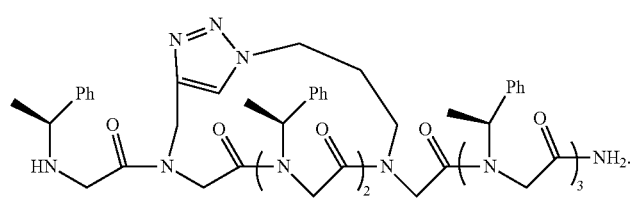

In one embodiment, the subscript n is 1. In another embodiment, the subscript n is 2. In another embodiment, the subscript n is 3. In another embodiment, n is 1, 2, 3, 4, 5, 6, 7, 8, 9, 10, 11, 12, 13, 14, 15, 16, 17, 18, 19, or 20.

In another embodiment, the oligomer is according to formula IIa, IIb, or IIc:

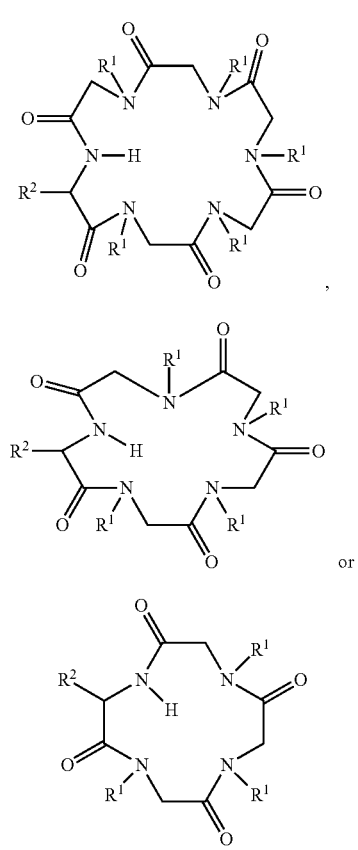

where the moiety —NH—CH($R^2$)—C(O)— is an amino acid residue; and $R^1$ is as described herein.

In various embodiments, a peptoid macrocycle of the present disclosure is a 4mer, 5mer, 6mer, 7mer, 8mer, 9mer, 10mer, 11mer, 12mer, 13mer, 14mer, 15mer, 16mer, 17mer, 18mer, 19mer, or 20mer. In an example, a 20mer is a 60 atom macrocycle.

In one embodiment, the moiety —NH—CH($R^2$)—C(O)— is an amino acid residue; and the amino acid is glycine, D-alanine, D-valine, D-leucine, D-isoleucine, D-tyrosine, D-proline, D-serine, D-glutamic acid, D-tryptophan, D-phenylalanine, D-methionine, D-arginine, D-histidine, D-glutamine, D-lysine, D-aspartic acid, D-threonine, D-cysteine, or D-asparagine.

In another embodiment, the moiety —NH—CH($R^2$)—C(O)— is an amino acid residue; and the amino acid is glycine, L-alanine, L-valine, L-leucine, L-isoleucine, L-tyrosine, L-proline, L-serine, L-glutamic acid, L-tryptophan, L-phenylalanine, L-methionine, L-arginine, or L-histidine.

In one particular embodiment, the amino acid is glycine. In another particular embodiment, the amino acid is D-alanine.

In one embodiment, the group —NH—CH($R^2$)—C(O)— is an amino acid residue; and $R^2$ is H or Me.

In one embodiment, each $R^1$ is independently substituted or unsubstituted alkyl, substituted or unsubstituted phenyl, substituted or unsubstituted naphthyl, substituted or unsubstituted benzyl, substituted or unsubstituted phenethyl, or substituted or unsubstituted heteroaryl.

In one embodiment, each $R^1$ is independently:
i) unsubstituted alkyl;
ii) Me, Et, n-Pr, i-Pr, n-Bu, sec-Bu, or i-Bu;
iii) alkyl substituted with one or more groups independently chosen from halo, hydroxy, amino, alkylamino, dialkylamino, acyl, acyloxy, substituted or unsubstituted phenyl, and alkoxy;
iv) alkyl substituted with one or more groups independently chosen from F, Cl, CN, OMe, O-i-Pr, 4-methoxyphenyl, 2-phenoxyphenyl, and $CF_3$;
v) unsubstituted phenyl;
vi) unsubstituted naphthyl;
vii) unsubstituted benzyl;
viii) unsubstituted phenethyl;
ix) phenyl substituted with one or more groups independently chosen from halo, alkyl, haloalkyl, CN, hydroxy, amino, alkylamino, dialkylamino, and alkoxy;
x) naphthyl substituted with one or more groups independently chosen from halo, alkyl, haloalkyl, CN, hydroxy, amino, alkylamino, dialkylamino, and alkoxy;
xi) benzyl substituted with one or more groups independently chosen from halo, alkyl, haloalkyl, CN, hydroxy, amino, alkylamino, dialkylamino, substituted or unsubstituted phenoxy, and alkoxy;
xii) phenethyl substituted with one or more groups independently chosen from halo, alkyl, haloalkyl, CN, hydroxy, amino, alkylamino, dialkylamino, and alkoxy;
xiii) phenyl substituted with one or more groups independently chosen from F, Cl, CN, OMe, and $CF_3$;
xiv) naphthyl substituted with one or more groups independently chosen from F, Cl, CN, OMe, and $CF_3$;
xv) benzyl substituted with one or more groups independently chosen from F, Cl, CN, OMe, OPh, and $CF_3$;
xvi) phenethyl substituted with one or more groups independently chosen from F, Cl, CN, OMe, and $CF_3$;
xvii) unsubstituted heteroaryl;
xviii) heteroaryl substituted with one or more groups independently chosen from halo, hydroxy, amino, alkylamino, dialkylamino, and alkoxy;
xix) heteroaryl substituted with one or more groups independently chosen from F, Cl, CN, OMe, and $CF_3$; or
any combinations thereof.

In one particular embodiment, heteroaryl is furanyl, thienyl, pyrrolyl, imidazolyl, pyridyl, pyrimidinyl, or the like.

In another particular embodiment, each $R^1$ is independently methoxyethyl, i-propoxyethyl, dimethoxyphenyl, fluorophenethyl, phenoxyphenethyl, methoxyphenethyl, or the like.

In another particular embodiment, each $R^1$ is independently 2-methoxyethyl, 2-i-propoxyethyl, 3,4-dimethoxyphenyl, 1-(4-fluorophen)ethyl, 1-(2-phenoxyphen)ethyl, 1-(4-methoxyphen)ethyl, 2-(2-phenoxyphen)ethyl, or 2-(4-methoxyphen)ethyl.

In another aspect, the disclosure provides a class of peptide-peptoid macrocycles that have a characteristic structure induced upon cyclization of the peptide-peptoid oligomer. Within this family, the molecules may be, for example, hexamers, synthesized using solid phase protocols to include a specific sequence of diverse side chain functional groups. The side chains have been selected using the computational modeling package Rosetta, to provide complementarity to the β-catenin surface.

In an embodiment, peptoid-peptide macrocycles of the present disclosure can be trimer, tetramer, pentamer, hexamer, heptamer, octamer, nonamer, decamer, undecamer, dodecamer, tridecamer, tetradecamer, pentadecamer, hexadecamer, heptadecamer, octadecamer, nonadecamer, or a dodecamer.

Figure 2:
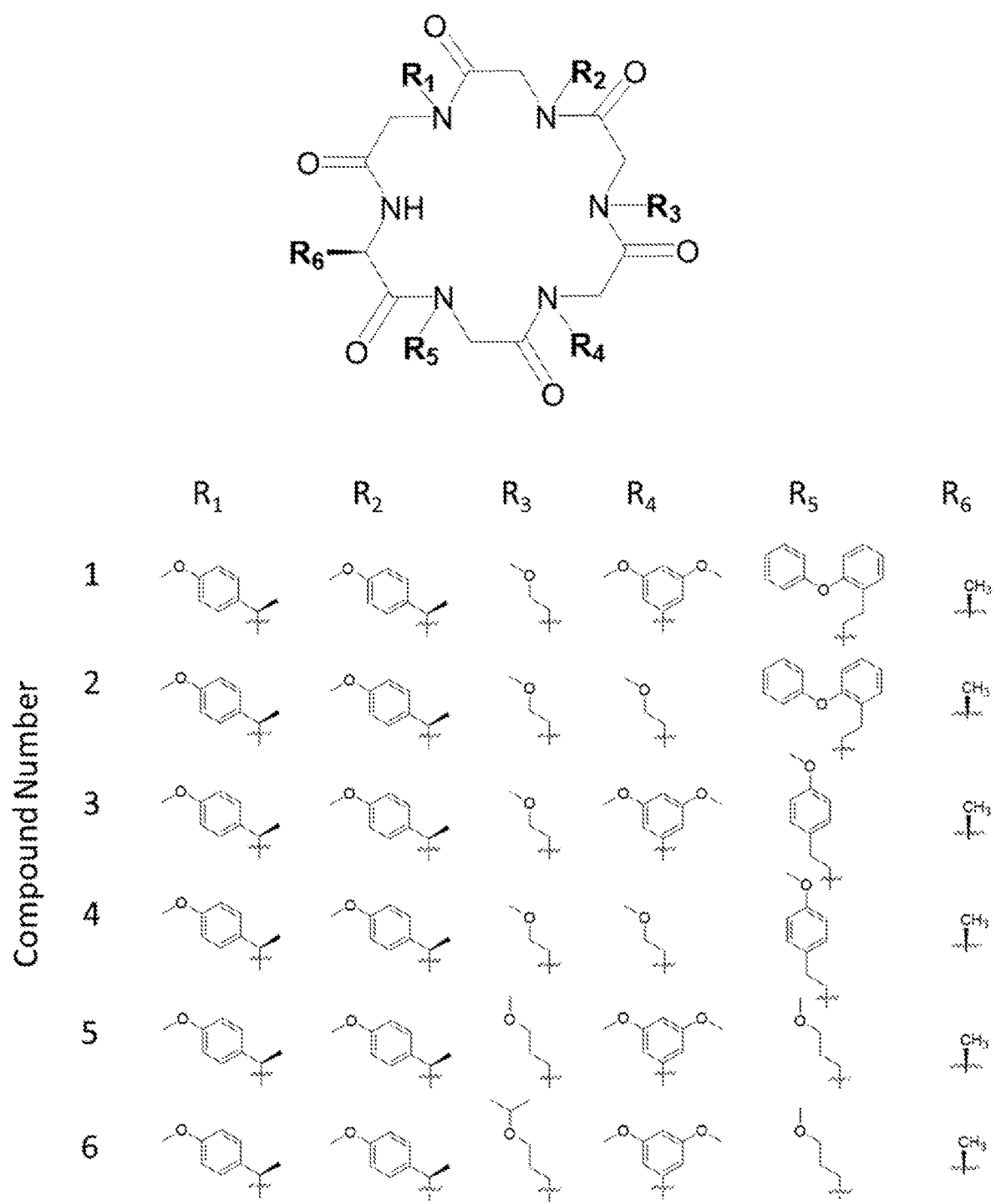
FIG. 2 shows non-limiting examples from the library of peptoid-peptide macrocycles synthesized that have been designed to antagonize the interaction between the proteins β-catenin and TCF. The particular side chain types at each of the 6 monomer positions is depicted for compounds 1 to 12. Note that most monomers are N-substituted glycine (peptoid) units, but the $R^6$ position corresponds to a canonical α-amino acid.
Figure 2:
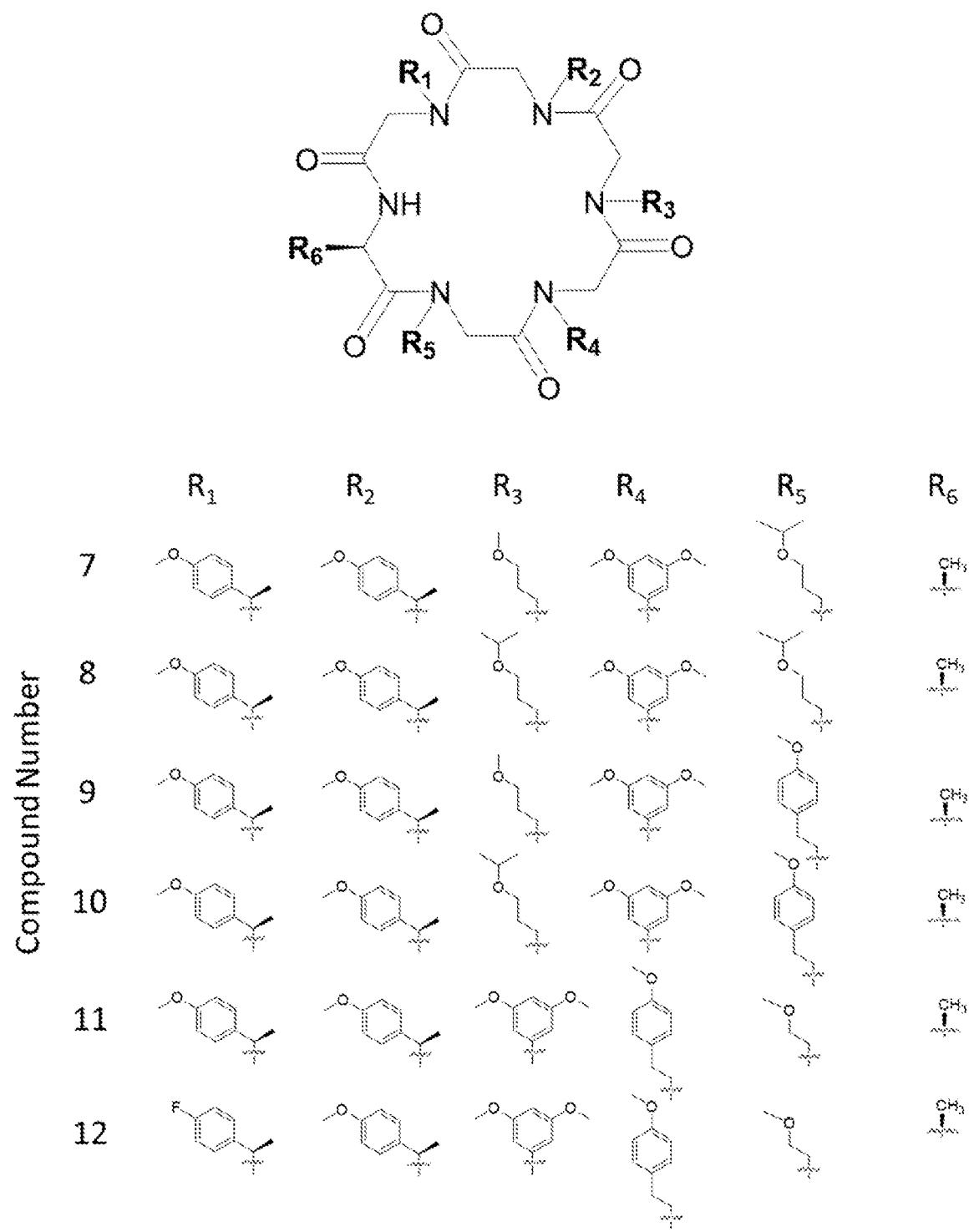

In a more particular embodiment, with respect to peptoid-peptide macrocycle, the peptoid-peptide macrocycle is selected from FIG. 2.

In certain aspects, the present disclosure provides prodrugs and derivatives of the macrocycles according to the formulae above. Prodrugs are derivatives of the macrocycles of the disclosure, which have metabolically cleavable groups and become by solvolysis or under physiological conditions the macrocycles of the disclosure, which are pharmaceutically active, in vivo. Such examples include, but are not limited to, choline ester derivatives and the like, N-alkylmorpholine esters and the like.

Other derivatives of the macrocycles of this disclosure have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives known in the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this disclosure are preferred prodrugs. In some cases it is desirable to prepare double ester type prodrugs such as (acyloxy)alkyl esters or ((alkoxycarbonyl)oxy)alkylesters. Preferred are the $C_1$-$C_8$ alkyl, $C_2$-$C_8$ alkenyl, $C_6$-$C_{10}$ aryl, $C_7$-$C_{12}$ substituted aryl, and $C_7$-$C_{12}$ arylalkyl esters of the compounds of the disclosure.

In one embodiment, the disclosure provides a pharmaceutical composition comprising a pharmaceutically acceptable carrier and a pharmaceutically effective amount of the peptoid-peptide macrocycles of the disclosure.

In one embodiment, the disclosure provides a pharmaceutical composition of the peptoid-peptide macrocycles of the disclosure, comprising a pharmaceutically acceptable carrier, and the carrier is a parenteral, oral, or topical carrier.

In one embodiment, the disclosure provides a method for preventing, treating, ameliorating, or managing a disease or condition which comprises administering to a patient in need of such prevention, treatment, amelioration or management, a prophylactically, or therapeutically effective amount of the pharmaceutical composition of the peptoid-peptide macrocycles of the disclosure.

Pharmaceutical Compositions

When employed as pharmaceuticals, the peptoid-peptide macrocycles described herein are typically administered in the form of a pharmaceutical composition. Such compositions can be prepared in a manner well known in the pharmaceutical art and comprise at least one active complex.

In various examples, the macrocycles of the present disclosure are administered in a pharmaceutically effective amount. The amount of the complex actually administered may be determined by a physician, in light of the relevant circumstances, including the condition to be treated, the chosen route of administration, the actual complex administered, the age, weight, and response of the individual patient, the severity of the patient's symptoms, and the like.

The pharmaceutical compositions of this disclosure may be administered by a variety of routes including by way of non-limiting example, oral, rectal, vaginal, transdermal, subcutaneous, intravenous, intramuscular, intrathecal, intranasal, and intrapulmonary (via, e.g., aerosolized delivery). Depending upon the intended route of delivery, the compounds of this disclosure are preferably formulated as, for example, injectable or oral compositions or as salves, as lotions or as patches, each of which are for transdermal administration.

The compositions for oral administration may take the form of bulk liquid solutions or suspensions, or bulk powders. In various examples, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions may be based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this disclosure.

The compounds of this disclosure can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pennsylvania, which is incorporated herein by reference.

The compounds of this disclosure can also be administered in sustained release forms or from sustained release drug delivery systems. A description of representative sustained release materials can be found in *Remington's Pharmaceutical Sciences.*

The following formulation examples illustrate representative pharmaceutical compositions that may be prepared in accordance with this disclosure. The present disclosure, however, is not limited to the following pharmaceutical compositions.

Formulation 1—Tablets

A compound of the disclosure may be admixed as a dry powder with a dry gelatin binder in, for example, an approximate 1:2 weight ratio. A minor amount of magnesium stearate is added as a lubricant. The mixture is formed into 240-270 mg tablets (80-90 mg of active compound per tablet) in a tablet press.

Formulation 2—Capsules

A compound of the disclosure may be admixed as a dry powder with a starch diluent in, for example, an approximate 1:1 weight ratio. The mixture is filled into 250 mg capsules (125 mg of active compound per capsule).

Formulation 3—Liquid

A compound of the disclosure (125 mg) may be, for example, admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Formulation 4—Tablets

A compound of the disclosure may be, for example, admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5—Injection

A compound of the disclosure may be, for example, dissolved or suspended in a buffered sterile saline injectable aqueous medium to a concentration of approximately 5 mg/mL.

Formulation 6—Topical

Stearyl alcohol (250 g) and a white petrolatum (250 g) may be melted at about 75° C. and then a mixture of a compound of the disclosure (50 g) methylparaben (0.25 g), propylparaben (0.15 g), sodium lauryl sulfate (10 g), and propylene glycol (120 g) dissolved in water (about 370 g) may be added and the resulting mixture is stirred until it congeals.

Methods of Treatment

The present macrocycles may be used as therapeutic agents for the treatment of conditions in mammals that are causally related or attributable to aberrant activity of the Wnt/wg signaling pathway. Accordingly, the compounds and pharmaceutical compositions of this disclosure find use as therapeutics for preventing and/or treating a variety of cancers, hyperproliferative conditions, and fibrotic diseases in mammals, including humans. Thus, and as stated earlier, the present disclosure includes within its scope, and extends to, the recited methods of treatment, as well as to the compounds for use in such methods, and for the preparation of medicaments useful for such methods.

In a method of treatment aspect, this disclosure provides a method of treating a mammal susceptible to or afflicted with a condition associated with cancer and/or a hyperproliferative disorder, which method comprises administering an effective amount of one or more of the pharmaceutical compositions just described.

In yet another method of treatment aspect, this disclosure provides a method of treating a mammal susceptible to or afflicted with a condition that gives rise to increased cellular proliferation or a transformed phenotype, or that relates to dysregulation of Wnt/wg signaling. The present macrocycles may be used as anti-proliferative agents that reduce proliferative levels (potentially to normal levels for a particular cell type), and/or anti-transformed phenotype agents that restore, at least in part, normal phenotypic properties of a particular cell type. Accordingly, the present macrocycles have use for the treatment of cancers and hyperproliferative disorders relating to aberrant Wnt/wg signaling.

In additional method of treatment aspects, this disclosure provides methods of treating a mammal susceptible to or afflicted with a cancer causally related or attributable to aberrant activity of the Wnt/wg signaling pathway. Such cancers include, without limitation, those of the prostate cancer, colon cancer, rectal cancer, breast cancer, skin cancer (e.g., melanoma), liver cancer (e.g., hepatocellular cancer and hepatoblastoma), head and neck cancer, lung cancer (e.g., non-small cell lung cancer), gastric cancer, mesothelioma, Barrett's esophagus, synovial sarcoma, cervical cancer, endometrial ovarian cancer, Wilm's tumor, bladder cancer, and leukemia. Such methods comprise administering an effective condition-treating or condition-preventing amount of one or more of the pharmaceutical compositions just described.

With respect to prostate cancer, for example, macrocycles and compositions thereof and methods described herein are also envisioned as useful for targeting cancerous prostate cells that remain following radical prostatectomy, including, for example, micrometastases and thus, are useful for treating prostate cancer patients following surgical intervention. In addition, macrocycles and compositions thereof and methods described herein are envisioned as being useful in advance of surgical intervention to delay or prevent the need for surgery. For such purposes, direct delivery of the macrocycles or compositions thereof to the prostate tumor or in the vicinity of the tumor is envisioned as a particular delivery mode suitable for such an application.

Also envisioned herein are combination therapies that comprise administration of one or more of the macrocycles described herein, or a composition thereof, in conjunction with therapeutic regimens (e.g., local and/or systemic therapeutic modalities) implemented for treating patients afflicted with diseases or conditions that are causally related to the aberrant activity of the Wnt pathway in vivo. Such diseases include, without limitation, pulmonary fibrosis and cancers, including: without limitation, prostate cancer, colon cancer, rectal cancer, breast cancer, skin cancer (e.g., melanoma), liver cancer (e.g., hepatocellular cancer and hepatoblastoma), head and neck cancer, lung cancer (e.g., non-small cell lung cancer), gastric cancer, mesothelioma, Barrett's esophagus, synovial sarcoma, cervical cancer, endometrial ovarian cancer, Wilm's tumor, bladder cancer, and leukemia.

Combination therapies may boost the therapeutic activity of each of the therapeutic modalities with the potential for synergistic therapeutic benefit. Combination therapy, furthermore, has the potential to improve therapeutic benefit with no significant increase in morbidity relative to that typically achieved using the individual therapeutic modalities (monotherapies) separately. Under some circumstances, the doses of each of the individual therapeutic modalities can be reduced, which may result in an overall decrease in morbidity when combination therapy is implemented.

It will be appreciated that combination therapies may involve administration of one or more of the macrocycles described herein, or a composition thereof, at the same time, before, and/or after a second therapeutic modality of the combination therapy. The timing of administration of the, e.g., first and second therapeutic modalities of a combination therapy may be determined based on the experience of the attending physician and the manner in which therapeutic modalities known in the art are typically administered.

In a particular aspect, a combination therapy comprises administration of one or more of the macrocycles described herein, or a composition thereof, in conjunction with a systemic therapeutic modality, such as, for example, one or more of a systemic inhibitor of immune system down regulation, such as anti-CTLA-4 (including but not limited to ipilimumab and tremelimumab), PD-1, and PD-L1 antibodies.

In another aspect, combination therapy may comprise administration of one or more of the macrocycles described herein, or a composition thereof, in conjunction with one or more of a systemic immune upregulating agent, including: non-specific cytokines, such as interleukin-1, -2, or -6 (IL-1, IL-2, or IL-6) and aldesleukin; interferon-alpha or gamma (IFN-α and IFN-γ), interferon alfa-2b and PEGylated interferon (including PEGylated interferon alfa-2a and PEGylated interferon alfa-2b); granulocyte macrophage colony stimulating factor (GM-CSF, molgramostim or sargramostim); dendritic cell vaccines and other allogeneic or autologous therapeutic cancer vaccines, including intralesional vaccines containing an oncolytic herpes virus encoding GM-CSF (ONCOVEX®) or a plasmid encoding human leukocyte antigen-B7 and beta-2 microglobulin agent designed to express allogeneic MHC class I antigens (ALLOVECTIN-7®); and antibodies against specific tumor antigens.

In yet another aspect, combination therapy may comprise administration of one or more of the macrocycles described herein, or a composition thereof, in conjunction with one or more systemic targeted therapy agent, including: drugs that target protein kinases and the receptors that activate them, including but not limited to afatinib (BIBW 2992), bevacizumab, cetuximab, dasatinib, E7080, erlotinib, gefitinib, imatinib, lapatinib, nilotinib, panitumumab, pazopanib, pegaptanib, ranibizumab, sorafenib, sunitinib, trastuzumab and vandetanib; serine/threonine-selective protein kinase inhibitors, including but not limited to those targeting the B-Raf/MEK ERK pathway, such as vemurafenib (also known as PLX4032, RG7204 or RO5185426), GSK2118436 and GSK1120212; aromatase inhibitors, including but not limited to aminoglutethimide, anastrozole, exemestane, fadrozole, formestane, letrozole, testolactone and vorozole; estrogen receptor antagonists, including but not limited to lasofoxifene, raloxifene, tamoxifen and toremifene; COX-2 inhibitors, including but not limited to celecoxib, valdecoxib and rofecoxib; angiogenesis blockers, including IFN-α, IL-12, suramin, and thrombospondin (including thrombospondin 1, ABT-510 and ABT-898); androgen receptor antagonists, including, but not limited to, bicalutamide; and immune cell therapy, including but not limited to adoptive T-cell transfer and autologous immune cell therapy.

The aforementioned systemic therapeutic modalities are known in the art and are described in, for example, U.S. 2015/0290318, the entire content of which is incorporated herein by reference.

In a further aspect, a combination therapy comprises administration of one or more of the macrocycles described herein, or a composition thereof, in conjunction with a local therapeutic modality, such as, for example, a local immunomodulative therapy: including, but not limited to, intralesional (IL) chemoablation using an IL chemoablative agent consisting primarily of rose bengal (4,5,6,7-tetrachloro-2',4',5',7'-tetraiodofluorescein) or another halogenated xanthene, including erythrosin B, phloxine B, 4,5,6,7-tetrabromo-2',4',5',7'-tetraiodofluorescein, 2',4,5,6,7-pentachloro-4',5',7'-triiodofluorescein, 4,4',5,6,7-pentachloro-2',5',7'-triiodofluorescein, 2',4,5,6,7,7'-hexachloro-4',5'-diiodofluorescein, 4,4',5,5',6,7-hexachloro-2',7'-diiodofluorescein, 2',4,5,5',6,7-hexachloro-4',7'-diiodofluorescein, 4,5,6,7-tetrachloro-2',4',5'-triiodofluorescein, 4,5,6,7-tetrachloro-2',4',7'-triiodofluorescein, 4,5,6,7-tetrabromo-2',4',5'-triiodofluorescein, and 4,5,6,7-tetrabromo-2',4',7'-triiodofluorescein in an appropriate pharmaceutical composition, including a 0.1% (w/v) or higher concentration aqueous solution of rose bengal (i.e., PV-10) or equivalent solution of another halogenated xanthene or mixtures thereof. A physiologically acceptable salt of the halogenated xanthene may be used in this composition. The aforementioned local immunomodulative therapies are known in the art and are described in, for example, U.S. 2015/0290318 and U.S. application Ser. No. 12/315,781, the entire content of each of which is incorporated herein by reference.

In a more particular aspect, a combination therapy comprises administration of one or more of the macrocycles described herein, or a composition thereof, in conjunction with intralesional (IL) chemoablation with PV-10 or another halogenated xanthene agent. As described in, for example, U.S. 2015/0290318 (the entire content of which is incorporated herein by reference), IL chemoablation using a specific class of agent (for example certain formulations of certain halogenated xanthenes, as exemplified by a 10% (w/v) solution of rose bengal disodium in saline, termed "PV-10") can elicit not only highly specific ablation of the injected lesion but also an antitumor immune response ("bystander effect") that augments local efficacy in the injected tumor and leads to spontaneous regression of uninjected tumors. PV-10 is, for example, undergoing clinical testing for treatment of metastatic melanoma, breast carcinoma and hepatocellular carcinoma. IL chemoablation can lead to rapid reduction in tumor burden, thereby reducing the potential for tumor-induced immune suppression and potentially minimizing the extent and severity of the disease. Chemoablation of entire tumors or substantially all of the tumors, and especially chemoablation of multiple tumors, enhances exposure of the patient's immune system to distinct clonal subpopulations of tumor cells that may be present, and thus maximizes overall immune response to the tumor.

The effects of combination therapy can be heightened by repeated administration. Since IL chemoablation is well suited to repeat treatment, continued therapeutic intervention by ongoing administration of the macrocycles described herein, or a composition thereof, alongside repeated IL chemoablation is envisioned. The timing of administration may be varied and combination therapy may be performed with concurrent administration of either therapy, or delayed administration of one or another of the therapies.

Under circumstances where a disease is rapidly proliferating, widely disseminated, or presents in a form difficult to infiltrate fully with the IL chemoablative agent, use of additional complementary therapeutic modalities may offer additive or synergistic benefit, particularly when they promote immunologic stimulation (i.e., immunodulation). Complementary immunomodulative therapies may be used to advantage to promote additive or synergistic immunologic interactions that allow one or multiple therapies to be used at reduced doses relative to those used when administered individually as monotherapies, while retaining high efficacy and potentially reducing undesirable adverse effects. Exemplary immunomodulative therapies elicit immune system upregulation or counter tumor-induced immune system down regulation.

Monotherapy dose schedules may be set by determining the maximum tolerated dose (MTD) in early-stage clinical trials. The MTD (or a close variation thereof) is then applied to later-stage clinical trials that optimize efficacy and further assess issues pertaining to safety. Exemplary dosing schedules for a number of systemic agents that may be combined with administration of one or more of the macrocycles described herein, or a composition thereof, are provided in Table 1.

TABLE 1

Example systemic immunomodulatory or targeted anticancer agents

| Systemic Agent | Typical Dose Schedule |
| --- | --- |
| Ipilimumab | 3 mg/kg q21d for 4 treatments |
| Tremelimumab | 15 mg/kg q3m |
| Aldesleukin | 600,000 IU/kg q8h (up to 14 doses before 9 day rest and repeat; rest at least 7 wks before repeat of course) |
| interferon alfa-2b | 20 million IU/m$^2$ 5 times per week for 4 weeks (induction phase) followed by 10 million IU/m$^2$ three times per week (maintenance phase) |
| pegylated interferon | 6 μg/kg qwk for eight weeks (induction phase) followed by 3 μg/kg qwk (maintenance phase) |
| Oncovex ® | 4 mL IL at $10^8$ pfu/mL |
| GM-CSF | 125 μg/m$^2$ daily for 14 wks followed by 14 days rest |
| Allovectin-7 ® | 2 mg IL qwk for 6 wks |
| Afatinib | 20-50 mg daily |
| Bevacizumab | 5-15 mg/kg q14d-q21d |
| Cetuximab | 400 mg/m$^2$ followed by weekly maintenance at 250 mg/m$^2$ |
| Dasatinib | 100 mg daily |
| Erlotinib | 100-150 mg daily |
| Gefitinib | 250 mg daily |
| Imatinib | 400-600 mg daily (increased to twice daily if well tolerated or disease progresses) |
| Lapatinib | 1250 mg daily for 21 day cycle |
| Nilotinib | 400 mg twice daily |
| Panitumumab | 6 mg/kg q14d |
| Pazopanib | 800 mg daily |
| Pegaptanib | 0.3 mg q6wks |
| Ranibizumab | 0.5 mg q4wks |
| Sorafenib | 400 mg twice daily |
| Sunitinib | 50 mg daily for 4 weeks followed by 2 week recovery |
| Trastuzumab | 4 mg/kg followed by weekly maintenance at 2 mg/kg |
| Vandetanib | 200-300 mg daily |
| Vemurafenib (PLX4032) | 960 mg twice daily |
| GSK2118436 [a] | 150 mg twice daily |
| GSK1120212 [a] | 2 mg daily |
| aminoglutethimide | 250 mg q6h |
| Anastrozole | 1 mg daily |
| Exemestane | 25 mg daily |
| Fadrozole | 1 mg twice daily |
| Formestane | 250 mg daily |
| Letrozole | 2.5 mg daily |
| Vorozole | 2.5 mg daily |
| Raloxifene | 60 mg daily |
| Tamoxifen | 20-40 mg daily |
| Toremifene | 60 mg daily |
| Celecoxib | 200-400 mg twice daily |
| Rofecoxib | 20-25 mg daily |
| Suramin | 1 g qwk |
| thrombospondin (ABT-510 [a]) | 20 mg daily to 100 mg twice daily |

[a] Proprietary code name for drug under development for which no nonproprietary name is currently available.

Due to additive or synergistic effects of the monotherapies used in combination, the combination therapies and methods for treatment described herein will generally permit administration of a systemic agent at a level at or below the typical dose schedule for the systemic agent when used as a monotherapy (as described in Table 1). This may also apply to dosing parameters for the macrocycles described herein or a composition thereof. Lower doses of the macrocycles described herein, or a composition thereof, may confer benefit when used in combination with either systemic or a local therapeutic modality, such as, for example, a local immunomodulative therapy.

In an example, combination therapies that comprise administration of one or more of the macrocycles described herein, or a composition thereof, in conjunction with therapeutic regimens directed to promoting immune responses are envisioned. Such therapeutic regimens may be directed to promoting immune responses systemically and/or in a localized manner. As indicated herein above, effective systemic immunotherapeutic approaches have been developed and implemented for the treatment of a variety of cancers, including melanoma, lung cancer, and prostate cancer. These approaches include blockade of immune-inhibitory receptors on activated T cells. Monoclonal antibodies against CTLA-4, PD-1, and PD-L1, for example, have been used to advantage to promote immune responses. See, for example, Kaufman et al. (2013, Nature Rev Clin Oncol 10:588); Mellman et al. (2011, Nature 480:480); Wolchok et al. (2013, N Engl J Med 369:122); Topalian et al. (2014, J Clin Oncol 32:1020); and Hodi et al. (2010, N Engl J Med 363:711), the entire content of each of which is incorporated herein by reference. Combination therapy comprising inhibitors of Wnt/β-catenin pathways and antibodies against CTLA-4, PD-1, and/or PD-L1 have been proposed as having potential for the treatment of, for example, melanoma. Without being bound by theory, it is thought that inhibitors of Wnt/β-catenin pathways enhance the efficacy of the immunotherapy. See, for example, Spranger et al. (2015, Nature 523:231); Hanks et al. (2015, J Clin Oncol 33:suppl. abstr 3054); Sweis et al. (2015, J Clin Oncol 33:suppl. abstr 4511); Spranger et al. (2015, J Clin Oncol 33:suppl. abstr 9014), the entire content of which each of which is incorporated herein by reference. Accordingly, combination therapy comprising administration of one or more of the macrocycles described herein, or a composition thereof, in conjunction with at least one of antibodies against CTLA-4, PD-1, and/or PD-L1 is envisioned herein.

Various types of cancers are listed herein and are envisioned for treatment using the combination therapies described herein. Such combination therapies comprise administration of one or more of the macrocycles described herein, or a composition thereof, in conjunction with a therapeutic regimen used for the treatment of a cancer, such as those understood in the art and listed, for example, herein below.

Breast Cancer

Cancer drugs approved by the Food and Drug Administration (FDA) for treating breast cancer include, without limitation: Abitrexate (Methotrexate), Abraxane (Paclitaxel Albumin-stabilized Nanoparticle Formulation) Ado-Trastuzumab Emtansine, Adrucil (Fluorouracil), Afinitor (Everolimus), Anastrozole, Aredia (Pamidronate Disodium), Arimidex (Anastrozole), Aromasin (Exemestane), Capecitabine, Clafen (Cyclophosphamide), Cyclophosphamide, Cytoxan (Cyclophosphamide), Docetaxel, Doxorubicin Hydrochloride, Efudex (Fluorouracil), Ellence (Epirubicin Hydrochloride), Epirubicin Hydrochloride, Eribulin Mesylate, Everolimus, Exemestane, 5-FU (Fluorouracil), Fareston (Toremifene), Faslodex (Fulvestrant), Femara (Letrozole), Fluoroplex (Fluorouracil), Fluorouracil, Folex (Methotrexate), Folex PFS (Methotrexate), Fulvestrant, Gemcitabine Hydrochloride, Gemzar (Gemcitabine Hydrochloride), Goserelin Acetate, Halaven (Eribulin Mesylate), Herceptin (Trastuzumab), Ibrance (Palbociclib), Ixabepilone, Ixempra (Ixabepilone), Kadcyla (Ado-Trastuzumab Emtansine), Lapatinib Ditosylate, Letrozole, Megace (Megestrol Acetate), Megestrol Acetate, Methotrexate, Methotrexate LPF (Methotrexate), Mexate (Methotrexate), Mexate-AQ (Methotrexate), Neosar (Cyclophosphamide), Nolvadex (Tamoxifen Citrate), Paclitaxel, Paclitaxel Albumin-stabilized Nanoparticle Formulation, Palbociclib, Pamidronate Disodium, Perjeta (Pertuzumab), Pertuzumab, Tamoxifen Citrate, Taxol (Paclitaxel), Taxotere (Docetaxel), Thiotepa, Toremifene, Trastuzumab, Tykerb (Lapatinib Ditosylate), Velban (Vinblastine Sulfate), Velsar (Vinblastine Sulfate), Vinblastine Sulfate, Xeloda (Capecitabine), and Zoladex (Goserelin Acetate).

Drug combinations used for treating breast include, without limitation: AC: Doxorubicin Hydrochloride (Adriamycin) (A); and Cyclophosphamide (C); AC-T: Doxorubicin Hydrochloride (Adriamycin) (A); Cyclophosphamide (C); Paclitaxel (Taxol) (T); CAF: Cyclophosphamide (C); Doxorubicin Hydrochloride (Adriamycin) (A); and Fluorouracil (F); CMF: Cyclophosphamide (C); Methotrexate (M); and Fluorouracil (F); FEC: Fluorouracil (F); Epirubicin Hydrochloride (E); Cyclophosphamide (C); TAC: Docetaxel (Taxotere) (T); Doxorubicin Hydrochloride (Adriamycin) (A); and Cyclophosphamide (C).

Additional information pertaining to monotherapies and drug combinations used for treating breast cancer are known in the art and can be accessed via a variety websites on the worldwide web, including those provided by the National Cancer Institute.

Prostate Cancer

Cancer drugs approved by the FDA for treating prostate cancer include, without limitation: Abiraterone Acetate; Bicalutamide; Cabazitaxel; Casodex (Bicalutamide); Degarelix; Docetaxel; Enzalutamide; Goserelin Acetate; Jevtana (Cabazitaxel); Leuprolide Acetate; Lupron (Leuprolide Acetate); Lupron Depot (Leuprolide Acetate); Lupron Depot-3 Month (Leuprolide Acetate); Lupron Depot-4 Month (Leuprolide Acetate); Lupron Depot-Ped (Leuprolide Acetate); Mitoxantrone Hydrochloride; Prednisone; Provenge (Sipuleucel-T); Radium 223 Dichloride; Sipuleucel-T; Taxotere (Docetaxel); Viadur (Leuprolide Acetate); Xofigo (Radium 223 Dichloride); Xtandi (Enzalutamide); Zoladex (Goserelin Acetate); and Zytiga (Abiraterone Acetate).

Additional information pertaining to monotherapies and drug combinations used for treating prostate cancer are known in the art and can be accessed via a variety websites on the worldwide web, including those provided by the National Cancer Institute.

Colon Cancer

Cancer drugs approved by the FDA for treating colon cancer include, without limitation: Adrucil (Fluorouracil); Avastin (Bevacizumab); Bevacizumab; Camptosar (Irinotecan Hydrochloride); Capecitabine; Cetuximab; Cyramza (Ramucirumab); Efudex (Fluorouracil); Eloxatin (Oxaliplatin); Erbitux (Cetuximab); 5-FU (Fluorouracil); Fluoroplex (Fluorouracil); Fluorouracil; Irinotecan Hydrochloride; Leucovorin Calcium; Lonsurf (Trifluridine and Tipiracil Hydrochloride); Oxaliplatin; Panitumumab; Ramucirumab; Regorafenib; Stivarga (Regorafenib); Trifluridine and Tipiracil Hydrochloride; Vectibix (Panitumumab); Wellcovorin (Leucovorin Calcium); Xeloda (Capecitabine); Zaltrap (Ziv-Aflibercept); and Ziv-Aflibercept.

Drug combinations used for treating colon cancer include, without limitation: CAPOX: Capecitabine (CAP); Oxaliplatin (OX); FOLFIRI: Leucovorin Calcium (Folinic Acid) (FOL); Fluorouracil (F); Irinotecan Hydrochloride (IRI); FOLFIRI-BEVACIZUMAB: Leucovorin Calcium (Folinic Acid) (FOL); Fluorouracil (F); Irinotecan Hydrochloride (IRI); Bevacizumab; FOLFIRI-CETUXIMAB: Leucovorin Calcium (Folinic Acid) (FOL); Fluorouracil (F); Irinotecan Hydrochloride (IRI); Cetuximab; FOLFOX: Leucovorin Calcium (Folinic Acid) (FOL); Fluorouracil (F); Oxaliplatin (OX); FU-LV: Fluorouracil (FU); Leucovorin Calcium (LV); and XELIRI: Capecitabine (Xeloda) (XEL); Irinotecan Hydrochloride (IRI); XELOX: Capecitabine (Xeloda) (XEL); Oxaliplatin (OX).

Rectal Cancer

Cancer drugs approved by the FDA for treating rectal cancer include, without limitation: Adrucil (Fluorouracil); Avastin (Bevacizumab); Bevacizumab; Camptosar (Irinotecan Hydrochloride); Capecitabine; Cetuximab; Cyramza (Ramucirumab); Efudex (Fluorouracil); Eloxatin (Oxaliplatin); Erbitux (Cetuximab); 5-FU (Fluorouracil); Fluoroplex (Fluorouracil); Fluorouracil; Irinotecan Hydrochloride; Leucovorin Calcium; Lonsurf (Trifluridine and Tipiracil Hydrochloride); Oxaliplatin; Panitumumab; Ramucirumab; Regorafenib; Stivarga (Regorafenib); Trifluridine and Tipiracil Hydrochloride; Vectibix (Panitumumab); Wellcovorin (Leucovorin Calcium); Xeloda (Capecitabine); Zaltrap (Ziv-Aflibercept); and Ziv-Aflibercept.

Drug combinations used for treating rectal cancer include, without limitation: CAPOX: Capecitabine (CAP); Oxaliplatin (OX); FOLFIRI: Leucovorin Calcium (Folinic Acid) (FOL); Fluorouracil (F); Irinotecan Hydrochloride (IRI); FOLFIRI-BEVACIZUMAB: Leucovorin Calcium (Folinic Acid) (FOL); Fluorouracil (F); Irinotecan Hydrochloride (IRI); Bevacizumab; FOLFIRI-CETUXIMAB: Leucovorin Calcium (Folinic Acid) (FOL); Fluorouracil (F); Irinotecan Hydrochloride (IRI); Cetuximab; FOLFOX: Leucovorin Calcium (Folinic Acid) (FOL); Fluorouracil (F); Oxaliplatin (OX); FU-LV: Fluorouracil (FU); Leucovorin Calcium (LV); XELIRI: Capecitabine (Xeloda) (XEL); Irinotecan Hydrochloride (IRI); XELOX: Capecitabine (Xeloda) (XEL); and Oxaliplatin (OX).

Gastroenteropancreatic Neuroendocrine Tumors

Cancer drugs approved by the FDA for treating gastroenteropancreatic neuroendocrine tumors include, without limitation: Lanreotide Acetate; and Somatuline Depot (Lanreotide Acetate).

Additional information pertaining to monotherapies and drug combinations used for treating colon cancer, rectal cancer, and gastrenteropancreatic neuroendocrine tumors are known in the art and can be accessed via a variety websites on the worldwide web, including those provided by the National Cancer Institute.

Ovarian Cancer, Fallopian Tube Cancer, and Primary Peritoneal Cancer

Cancer drugs approved by the FDA for treating ovarian cancer, fallopian tube cancer, and primary peritoneal cancer include, without limitation: Avastin (Bevacizumab); Bevacizumab; Carboplatin; Clafen; (Cyclophosphamide); Cisplatin; Cyclophosphamide; Cytoxan (Cyclophosphamide); Doxorubicin Hydrochloride; Dox-SL (Doxorubicin Hydrochloride Liposome); DOXIL (Doxorubicin Hydrochloride Liposome); Doxorubicin Hydrochloride Liposome; Evacet (Doxorubicin Hydrochloride Liposome); Gemcitabine Hydrochloride; Gemzar (Gemcitabine Hydrochloride); Hycamtin (Topotecan Hydrochloride); LipoDox (Doxorubicin Hydrochloride Liposome); Lynparza (Olaparib); Neosar (Cyclophosphamide); Olaparib; Paclitaxel; Paraplat (Carboplatin); Paraplatin (Carboplatin); Platinol (Cisplatin); Platinol-AQ (Cisplatin); Taxol (Paclitaxel); Thiotepa; and Topotecan Hydrochloride.

Drug combinations used for treating ovarian cancer, fallopian tube cancer, and primary peritoneal cancer include, without limitation: BEP: Bleomycin (B); Etoposide (E); Cisplatin (Platinol) (P); CARBOPLATIN-TAXOL: Carboplatin (C); Paclitaxel (Taxol); GEMCITABINE-CISPLATIN: Gemcitabine Hydrochloride, Cisplatin; and VeIP: Vinblastine Sulfate (Velban) (Ve); Ifosfamide (I); Cisplatin (Platinol).

Liver Cancer

Cancer drugs approved by the FDA for treating liver cancer include, without limitation: Nexavar (Sorafenib Tosylate); and Sorafenib Tosylate.

Head and Neck Cancer

Cancer drugs approved by the FDA for treating cancer that arises in the head or neck region (in the nasal cavity, sinuses, lips, mouth, salivary glands, throat, or larynx [voice box]) include, without limitation: Abitrexate (Methotrexate); Adrucil (Fluorouracil); Blenoxane (Bleomycin); Bleomycin; Cetuximab; Cisplatin; Docetaxel; Efudex (Fluorouracil); Erbitux (Cetuximab); 5-FU (Fluorouracil); Fluoroplex (Fluorouracil); Fluorouracil; Folex (Methotrexate); Folex PFS (Methotrexate); Methotrexate; Methotrexate LPF (Methotrexate); Mexate (Methotrexate); Mexate-AQ (Methotrexate); Platinol (Cisplatin); Platinol-AQ (Cisplatin); and Taxotere (Docetaxel).

Drug combinations used for treating head and neck cancer include, without limitation: TPF: Docetaxel (Taxotere) (T); Cisplatin (Platinol) (P); and Fluorouracil (F).

Leukemia

Cancer drugs approved by the FDA for treating acute lymphoblastic leukemia (ALL) include, without limitation: Abitrexate (Methotrexate); Arranon (Nelarabine); Asparaginase *Erwinia chrysanthemi*; Blinatumomab; Blincyto (Blinatumomab); Cerubidine (Daunorubicin Hydrochloride); Clafen (Cyclophosphamide); Clofarabine; Clofarex (Clofarabine); Clolar (Clofarabine); Cyclophosphamide; Cytarabine; Cytosar-U (Cytarabine); Cytoxan (Cyclophosphamide); Dasatinib; Daunorubicin Hydrochloride; Doxorubicin Hydrochloride; Erwinaze (Asparaginase *Erwinia Chrysanthemi*); Folex (Methotrexate); Folex PFS (Methotrexate); Gleevec (Imatinib Mesylate); Iclusig (Ponatinib Hydrochloride); Imatinib Mesylate; Marqibo (Vincristine Sulfate Liposome); Mercaptopurine; Methotrexate; Methotrexate LPF (Methorexate); Mexate (Methotrexate); Mexate-AQ (Methotrexate); Nelarabine; Neosar (Cyclophosphamide); Oncaspar (Pegaspargase); Pegaspargase; Ponatinib Hydrochloride; Prednisone; Purinethol (Mercaptopurine); Purixan (Mercaptopurine); Rubidomycin (Daunorubicin Hydrochloride); Sprycel (Dasatinib); Tarabine PFS (Cytarabine); Vincasar PFS (Vincristine Sulfate); Vincristine Sulfate; and Vincristine Sulfate Liposome.

Drug combinations used for treating ALL include, without limitation: Hyper-CVAD: Cyclophosphamide (C); Vincristine Sulfate (V); and Doxorubicin Hydrochloride (Adriamycin).

Cancer drugs approved by the FDA for treating acute myeloid leukemia (AML) include, without limitation: Cerubidine (Daunorubicin Hydrochloride); Clafen (Cyclophosphamide); Cyclophosphamide; Cytarabine; Cytosar-U (Cytarabine); Cytoxan (Cyclophosphamide); Daunorubicin Hydrochloride; Doxorubicin Hydrochloride; Idamycin (Idarubicin Hydrochloride); Idarubicin Hydrochloride; Mitoxantrone Hydrochloride; Neosar (Cyclophosphamide); Rubidomycin (Daunorubicin Hydrochloride); Tabloid (Thioguanine); Tarabine PFS (Cytarabine); Thioguanine; Trisenox (Arsenic Trioxide); Vincasar PFS (Vincristine Sulfate); and Vincristine Sulfate.

Drug combinations used for treating AML include, without limitation: ADE: Cytarabine (Ara-C); Daunorubicin Hydrochloride (D); and Etoposide (E).

Cancer drugs approved by the FDA for treating chronic lymphocytic leukemia (CLL) include, without limitation: Alemtuzumab; Ambochlorin (Chlorambucil); Amboclorin (Chlorambucil); Arzerra (Ofatumumab); Bendamustine Hydrochloride; Campath (Alemtuzumab); Chlorambucil; Clafen (Cyclophosphamide); Cyclophosphamide; Cytoxan (Cyclophosphamide); Fludara (Fludarabine Phosphate); Fludarabine Phosphate; Gazyva (Obinutuzumab); Ibrutinib; Idelalisib; Imbruvica (Ibrutinib); Leukeran (Chlorambucil); Linfolizin (Chlorambucil); Mechlorethamine Hydrochloride; Mustargen (Mechlorethamine Hydrochloride); Neosar (Cyclophosphamide); Obinutuzumab; Ofatumumab; Prednisone; Rituxan (Rituximab); Rituximab; Treanda (Bendamustine Hydrochloride); and Zydelig (Idelalisib).

Drug combinations used for treating CLL include, without limitation: chlorambucil-prednisone; and CVP: Cyclophosphamide (C); Vincristine Sulfate (V); and Prednisone (P).

Cancer drugs approved by the FDA for treating chronic myelogenous leukemia (CML) include, without limitation: Bosulif (Bosutinib); Bosutinib; Busulfan; Busulfex (Busulfan); Clafen (Cyclophosphamide); Cyclophosphamide; Cytarabine; Cytosar-U (Cytarabine); Cytoxan (Cyclophosphamide); Dasatinib; Gleevec (Imatinib Mesylate); Iclusig (Ponatinib Hydrochloride); Imatinib Mesylate; Mechlorethamine Hydrochloride; Mustargen (Mechlorethamine Hydrochloride); Myleran (Busulfan); Neosar (Cyclophosphamide); Nilotinib; Omacetaxine Mepesuccinate; Ponatinib Hydrochloride; Sprycel (Dasatinib); Synribo (Omacetaxine Mepesuccinate); Tarabine PFS (Cytarabine); and Tasigna (Nilotinib).

Cancer drugs approved by the FDA for treating hairy cell leukemia include, without limitation: Intron A (Recombinant Interferon Alfa-2b); and Recombinant Interferon Alfa-2b.

Cancer drugs approved by the FDA for treating meningeal leukemia include, without limitation: Cytarabine; Cytosar-U (Cytarabine); and Tarabine PFS (Cytarabine).

Lung Cancer

Cancer drugs approved by the FDA for treating non-small cell lung cancer include, without limitation: Abitrexate (Methotrexate); Abraxane (Paclitaxel Albumin-stabilized Nanoparticle Formulation); Afatinib Dimaleate; Alimta (Pemetrexed Disodium); Avastin (Bevacizumab); Bevacizumab; Carboplatin; Ceritinib; Cisplatin; Crizotinib; Cyramza (Ramucirumab); Docetaxel; Erlotinib Hydrochloride; Folex (Methotrexate); Folex PFS (Methotrexate); Gefitinib; Gilotrif (Afatinib Dimaleate); Gemcitabine Hydrochloride; Gemzar (Gemcitabine Hydrochloride); Iressa (Gefitinib); Keytruda (Pembrolizumab); Mechlorethamine Hydrochloride; Methotrexate; Methotrexate LPF (Methotrexate); Mexate (Methotrexate); Mexate-AQ (Methotrexate); Mustargen (Mechlorethamine Hydrochloride); Navelbine (Vinorelbine Tartrate); Nivolumab; Opdivo (Nivolumab); Paclitaxel; Paclitaxel Albumin-stabilized Nanoparticle Formulation; Paraplat (Carboplatin); Paraplatin (Carboplatin); Pembrolizumab; Pemetrexed Disodium; Platinol (Cisplatin); Platinol-AQ (Cisplatin); Ramucirumab; Tarceva (Erlotinib Hydrochloride); Taxol (Paclitaxel); Taxotere (Docetaxel); Vinorelbine Tartrate; Xalkori (Crizotinib); and Zykadia (Ceritinib).

Drug combinations used for treating non-small cell lung cancer include, without limitation: Carboplatin-Taxol and Gemcitabine-Cisplatin.

Cancer drugs approved by the FDA for treating small cell lung cancer include, without limitation: Abitrexate (Methotrexate); Doxorubicin Hydrochloride; Etopophos (Etoposide Phosphate); Etoposide; Etoposide Phosphate; Folex (Methotrexate); Folex PFS (Methotrexate); Hycamtin (Topotecan Hydrochloride); Mechlorethamine Hydrochloride; Methotrexate; Methotrexate LPF (Methotrexate); Mexate (Methotrexate); Mexate-AQ (Methotrexate); Mustargen (Mechlorethamine Hydrochloride); Toposar (Etoposide); Topotecan Hydrochloride; and VePesid (Etoposide).

Skin Cancer

Cancer drugs approved by the FDA for treating basal cell carcinoma include, without limitation: Adrucil (Fluorouracil); Aldara (Imiquimod); Efudex (Fluorouracil); Erivedge (Vismodegib); 5-FU (Fluorouracil); Fluoroplex (Fluorouracil); Fluorouracil; Imiquimod; Odomzo (Sonidegib); Sonidegib; and Vismodegib.

Cancer drugs approved by the FDA for treating melanoma include, without limitation: Aldesleukin; Dabrafenib; Dacarbazine; DTIC-Dome (Dacarbazine); IL-2 (Aldesleukin); Imlygic (Talimogene Laherparepvec); Interleukin-2 (Aldesleukin); Intron A (Recombinant Interferon Alfa-2b); Ipilimumab; Keytruda (Pembrolizumab); Mekinist (Trametinib); Nivolumab; Opdivo (Nivolumab); Peginterferon Alfa-2b; Pembrolizumab; Proleukin (Aldesleukin); Recombinant Interferon Alfa-2; Sylatron (Peginterferon Alfa-2b); Tafinlar (Dabrafenib); Talimogene Laherparepvec; Trametinib; Vemurafenib; Yervoy (Ipilimumab); and Zelboraf (Vemurafenib).

Gastric (Stomach) Cancer

Cancer drugs approved by the FDA for treating melanoma include, without limitation: Adrucil (Fluorouracil); Cyramza (Ramucirumab); Docetaxel; Doxorubicin Hydrochloride; Efudex (Fluorouracil); 5-FU (Fluorouracil); Fluoroplex (Fluorouracil); Fluorouracil; Herceptin (Trastuzumab); Mitomycin C; Mitozytrex (Mitomycin C); Mutamycin (Mitomycin C); Ramucirumab; Taxotere (Docetaxel); and Trastuzumab.

Drug combinations used for treating gastric cancer include, without limitation: FU-LV; TPF; and XELIRI.

Malignant Mesothelioma

Cancer drugs approved by the FDA for treating malignant mesothelioma include, without limitation: Alimta (Pemetrexed Disodium); Cisplatin; Pemetrexed Disodium; Platinol (Cisplatin); and Platinol-AQ (Cisplatin).

Drug combinations used for treating malignant mesothelioma include, without limitation: gemcitabine-cisplatin.

Esophageal Cancer

Cancer drugs approved by the FDA for treating esophageal cancer include, without limitation: Cyramza (Ramucirumab); Docetaxel; Herceptin (Trastuzumab); Ramucirumab; Taxotere (Docetaxel); and Trastuzumab.

Drug combinations used for treating malignant esophageal cancer include, without limitation: FU-LV and XELIRI.

Synovial Sarcoma

Drug combinations used for treating synovial sarcoma include, without limitation: Doxorubicin and/or Ifosfamide. The primary treatment for synovial sarcoma is surgical resection, preferably with clear margins.

Cervical Cancer

Cancer drugs approved by the FDA for treating cervical cancer include, without limitation: Avastin (Bevacizumab); Bevacizumab; Blenoxane (Bleomycin); Bleomycin; Cisplatin; Hycamtin (Topotecan Hydrochloride); Platinol (Cisplatin); Platinol-AQ (Cisplatin); and Topotecan Hydrochloride.

Drug combinations used for treating cervical cancer include, without limitation: Gemcitabine-Cisplatin.

Bladder Cancer

Cancer drugs approved by the FDA for treating bladder cancer include, without limitation: Cisplatin; Doxorubicin Hydrochloride; Platinol (Cisplatin); Platinol-AQ (Cisplatin); and Thiotepa.

Drug combinations used for treating bladder cancer include, without limitation: Gemcitabine-Cisplatin.

Wilms Tumor

Drugs used for treating Wilms Tumor include, without limitation: actinomycin D, vincristine, doxorubicin, cyclophosphamide, etoposide, carboplatin, mesna (to protect the bladder from the effects of the cyclophosphamide), and irinotecan, and combinations thereof.

It is, moreover, understood that the macrocycles described herein, or a composition thereof, may be administered in conjunction with a therapeutic regimen that calls for radiation and/or surgery. The order in which combination therapies are administered may vary depending on, for example, the cancer to be treated, the stage of the cancer, and the general health of the patient afflicted with the cancer. The macrocycles described herein, or a composition thereof, may, for example, be administered alone or in a combination therapy to shrink a tumor in advance of surgical resection and/or may be administered after surgical resection to minimize or ablate residual disease.

In further method of treatment aspects, methods are presented for treating a mammal susceptible to or afflicted with pulmonary fibrosis, wherein such methods comprise administering an effective condition-treating or condition-preventing amount of one or more of the pharmaceutical compositions just described. Idiopathic pulmonary fibrosis (IPF) is a progressive disease with a high mortality rate. Dysregulation of the Wnt/β-catenin pathway has been implicated in lung fibrosis. See, for example, Lam et al, (2014, Am J Resp Crit Care Med 190:185); Selman et al. (2008, PLOS Med 5:e62); Henderson et al. (2010, Proc Natl Acad Sci USA 107: 14309); Ulsamer et al. (2012, J Biol Chem 287:5164); Akhmetshina et al. (2012, Nat Commun 3:735); and Konigshoff et al. (2009, J Clin Invest 119:772); the entire content of each of which is incorporated herein by reference.

Also envisioned herein are combination therapies for the treatment of IPF. Such combination therapies comprise administration of at least one of the present macrocycles in combination with a therapeutic regimen currently applied to the care of patients suffering from pulmonary fibrosis. Guidelines for the care of IPF are known in the art and may be provided by the American Thoracic Society, European Respiratory Society, Japanese Respiratory Society, and the Latin American Thoracic Association. The salient points regarding guidelines for therapeutic intervention are as follows: use of nintedanib, a tyrosine kinase inhibitor that targets multiple tyrosine kinases, including vascular endothelial growth factor, fibroblast growth factor, and PDGF receptors; pirfenidone; and antacid therapy, even in patients without symptoms of gastroesophageal reflux (GER), are conditionally recommended. Pirfenidone (Esbriet), available from Roche Holding AG, and nintedanib (Ofev), available from Boehringer Ingelheim GmbH, received FDA approval for treating IPF in 2014. The guidelines also provide a conditional recommendation against using N-acetylcysteine monotherapy, sildenafil, macitentan, and bosentan. The guidelines further recommend against the use of anticoagulation agents (warfarin); imatinib, a selective tyrosine kinase inhibitor against platelet-derived growth factor (PDGF) receptors; combination prednisone, azathioprine, and N-acetylcysteine; and selective endothelin receptor antagonist (ambrisentan). As is understood in the art, people who are diagnosed with pulmonary fibrosis may initially be treated with a corticosteroid (e.g., prednisone), sometimes in combination with other drugs that suppress the immune system (e.g., methotrexate or cyclosporine). Adding acetylcysteine, a derivative of a natural amino acid, to prednisone may slow the disease in some people. Accordingly, the combination therapy encompassed herein may comprise administration of at least one of the present macrocycles in combination with a corticosteroid alone or in combination with an immunosuppressant such as methotrexate or cyclosporine. Combination therapy encompassed herein may also comprise administration of at least one of the present macrocycles in combination with oxygen therapy, pulmonary rehabilitation, and/or surgery. All of the above therapeutic interventions are known in the art to be implemented for treating pulmonary fibrosis and are described in various websites, including that provided by the Mayo Clinic.

As a further aspect of the disclosure the present compounds are provided for use as a pharmaceutical especially in the treatment or prevention of the aforementioned conditions and diseases. Also provided herein is the use of the present compounds in the manufacture of a medicament for the treatment or prevention of one of the aforementioned conditions and diseases.

In an embodiment, injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as psoriasis, the regimen for treatment usually stretches over many months or years so oral dosing is preferred for patient convenience and tolerance. Psoriasis, for example, has been linked to Wnt signaling. Several basic and clinical studies using patient samples revealed an increase in nuclear β-catenin staining in many psoriatic samples. It has been suggested that a sustained low-level increase in Wnt/β-catenin signaling could be responsible for skin psoriatic lesions. With oral dosing, one to five and especially two to four and typically three oral doses per day are representative regimens. Using these dosing patterns, each dose provides from about 0.01 to about 20 mg/kg of the compound of the disclosure, with preferred doses each providing from about 0.1 to about 10 mg/kg and especially about 1 to about 5 mg/kg.

Transdermal doses are generally selected to provide similar or lower blood levels than are achieved using injection doses.

When used to prevent the onset of a hyperproliferative condition, the compounds of this disclosure may be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this disclosure may be administered as the sole active agent or they may be administered in combination with other agents, including other compounds that demonstrate the same or a similar therapeutic activity, and that are determined to safe and efficacious for such combined administration.

General Synthetic Procedures

The macrocycles described herein may be prepared from readily available starting materials using the general methods and procedures described earlier and illustrated schematically in the examples that follow. It will be appreciated that where typical or preferred process conditions (i.e., reaction temperatures, times, mole ratios of reactants, solvents, pressures, etc.) are given, other process conditions may also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The following methods are presented with details as to the preparation of representative peptoid oligomers that have been listed hereinabove. The peptoid-peptide macrocycles described herein may be prepared from known or commercially available starting materials and reagents by one skilled in the art of organic synthesis.

Solvents and reagents purchased from commercial sources were used without further purification. Abbreviations for reagents are as follows: 9-fluorenylmethoxycarbonyl (Fmoc); tert-butoxycarbonyl (Boc); benzotriazole-1-yl-oxy-tris-pyrrolidino-phosphonium hexafluorophosphate (PyBOP); Bromo-tris-pyrrolidino phosphoniumhexafluorophosphate (PyBrOP); trifluoroacetic acid (TFA); hexafluoroisopropyl alcohol (HFIP); methylene chloride (DCM); N,N'-dimethylformamide (DMF); N,N'-diisopropylcarbodiimide (DIC); diisopropylethylamine (DIEA); acetonitrile (ACN); N-methylmorpholine (NMM); O-Benzotriazole-N,N,N',N'-tetramethyl-uronium-hexafluoro-phosphate (HBTU).

A class peptide-peptoid macrocycles that features a characteristic structure induced upon cyclization were prepared. Within this family, several representative macrocycles are hexamers. The macrocycles are synthesized using solid phase protocols to include a specific sequence of diverse side chain functional groups. The side chains have been selected using the computational modeling package Rosetta to provide complementarity to the β-catenin surface. Although the linear oligomer may be poorly ordered, upon installation of the macrocyclic covalent constraint, the oligomer displays extensive conformational ordering, enabling the molecule to be pre-organized for binding to the target protein surface. The cyclization-induced ordering is readily observed by circular dichroism spectroscopy (FIG. 1).

A library of cyclic hybrid oligomers was synthesized (FIG. 2). The oligomers were then evaluated for their ability to inhibit the Wnt signaling pathway in cell culture.

Desirable features of macrocycles of the present disclosure include, but are not limited to:
- the distinctive chemical composition of the oligomers, consisting largely of peptoid monomer units that are known to have desirable stability and pharmacological attributes,
- their macrocyclic forms, which establish favorable binding and cell-uptake characteristics, and
- the inclusion of side chain groups that are predicted to establish the desired binding, proper steric complimentarity, functional groups with suitable physico-chemical properties to enhance association with a target surface (e.g., β-catenin), and bioactivities.

The following Statements provide non-limiting examples of of the present disclosure:

Statement 1. A peptoid-peptide macrocycle of formula A:

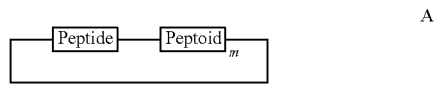

A where "Peptide" is a single amino acid residue, beta-amino acid residue, gamma-amino acid residue, oligo-urea residue, or aromatic oligoamides; "Peptoid" is an N-substituted amino acid residue, beta-peptoid residue; alpha-beta alternating peptoid residue, azapeptoid residue, aminoxypeptoid residue, ureapeptoid residue, or a combination thereof, and m is an integer from 2-20; or a pharmaceutically acceptable salt, solvate or prodrug thereof; and stereoisomers, isotopic variants and tautomers thereof.

Statement 1a. A peptoid-peptide macrocycle according to Statement 1, where the peptoid-peptide macrocycle does not have the following structure:

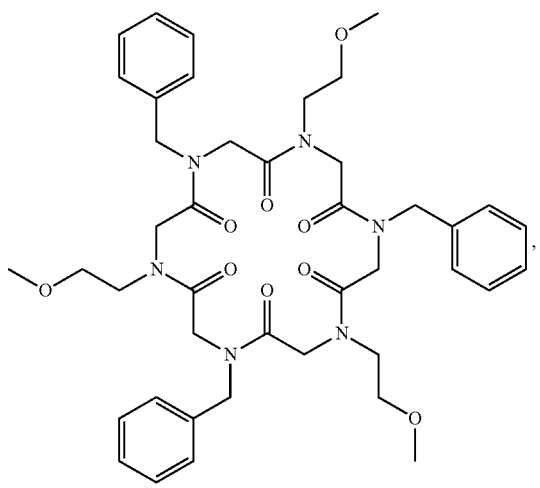

,

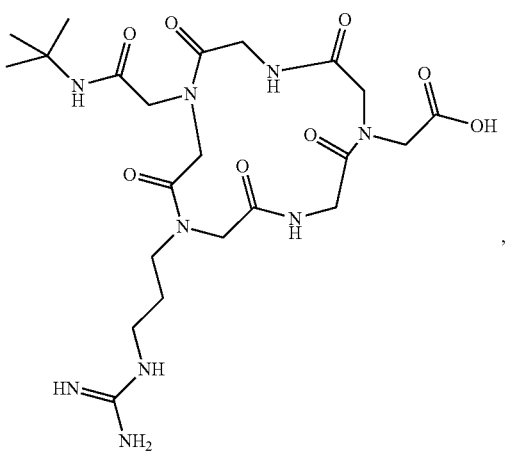

,

-continued
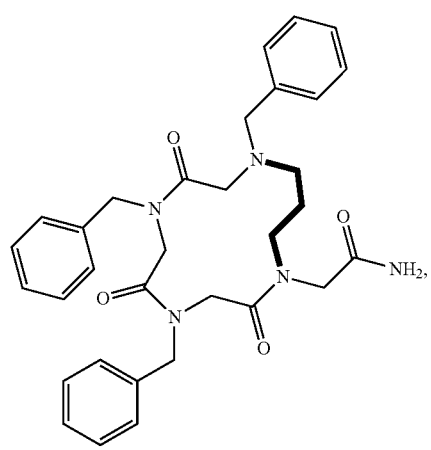
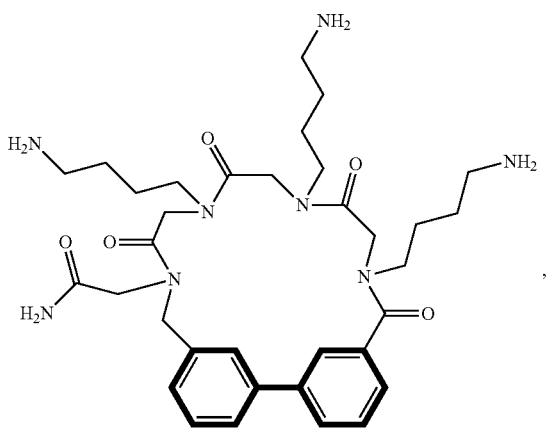
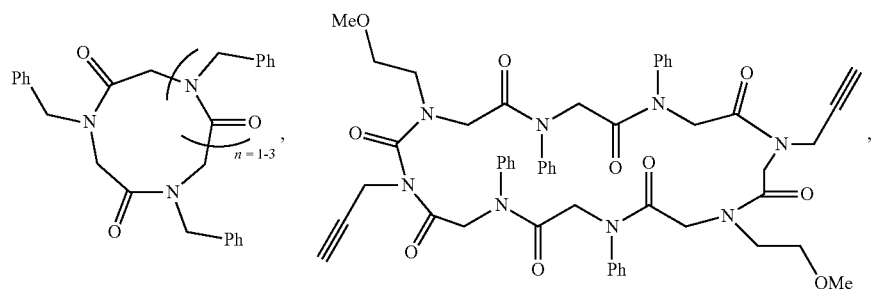
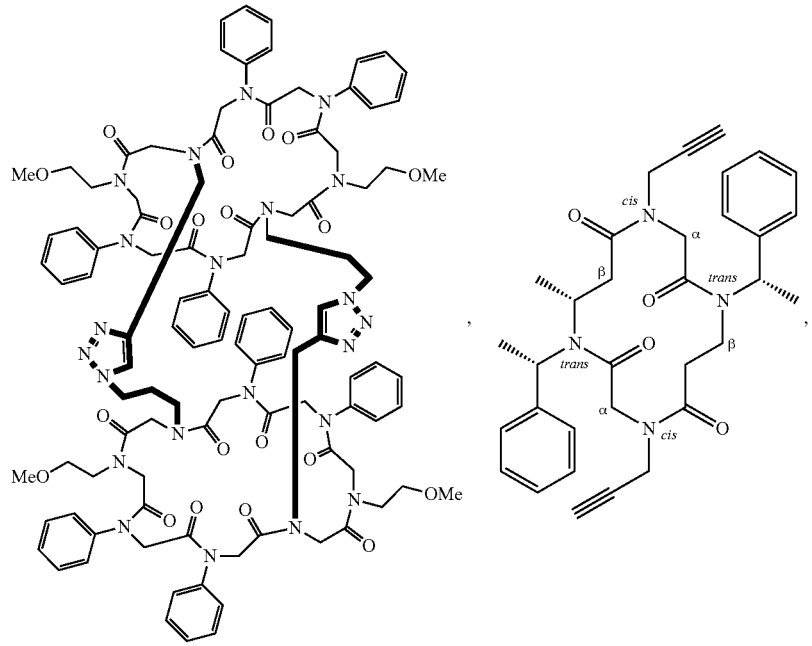

103
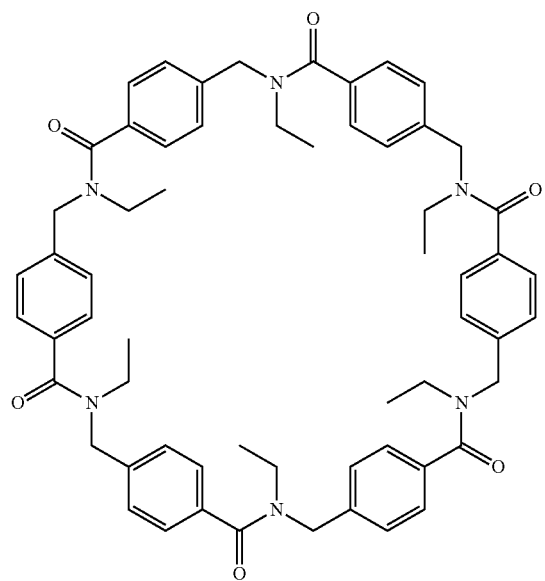
104
-continued
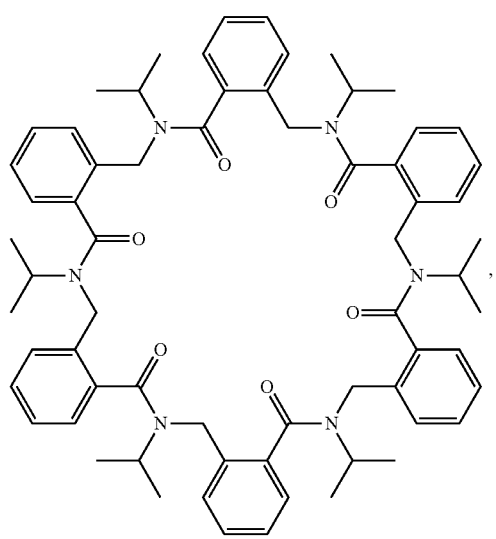
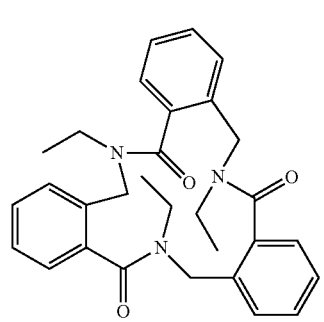, 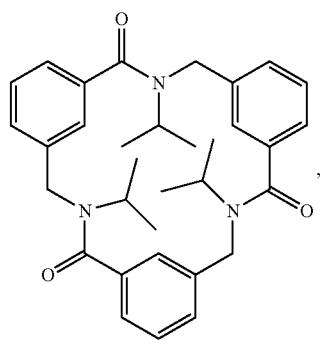, 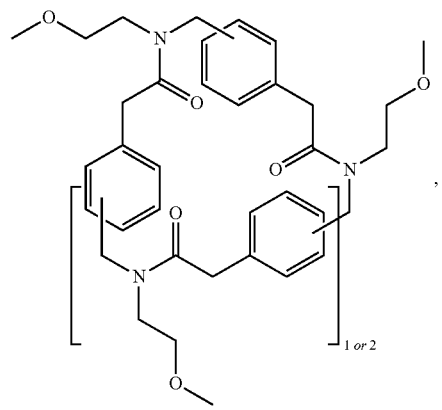
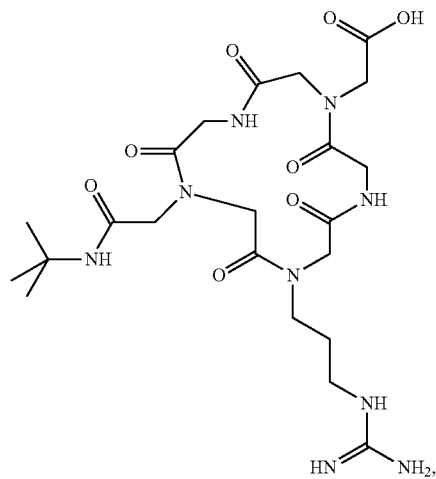

-continued
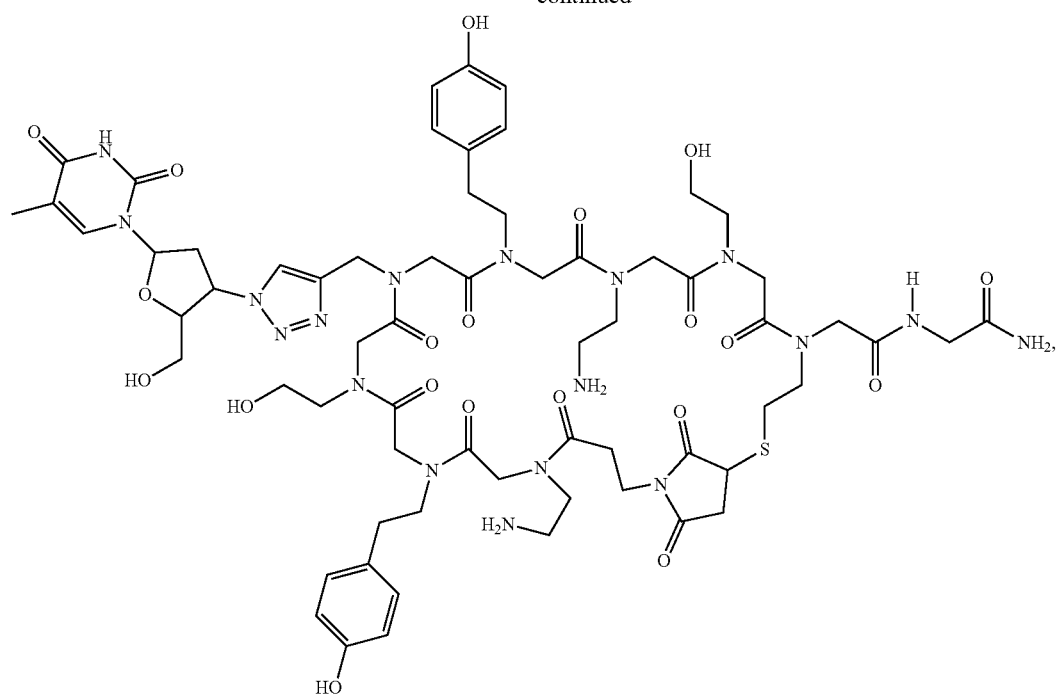
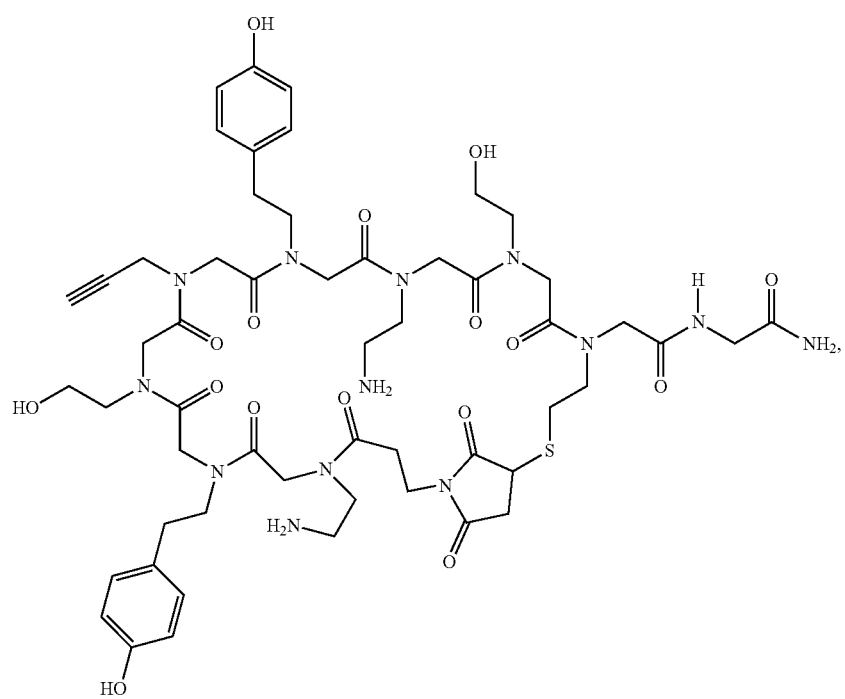

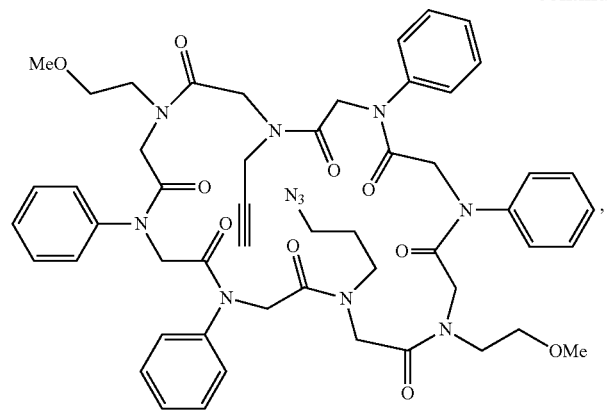
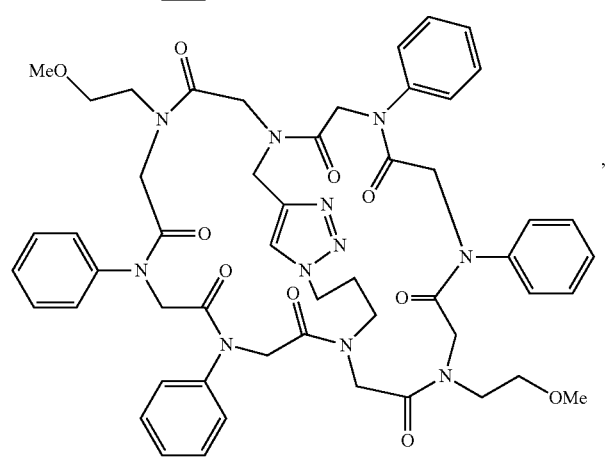
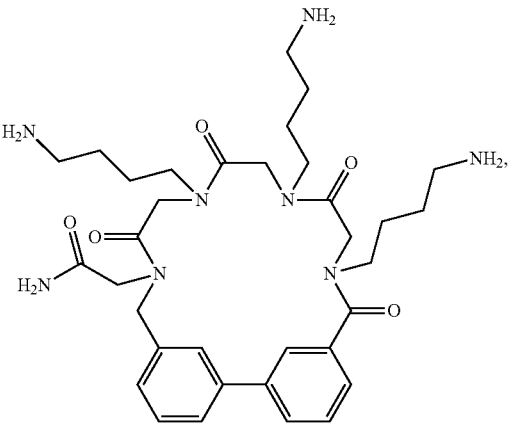
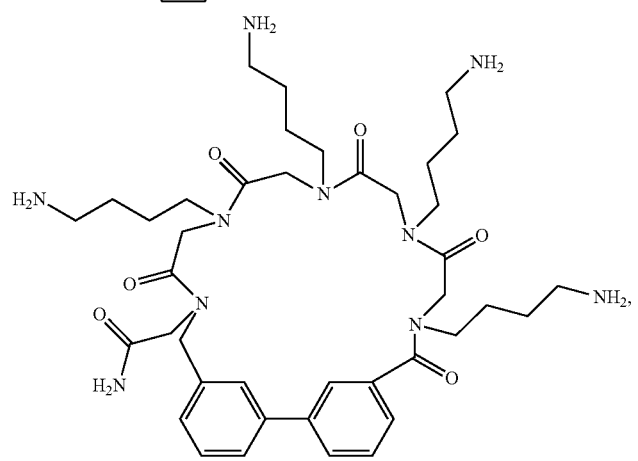
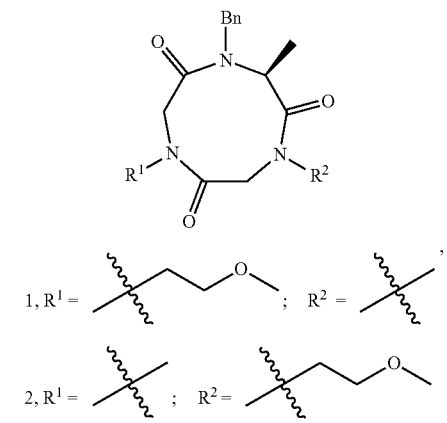
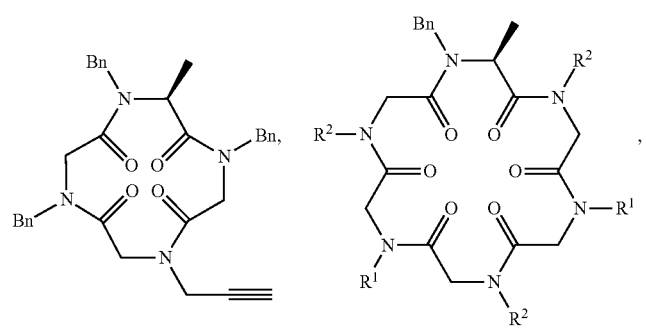
4, R¹; R² = Bn
5, R¹ = Bn; R² = iPr
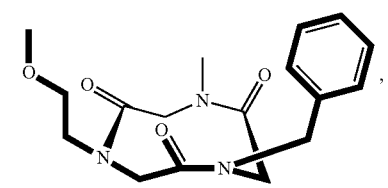

-continued
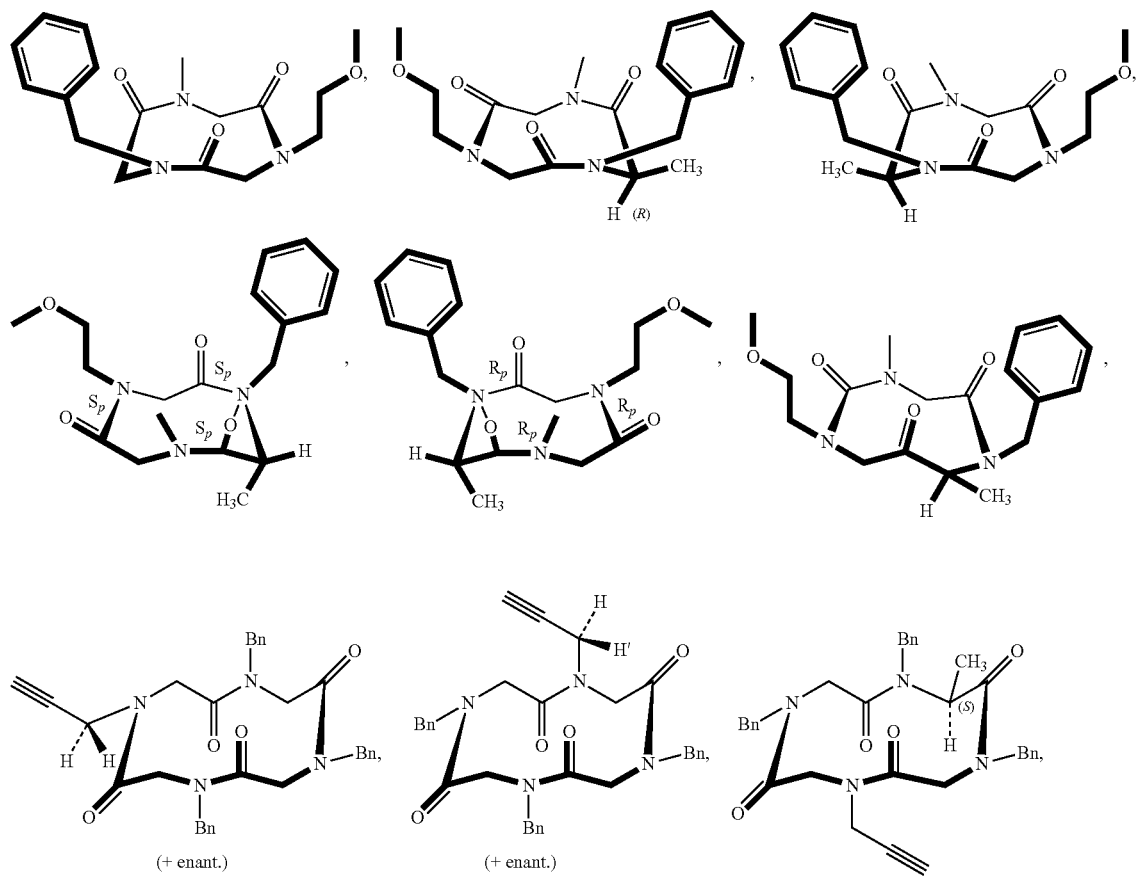
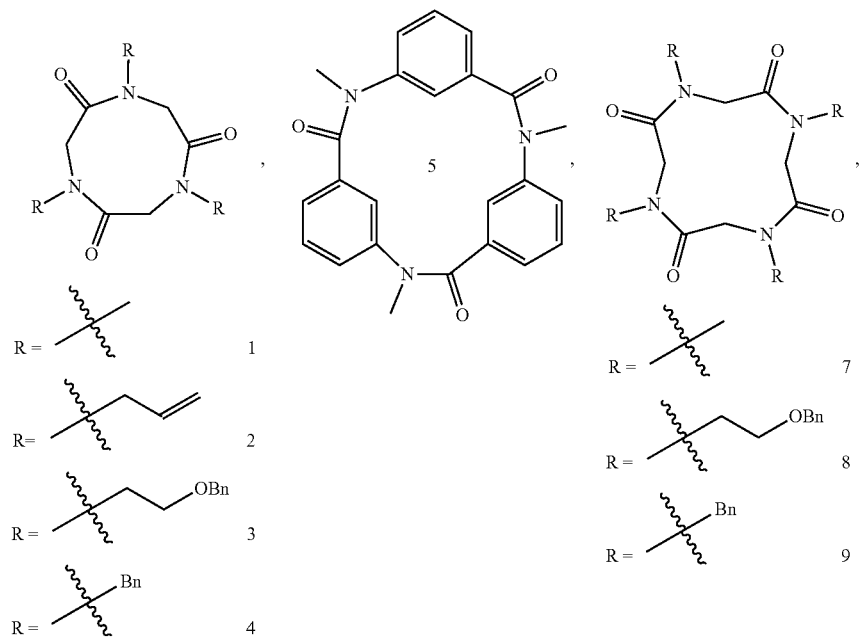

-continued
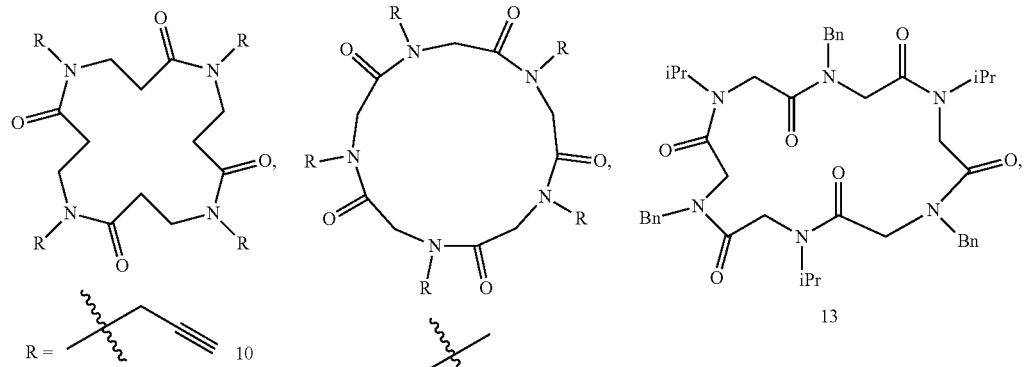
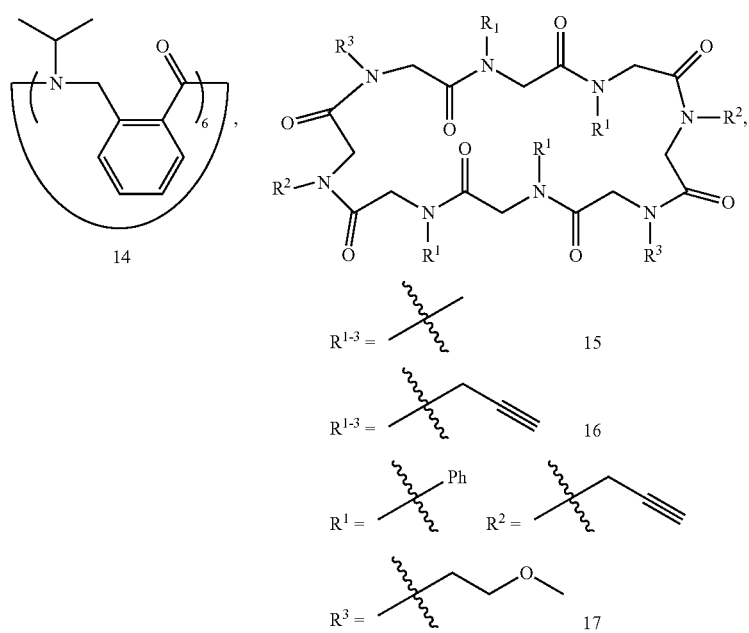
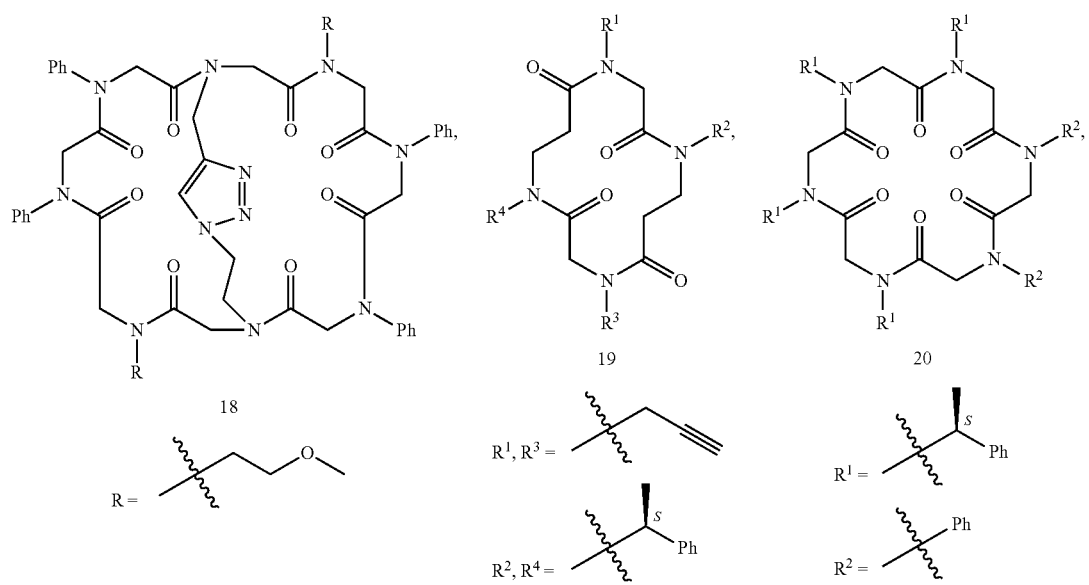

-continued

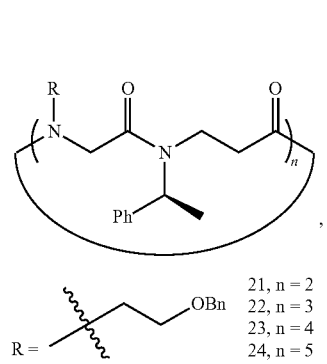

21, n = 2
22, n = 3
23, n = 4
24, n = 5

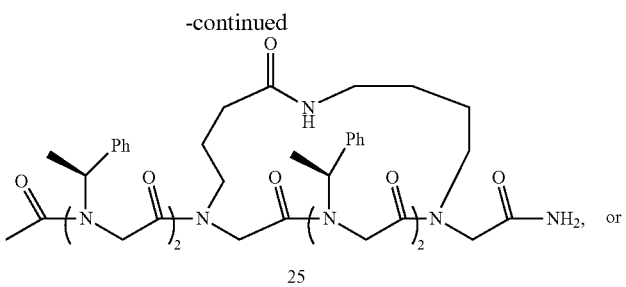

25

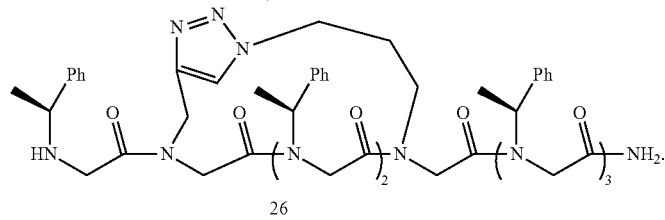

26

Statement 2. A peptoid-peptide macrocycle according to Statement 1, where "Peptide" is glycine, D-alanine, D-valine, D-leucine, D-isoleucine, D-tyrosine, D-proline, D-serine, D-glutamic acid, D-tryptophan, D-phenylalanine, D-methionine, D-arginine, D-histidine, D-glutamine, D-lysine, D-aspartic acid, D-threonine, D-cysteine, D-asparagine, or a D-unnatural amino acid (e.g., an unnatural amino acid similar to alanine having D-stereochemistry, D-amino-isobutryic acid, and the like).

Statement 3. A peptoid-peptide macrocycle according to Statement 1, where "Peptide" is glycine, L-alanine, L-valine, L-leucine, L-isoleucine, L-tyrosine, L-proline, L-serine, L-glutamic acid, L-tryptophan, L-phenylalanine, L-methionine, L-arginine, L-histidine, L-glutamine, L-lysine, L-aspartic acid, L-threonine, L-cysteine, or L-asparagine, or an L-unnatural amino acid (e.g., L-amino-isobutryic acid and the like).

Statement 4. A peptoid-peptide macrocycle according to Statement 3, where "Peptide" is D-alanine.

Statement 5. A peptoid-peptide macrocycle according to any one of the preceding Statements, where "Peptoid" comprises various N-substituted glycine monomers.

Statement 6. A peptoid-peptide macrocycle according to any one of the preceding Statements, where the N-substitution is selected from substituted or unsubstituted alkyl, substituted or unsubstituted cycloalkyl, substituted or unsubstituted heterocycloalkyl, substituted or unsubstituted aryl, and substituted or unsubstituted heteroaryl.

Statement 7. A peptoid-peptide macrocycle according to any one of the preceding Statements, where "Peptoid" is

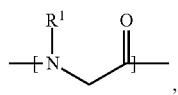

where $R^1$ is selected from substituted or unsubstituted alkyl, substituted or unsubstituted cycloalkyl, substituted or unsubstituted heterocycloalkyl, substituted or unsubstituted aryl, and substituted or unsubstituted heteroaryl.

Statement 8. A peptoid-peptide macrocycle according to Statement 1, where "Peptide" is

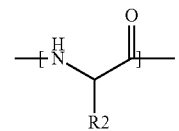

where $R^2$ is selected from substituted or unsubstituted alkyl, a canonical amino acid sidechain, or an unnatural amino acid side chain.

Statement 9. A peptoid-peptide macrocycle according to Statement 8, where "Peptide" is

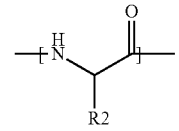

Where the moiety —NH—CH($R^2$)—C(O)— is an amino acid residue or unnatural amino acid residue.

Statement 10. A peptoid-peptide macrocycle according to Statement 9, where $R^2$ is H or Me.

Statement 11. A peptoid-peptide macrocycle according to Statement 1, where the peptoid-peptide macrocycle is formula I:

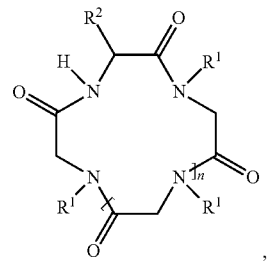

I or a pharmaceutically acceptable salt, solvate or prodrug thereof, and stereoisomers, isotopic variants and tautomers thereof; where the moiety —NH—CH(R²)—C(O)— is an amino acid residue or unnatural amino acid residue; each R¹ is independently substituted or unsubstituted alkyl, substituted or unsubstituted cycloalkyl, substituted or unsubstituted heterocycloalkyl, substituted or unsubstituted aryl, or substituted or unsubstituted heteroaryl; and the subscript n is an integer from 0 to 15 (0, 1, 2, 3, 4, 5, 6, 7, 8, 9, 10, 11, 12, 13, 14, or 15).

Statement 12. A peptoid-peptide macrocycle according to Statement 11, wherein each occurrence of R¹ is independently chosen from methoxy-ethyl, 4-methoxy-phenyl-ethyl, 3,5-dimethoxy-phenyl, (S)-4-methoxy-phenyl-ethyl, (S)-4-fluoro-phenyl-ethyl, 2-phenoxy-phenyl-ethyl, iso-propoxy-propyl, methoxy-propyl, or substituent derived from any amino submonomer disclosed herein.

Statement 13. A peptoid-peptide macrocycle according to Statement 11 or Statement 12, where the subscript n is 1.

Statement 14. A peptoid-peptide macrocycle according to Statement 11 or Statement 12, where the subscript n is 2.

Statement 15. A peptoid-peptide macrocycle according to Statement 11 or Statement 12, where the subscript n is 3.

Statement 16. A peptoid-peptide macrocycle according to Statement 1, where the peptoid-peptide macrocycle is formula IIa, IIb, or IIc:

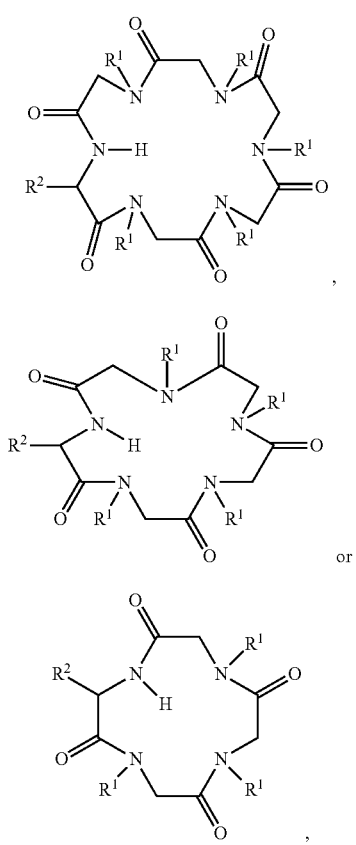

where the moiety —NH—CH(R²)—C(O)— is an amino acid residue or unnatural amino acid residue, and R¹ is as in Statement 6.

Statement 17. A peptoid-peptide macrocycle according to Statement 11 or Statement 16, where the moiety —NH—CH(R²)—C(O)— is an amino acid residue; and the amino acid is glycine, D-alanine, D-valine, D-leucine, D-isoleucine, D-tyrosine, D-proline, D-serine, D-glutamic acid, D-tryptophan, D-phenylalanine, D-methionine, D-arginine, D-histidine, D-glutamine, D-lysine, D-aspartic acid, D-threonine, D-cysteine, D-asparagine, or unnatural D-amino acid (e.g., D-amino-isobutryic acid).

Statement 18. A peptoid-peptide macrocycle according to Statement 11 or Statement 16, where the moiety —NH—CH(R²)—C(O)— is an amino acid residue; and the amino acid is glycine, L-alanine, L-valine, L-leucine, L-isoleucine, L-tyrosine, L-proline, L-serine, L-glutamic acid, L-tryptophan, L-phenylalanine, L-methionine, L-arginine, L-histidine, L-glutamine, L-lysine, L-aspartic acid, L-threonine, L-cysteine, L-asparagine, or L-unnatural amino acid (e.g., amino-isobutryic acid).

Statement 19. A peptoid-peptide macrocycle according to any one of Statements 7-18, where each R¹ is independently substituted or unsubstituted alkyl, substituted or unsubstituted substituted or unsubstituted phenyl, substituted or unsubstituted naphthyl, substituted or unsubstituted benzyl, substituted or unsubstituted phenethyl, or substituted or unsubstituted heteroaryl.

Statement 20. A peptoid-peptide macrocycle according to Statement 19, where unsubstituted alkyl is Me, Et, n-Pr, i-Pr, n-Bu, sec-Bu, or i-Bu.

Statement 21. A peptoid-peptide macrocycle according to Statement 19, where substituted alkyl is alkyl substituted with one or more groups independently chosen from halo, hydroxy, amino, alkylamino, dialkylamino, acyloxy, substituted or unsubstituted phenyl, and alkoxy.

Statement 22. A peptoid-peptide macrocycle according to Statement 19, where substituted alkyl is alkyl substituted with one or more groups independently chosen from F, Cl, CN, OMe, OAc, O-i-Pr, 4-methoxyphenyl, and CF₃.

Statement 23. A peptoid-peptide macrocycle according to Statement 19, where substituted phenyl, substituted naphthyl, substituted benzyl, substituted phenethyl is phenyl, naphthyl, benzyl, or phenethyl each substituted with one or more groups independently chosen from halo, hydroxy, amino, alkylamino, dialkylamino, and alkoxy.

Statement 24. A peptoid-peptide macrocycle according to Statement 19, where substituted phenyl, substituted naphthyl, substituted benzyl, substituted phenethyl is phenyl, naphthyl, benzyl, or phenethyl each substituted with one or more groups independently chosen from F, Cl, CN, OMe, and CF₃.

Statement 25. A peptoid-peptide macrocycle according to Statement 19, where substituted heteroaryl is heteroaryl substituted with one or more groups independently chosen from halo, hydroxy, amino, alkylamino, dialkylamino, and alkoxy.

Statement 26. A peptoid-peptide macrocycle according to Statement 19, where substituted heteroaryl is heteroaryl substituted with one or more groups independently chosen from F, Cl, CN, OMe, and CF₃.

Statement 27. A peptoid-peptide macrocycle according to Statement 25 or Statement 26, where heteroaryl is furanyl, thienyl, pyrrolyl, imidazolyl, pyridyl, or pyrimidinyl.

Statement 28. A peptoid-peptide macrocycle according to any one of Statements 7-18, where each R¹ independently is:
  i) unsubstituted alkyl;
  ii) Me, Et, n-Pr, i-Pr, n-Bu, sec-Bu, or i-Bu;
  iii) alkyl substituted with one or more groups independently chosen from halo, hydroxy, amino, alkylamino, dialkylamino, acyl, acyloxy, substituted or unsubstituted phenyl, and alkoxy;

iv) alkyl substituted with one or more groups independently chosen from F, Cl, CN, OMe, O-i-Pr, 4-methoxyphenyl, 2-phenoxyphenyl, and $CF_3$;

v) unsubstituted phenyl;

vi) unsubstituted naphthyl;

vii) unsubstituted benzyl;

viii) unsubstituted phenethyl;

ix) phenyl substituted with one or more groups independently chosen from halo, alkyl, haloalkyl, CN, hydroxy, amino, alkylamino, dialkylamino, and alkoxy;

x) naphthyl substituted with one or more groups independently chosen from halo, alkyl, haloalkyl, CN, hydroxy, amino, alkylamino, dialkylamino, and alkoxy;

xi) benzyl substituted with one or more groups independently chosen from halo, alkyl, haloalkyl, CN, hydroxy, amino, alkylamino, dialkylamino, substituted or unsubstituted phenoxy, and alkoxy;

xii) phenethyl substituted with one or more groups independently chosen from halo, alkyl, haloalkyl, CN, hydroxy, amino, alkylamino, dialkylamino, and alkoxy;

xiii) phenyl substituted with one or more groups independently chosen from F, Cl, CN, OMe, and $CF_3$;

xiv) naphthyl substituted with one or more groups independently chosen from F, Cl, CN, OMe, and $CF_3$;

xv) benzyl substituted with one or more groups independently chosen from F, Cl, CN, OMe, OPh, and $CF_3$;

xvi) phenethyl substituted with one or more groups independently chosen from F, C, CN, OMe, and $CF_3$;

xvii) unsubstituted heteroaryl;

xviii) heteroaryl substituted with one or more groups independently chosen from halo, hydroxy, amino, alkylamino, dialkylamino, and alkoxy;

xix) heteroaryl substituted with one or more groups independently chosen from F, Cl, CN, OMe, and $CF_3$; or any combinations thereof.

Statement 29. A peptoid-peptide macrocycle according to Statement 28, where heteroaryl is furanyl, thienyl, pyrrolyl, imidazolyl, pyridyl, or pyrimidinyl.

Statement 30. A peptoid-peptide macrocycle according to any one of Statements 7-29, where each $R^1$ independently is methoxyethyl, i-propoxyethyl, dimethoxyphenyl, fluorophenethyl, or methoxyphenethyl.

Statement 31. A peptoid-peptide macrocycle according to any one of Statements 7-29, where each $R^1$ independently is 2-methoxyethyl, 2-i-propoxyethyl, 3,4-dimethoxyphenyl, 1-(4-fluorophen)ethyl, 1-(2-phenoxyphen)ethyl, 1-(4-methoxyphen)ethyl, 2-(2-phenoxyphen)ethyl, or 2-(4-methoxyphen)ethyl.

Statement 32. A peptoid-peptide macrocycle according to any one of Statements 1-31, where "Peptide" or the moiety —NH—CH($R^2$)—C(O)— is D-alanine.

Statement 33. A peptoid-peptide macrocycle according to Statement 1, where the macrocycle is any one of the macrocycles listed in FIG. 2, which are:

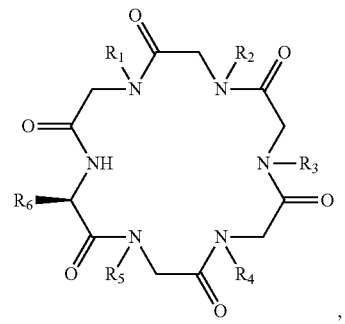

wherein $R_1$ is

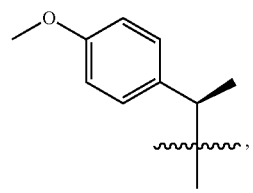

$R_2$ is

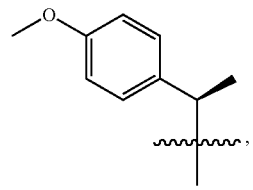 [SMILES: *[C@H](C)c1ccc(OC)cc1]

$R_3$ is

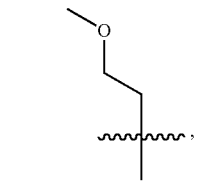

$R_4$ is

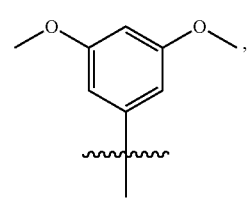

| 119 | 120 |
|---|---|
| R₅ is 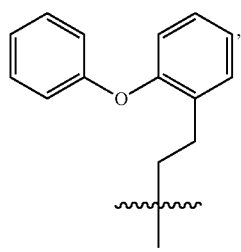 [SMILES: *CCc1ccccc1Oc1ccccc1] | R₅ is 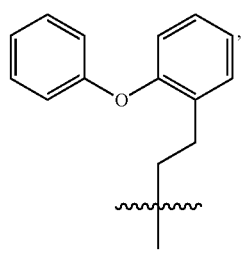 |
| and R₆ is 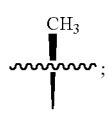 ; | and R₆ is 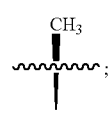 ; |
| R₁ is 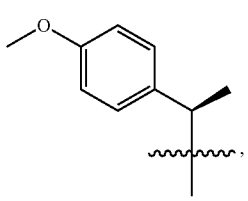 [SMILES: *[C@H](C)c1ccc(OC)cc1] , | R₁ is 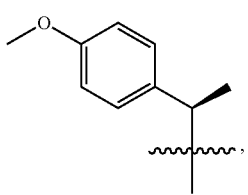 , |
| R₂ is 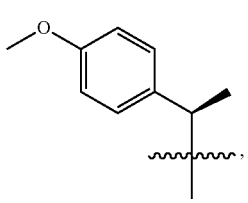 [SMILES: *[C@H](C)c1ccc(OC)cc1] , | R₂ is 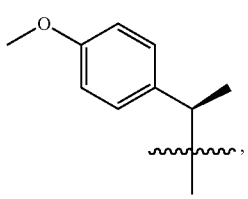 , |
| R₃ is 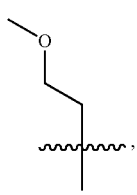 [SMILES: *CCOC] , | R₃ is 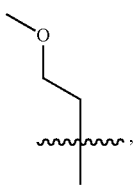 , |
| R₄ is 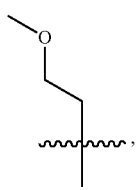 [SMILES: *CCOC] , | R₄ is 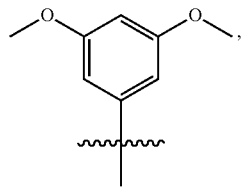 , |

121
$R_5$ is
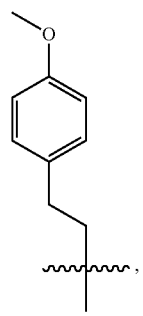 [SMILES: *CCc1ccc(OC)cc1]
and $R_6$ is
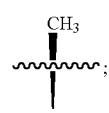
$R_1$ is
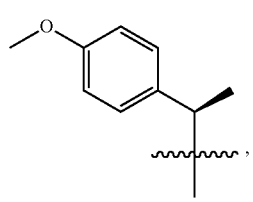 [SMILES: *[C@H](C)c1ccc(OC)cc1]
$R_2$ is
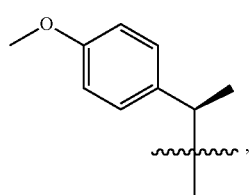
$R_3$ is
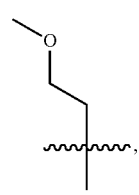 [SMILES: *CCOC]
122
$R_4$ is
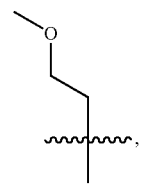 [SMILES: *CCOC]
$R_5$ is
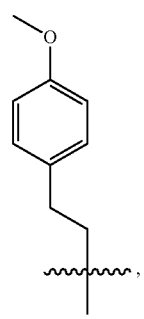
and $R_6$ is
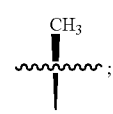
$R_1$ is
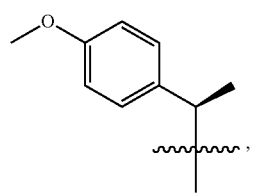 [SMILES: *[C@H](C)c1ccc(OC)cc1]
$R_2$ is
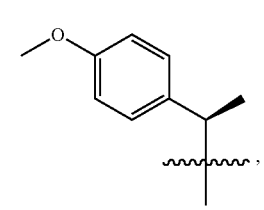 [SMILES: *[C@H](C)c1ccc(OC)cc1]

123
$R_3$ is
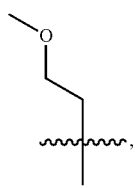 [SMILES: *CCOC]
$R_4$ is
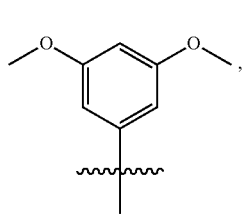
$R_5$ is
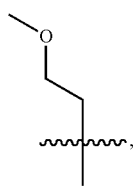
and $R_6$ is
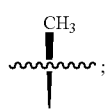
$R_1$ is
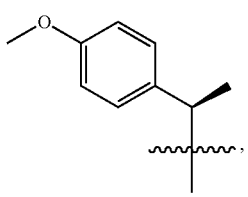 [SMILES: *[C@H](C)c1ccc(OC)cc1]
$R_2$ is
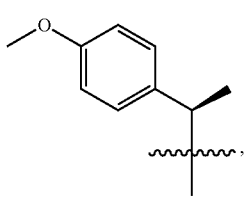 [SMILES: *[C@H](C)c1ccc(OC)cc1]
124
$R_3$ is
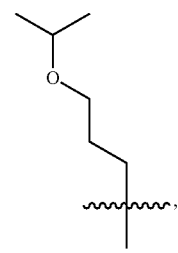 [SMILES: *CCCOC(C)C]
$R_4$ is
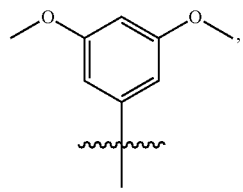
$R_5$ is
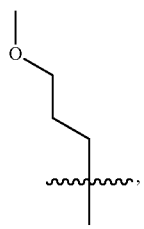
and $R_6$ is
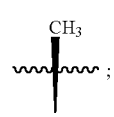
$R_1$ is
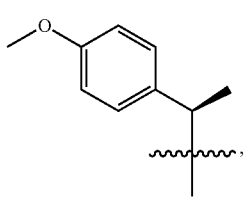 [SMILES: *[C@H](C)c1ccc(OC)cc1]
$R_2$ is
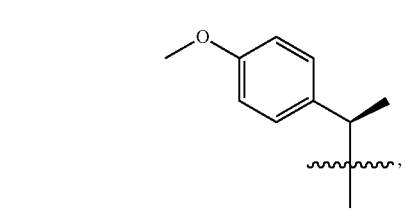 [SMILES: *[C@H](C)c1ccc(OC)cc1]

125
R₃ is
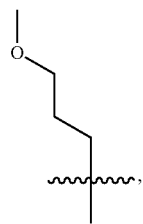 [SMILES: *CCCOC]
R₄ is
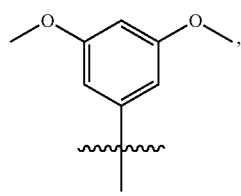
R₅ is
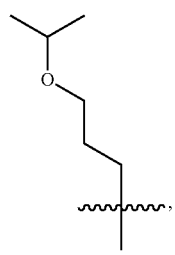 [SMILES: *CCCOC(C)C]
and R₆ is
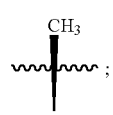;
R₁ is
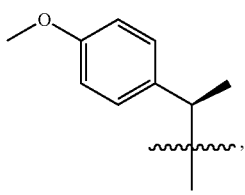 [SMILES: *[C@H](C)c1ccc(OC)cc1]
R₂ is
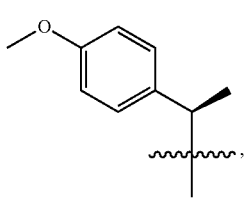 [SMILES: *[C@H](C)c1ccc(OC)cc1]
126
R₃ is
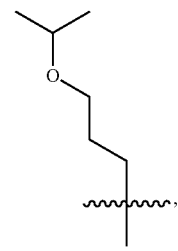 [SMILES: *CCCOC(C)C]
R₄ is
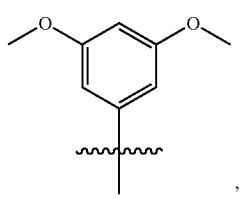
R₅ is
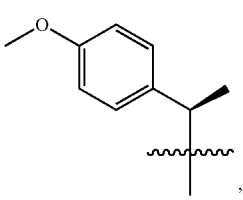
and R₆ is
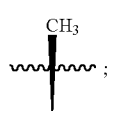;
R₁ is
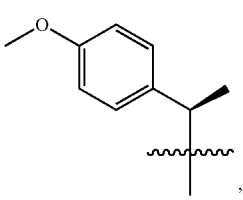

| 127 | 128 |
|---|---|
| R₂ is 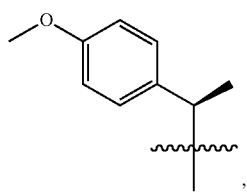 | R₁ is 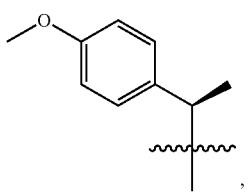 |
| R₃ is 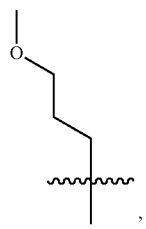 | R₂ is 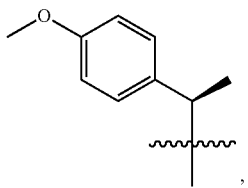 |
| R₄ is 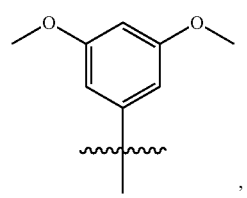 | R₃ is 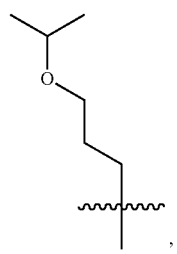 |
| R₅ is 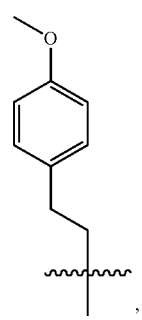 [SMILES: *CCc1ccc(OC)cc1] | R₄ is 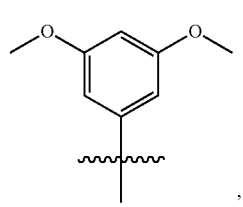 |
| and R₆ is 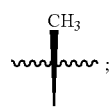 | R₅ is 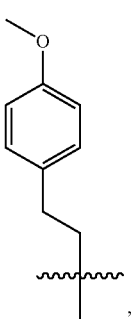 |

129
and R₆ is
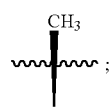;
R₁ is
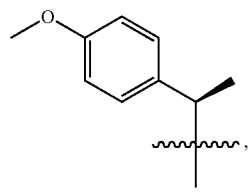 [SMILES: *[C@H](C)c1ccc(OC)cc1],
R₂ is
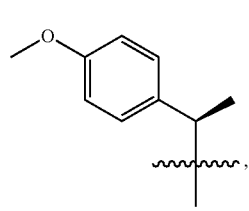 [SMILES: *[C@H](C)c1ccc(OC)cc1],
R₃ is
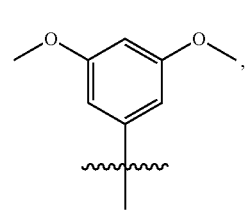,
R₄ is
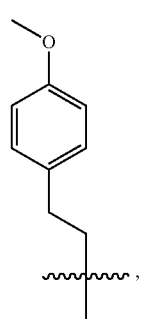 [SMILES: *CCc1ccc(OC)cc1],
130
R₅ is
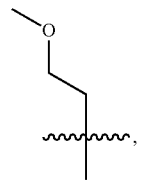 [SMILES: *CCOC],
and R₆ is
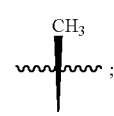;
and
R₁ is
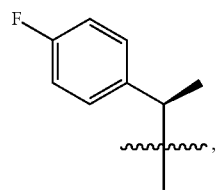 [SMILES: *[C@H](C)c1ccc(F)cc1],
R₂ is
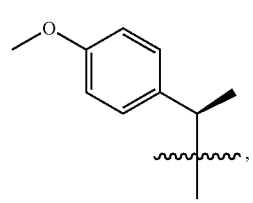 [SMILES: *[C@H](C)c1ccc(OC)cc1],
R₃ is
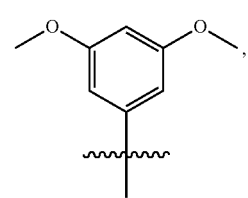,
R₄ is
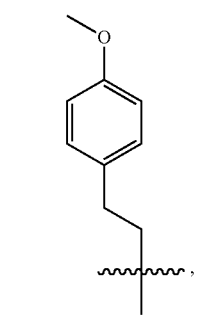 [SMILES: *CCc1ccc(OC)cc1], $R_5$ is

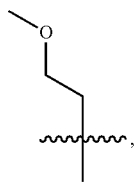 [SMILES: *CCOC]

and $R_6$ is

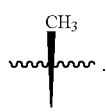

Statement 34. A pharmaceutical composition comprising a pharmaceutically acceptable carrier and a pharmaceutically effective amount of the peptoid-peptide macrocycle of any one of Statements 1-33.
Statement 35. A pharmaceutical composition according to Statement 34, where the carrier is a parenteral, oral, or topical carrier.
Statement 36. A method for preventing, treating, ameliorating or managing a disease or condition which comprises administering to a patient in need of such prevention, treatment, amelioration or management, a prophylactically or therapeutically effective amount of a prophylactically or therapeutically acceptable amount of the peptoid-peptide macrocycle of any of Statements 1-33, or the pharmaceutical composition of either of Statements 34 or 35.
Statement 37. A method according to Statement 36, where the disease or condition is cancer, pulmonary fibrosis, psoriasis, or a combination thereof.
Statement 38. A method according to Statement 37, where the cancer is hepatic cancer, colon cancer, rectal cancer, breast cancer, prostate cancer, skin cancer, head and neck cancer, lung cancer, gastric cancer, mesothelioma, Barrett's esophagus, synovial sarcoma, cervical cancer, endometrial ovarian cancer, Wilm's tumor, bladder cancer, or leukemia.
Statement 39. Use of the peptoid-peptide macrocycle set forth in any one of Statements 1-33 for the preparation of a medicament for the treatment of a disease or condition that is causally related to the aberrant activity of the Wnt signaling pathway in vivo.
Statement 40. Use according to Statement 39, where the disease or condition is cancer or pulmonary fibrosis.
Statement 41. Use according to Statement 39, where the cancer is hepatic cancer, colon cancer, rectal cancer, breast cancer, prostate cancer, skin cancer, head and neck cancer, lung cancer, gastric cancer, mesothelioma, Barrett's esophagus, synovial sarcoma, cervical cancer, endometrial ovarian cancer, Wilm's tumor, bladder cancer, or leukemia.
Statement 42. Use according to Statement 41, where the skin cancer is melanoma, the liver cancer is hepatocellular cancer or hepatoblastoma, and/or the lung cancer is non-small cell lung cancer.
Statement 43. Use according to Statement 39, where the disease or condition is pulmonary fibrosis.
Statement 44. A compound according to any one of Statements 1-33 for use in the treatment of a disease or condition that is causally related to the aberrant activity of the Wnt signaling pathway in vivo.
Statement 45. A peptoid-peptide macrocycle according to any one of Statements 1-11, where the peptoid-peptide macrocycle is chosen from:

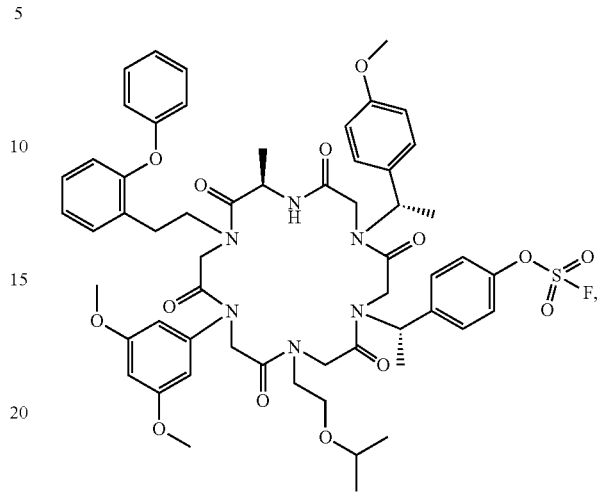

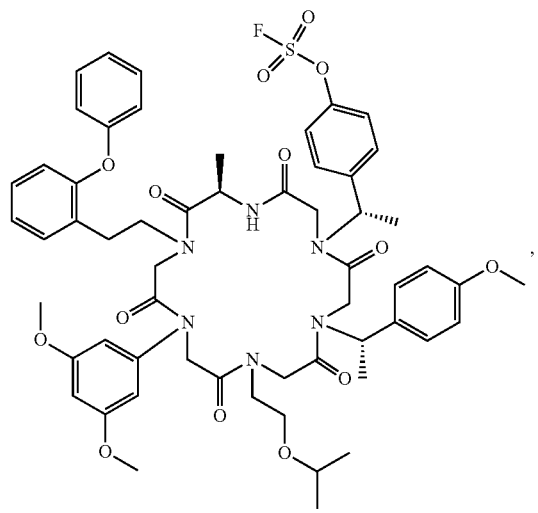

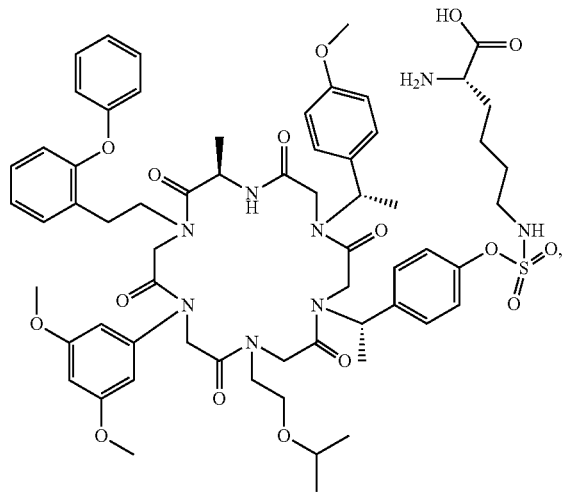

133
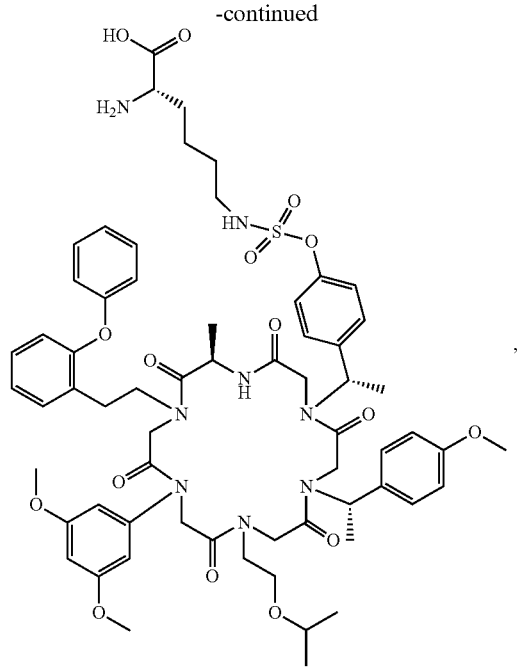
,
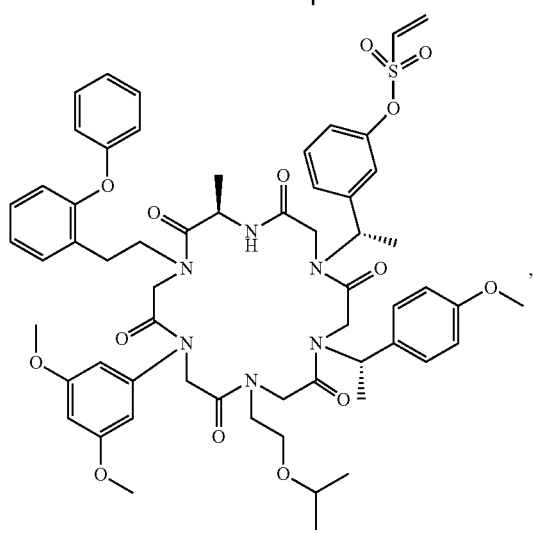
,
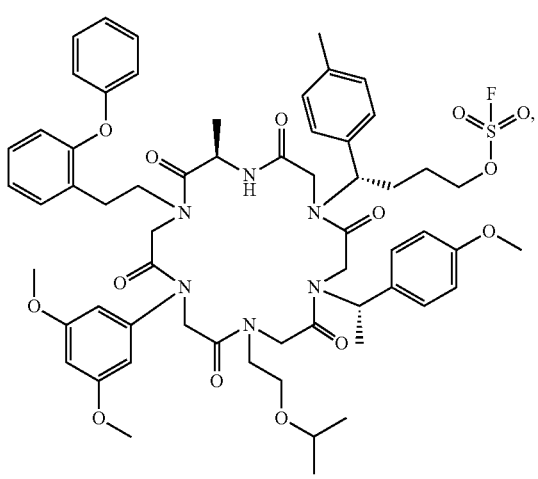
134
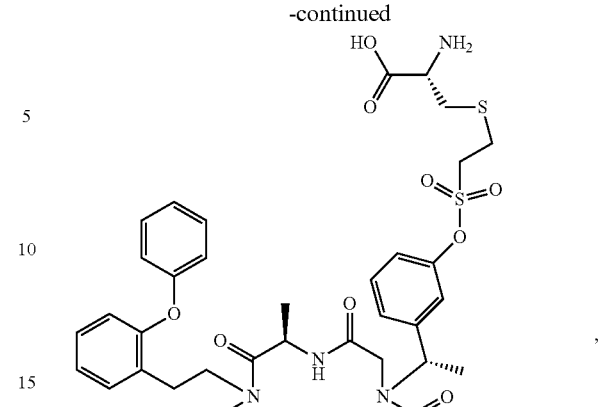
,
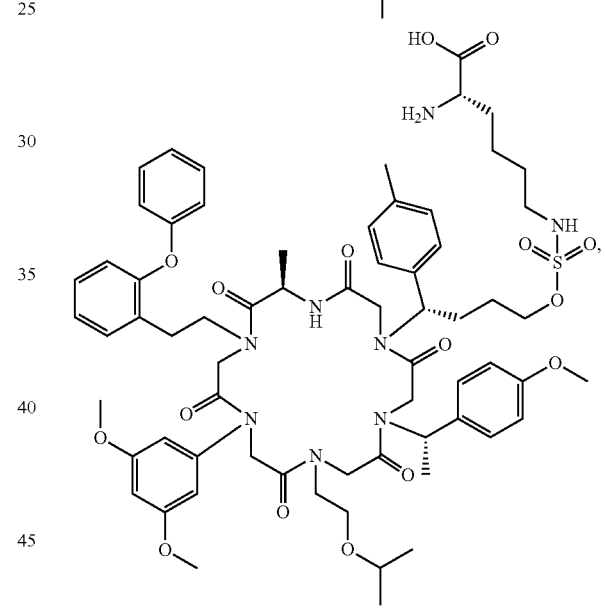
,
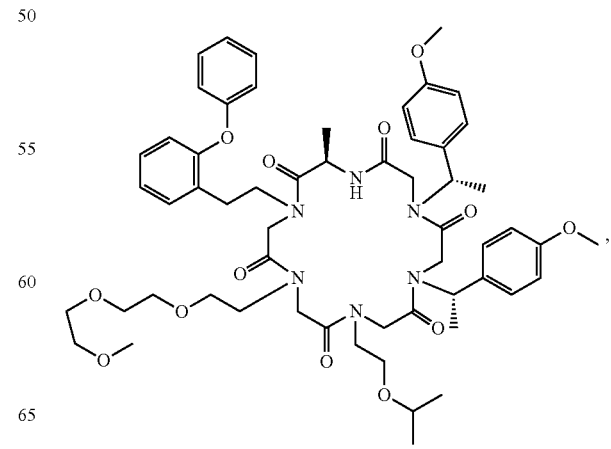

-continued

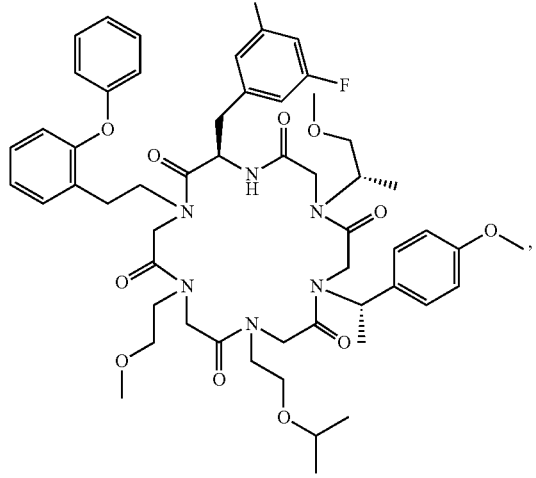

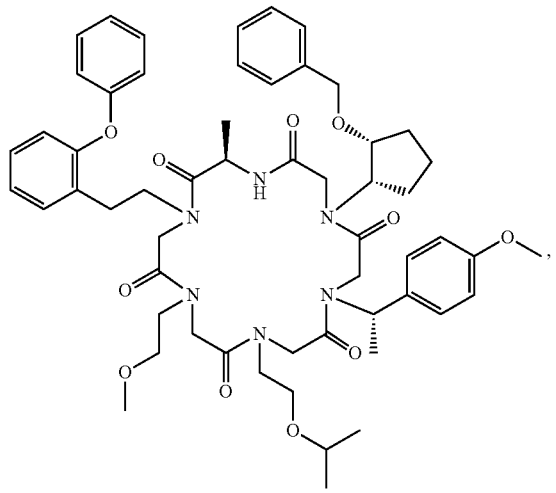

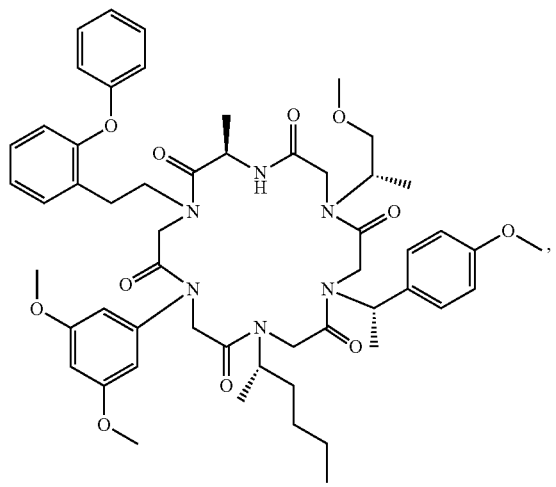

-continued

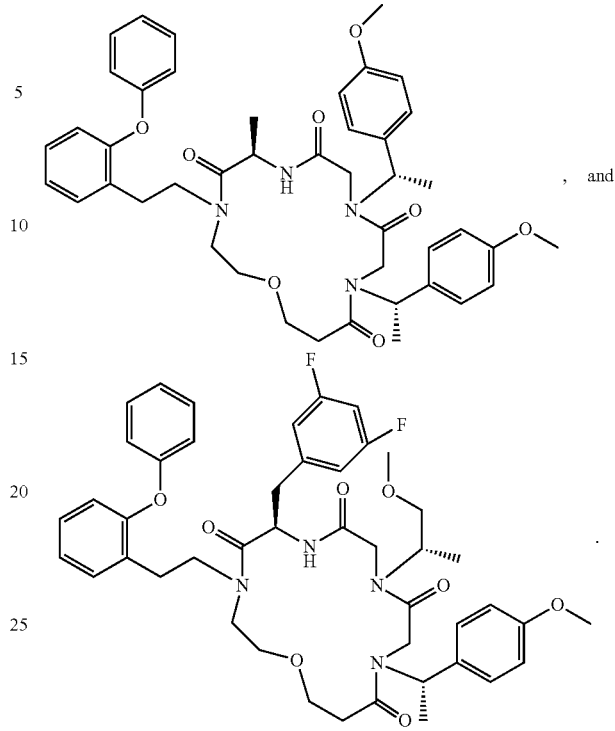

, and

EXAMPLES

The following examples are presented in order to more fully illustrate the present disclosure. They should in no way be construed, however, as limiting the broad scope of the disclosure.

Example 1

Figure 3:
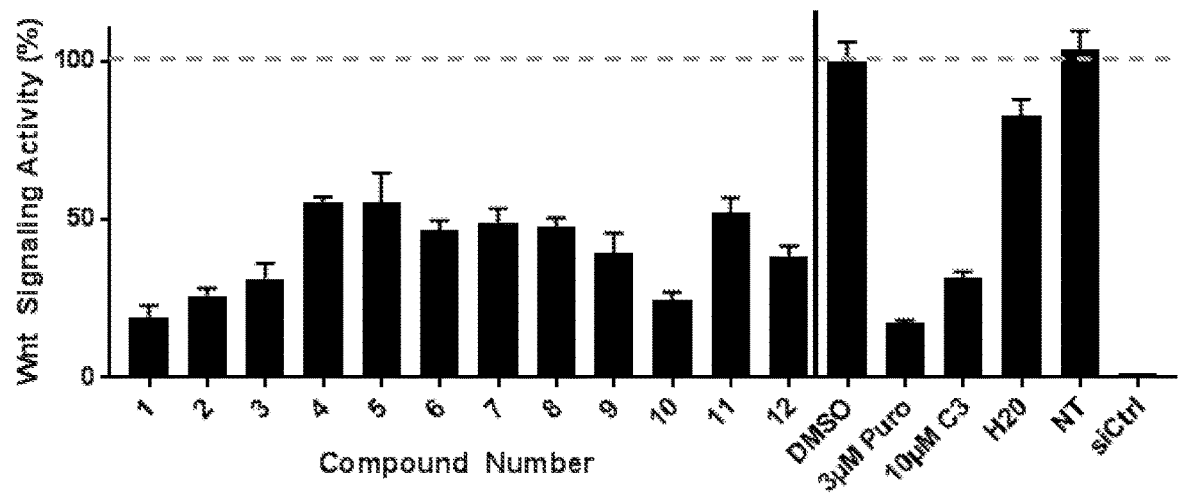
FIG. 3 shows results from a cell based assay designed to identify antagonists of the Wnt signaling pathway. Oligomer compounds of this disclosure (1-12) were administered at 10 micromolar concentration and Wnt signaling activity was monitored after 24 hours. The results are compared to the vehicle alone (DMSO), a cytotoxic agent (Puromyocin, Puro), a previously reported small molecule antagonist of the Wnt signaling pathway (iCRT3), water ($H_2O$), non-treated cells (NT), and a control condition that does not establish activation of the pathway (siCtrl).
Figure 4:
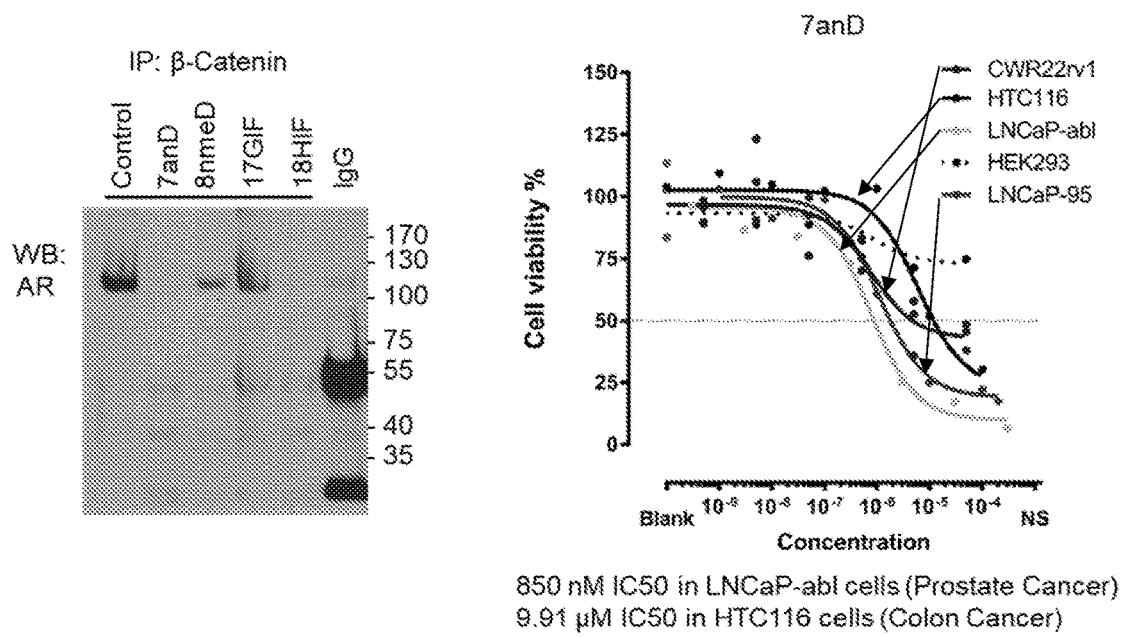
FIG. 4 shows (left panel) co-immunopreciptation (co-IP) of β-catenin and the Androgen Receptor (AR) as visualized by western blot (WB). Cells were incubated with 5 μM of peptoid macrocycles prior to co-IP. Dose response curves for cell viability of one of the best peptoid macrocycles shows destruction of several cell types including prostate and colon cells, as well as HEK293cells assess general toxicity (right panel).

The macrocycles were evaluated for their ability to inhibit the Wnt signaling pathway in cell culture. The macrocycles were administered at a concentration of 10 micromolar, and the activity was monitored with a luciferase reporter assay responsive to signaling through the Wnt pathway. All compounds were observed to be highly potent in the cell-based assay at 24 hours after dosing (FIG. 3). The macrocycles were also observed to exert minimal cellular toxicity at the 10 micromolar concentration. FIG. 4 (left panel) shows co-immunoprecipitation (co-IP) of β-catenin and the Androgen Receptor (AR) as revealed by western blot analysis. Cells were incubated with 5 μM of peptoid macrocycles prior to co-IP. FIG. 4 (right panel) depicts dose response curves for cell viability of one of the best peptoid macrocycles, which shows toxicity towards several cell types including prostate and colon cancer cells, as well as HEK293 cells, which are included to assess non-specific toxicity of the peptoid macrocycle.

Example 2

The following example describes peptoids of the present disclosure, methods of making same, and uses for same.

In this disclosure, computational protein design protocols were applied to design macrocyclic peptoid-peptide hybrids to target the N-terminal TCF β-hairpin binding pocket of β-catenin and demonstrate its potential for use as a therapeutic in prostate cancer models. As a demonstration of computational modeling and in silico design of bioactive peptoid-peptide hybrid macrocycles, targeting of a PPI in the Wnt signaling pathway was sought. Using the Rosetta suite of computational tools, a small library of peptoid-peptide macrocycles designed in silico that were predicted to bind β-catenin were designed. Cell culture based luciferase assays were used to test the oligomers and select a lead compound. At least one macrocycle was shown to potently inhibit binding between β-catenin and TCF proteins. The macrocycle also inhibited the proliferation of prostate cancer cells with nano-molar $IC_{50}$ values in both 2D and 3D cell culture models. In addition, it was demonstrated that the macrocycle inhibits Wnt signaling in vivo through a zebrafish model.

Results—Design of oligomer macrocycles to bind β-catenin—A cleft on the surface of β-catenin created by armadillo repeats 8, 9, and 10 (FIG. 5), which was suitable for targeting with a cyclic oligomer, was identified. This region includes the binding site between β-catenin and the N-terminal sequence of Xenopus laevis TCF3, which forms a β-hairpin structure at the site of interaction in the X-ray structure (PDBid: 1G3J). This cleft is also adjacent to the $G_{13}ANDE_{17}$ (SEQ ID NO:14) region of the human hTCF4 β-catenin binding sequence which had been mimicked in other efforts towards inhibiting the β-catenin:TCF4 interaction.

Figure 6:
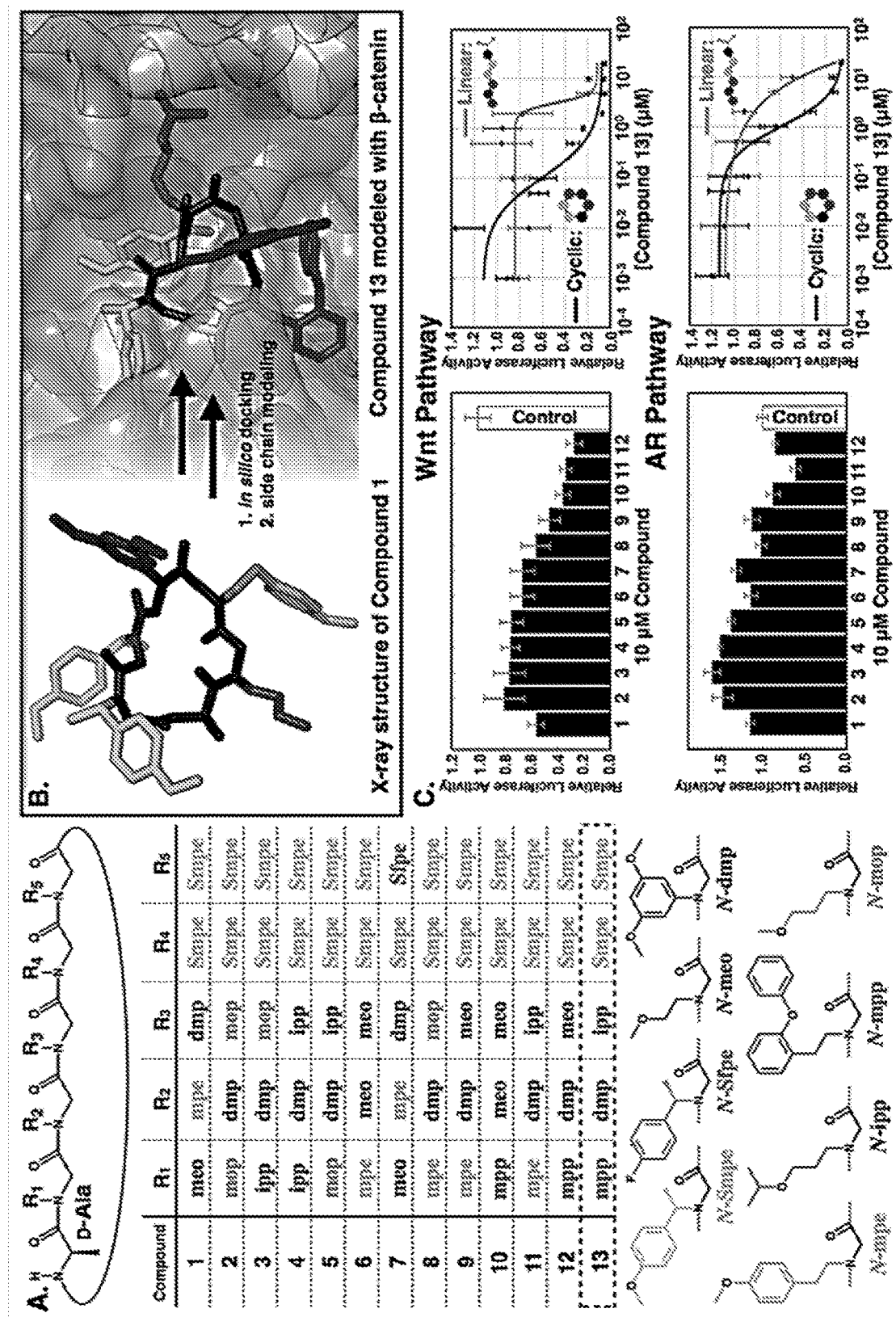
FIG. 6 shows (A) peptoid-peptide hybrid macrocycle backbone scaffold. Middle table details compound number list and chemical compositions. Bottom section details the chemical compositions of peptoid side chains. (B) X-ray structure of the Compound 1 starting scaffold along with a model of Compound 13 docked into the N-terminal TCF binding region of β-catenin. (C) Luciferase reporter assay of compounds relative to a 'vehicle' control. Notes: "N-meo": N-(methoxy-ethyl)-glycine, "N-mpe": N-(4-methoxy-phenyl-ethyl)-glycine, "N-dmp": N-(3,5-dimethoxy-phenyl)-glycine, "N-Smpe": N—((S)-4-methoxy-phenyl-ethyl)-glycine, "N-Sfpe": N—((S)-4-fluoro-phenyl-ethyl)-glycine, "N-mpp": N-(2-phenoxy-phenyl-ethyl)-glycine, "N-ipp": N-(isopropoxy-propyl)-glycine, "N-mop": N-(methoxy-propyl)-glycine.

Rational design techniques were applied to target the xTCF3 β-hairpin binding pocket of β-catenin. In order to identify suitable oligomer scaffolds, high-resolution structures experimentally determined for a set of peptoid and peptoid-α-amino acid hybrid macrocyclic structures were evaluated. One cyclic hexamer peptoid-α-amino acid hybrid (18-atom macrocycle Compound 1, FIG. 6B) was observed to provide a favorable steric compliment to the targeted β-catenin cleft after modeling with the Rosetta molecular design suite. The in silico AGbinding values were evaluated after several iterations of guided (PyMOL, Schrödinger) and automated docking protocols.

Inspection of the X-ray structure of 1 (FIG. 6B) suggested that the D-Alanine and "N-Smpe" residues played a critical role in directing the overall fold of the oligomer. It is hypothesized that these bulky α-chiral peptoid side chains and a D-amino acid confer a unique structure of the oligomer backbone (FIG. 6B, positions colored green and black, respectively). In contrast, positions $R_1$, $R_2$ and $R_3$ appeared relatively amenable for substitution to optimize complementarity to the protein surface. After thorough analysis of 1 docked into the β-catenin X-ray structure, a set of side chain types at each of the designable positions was chosen based on a combination of visual inspection, modeling, aqueous solubility, and synthetic feasibility, as well as properties considered favorable for cell-permeability Compound testing and identification of a hit compound—Using a TOP-Flash Wnt luciferase reporter, 12 oligomers identified from in silico modeling for inhibitory activity (FIG. 6A) were tested. At 10 mM concentration, all compounds had some level of Wnt inhibitory activity in cell culture, with varying degrees of efficacy. Also employed was a 3×-Androgen Response Element (ARE) luciferase reporter to measure the effect on AR activity. Only a few of the compounds were effective at inhibiting AR signaling, the best of which were also the most effective at inhibiting Wnt signaling. Based on the inhibitory data from other compounds containing similar side chain types, it was reasoned that if a macrocycle with the "N-ipp" side chain in position $R_3$ and the "N-mpp" side chain in position $R_1$ (FIG. 6A) was generated, it may create a more potent compound. An optimal sequence composed of these monomer types resulted in our 'hit' oligomer compound 13. The hit compound was in fact more effective at inhibiting both the Wnt and AR luciferase reporters. FIG. 2B depicts the predicted structure and contacts of the β-catenin: 13 complex.

Figure 7:
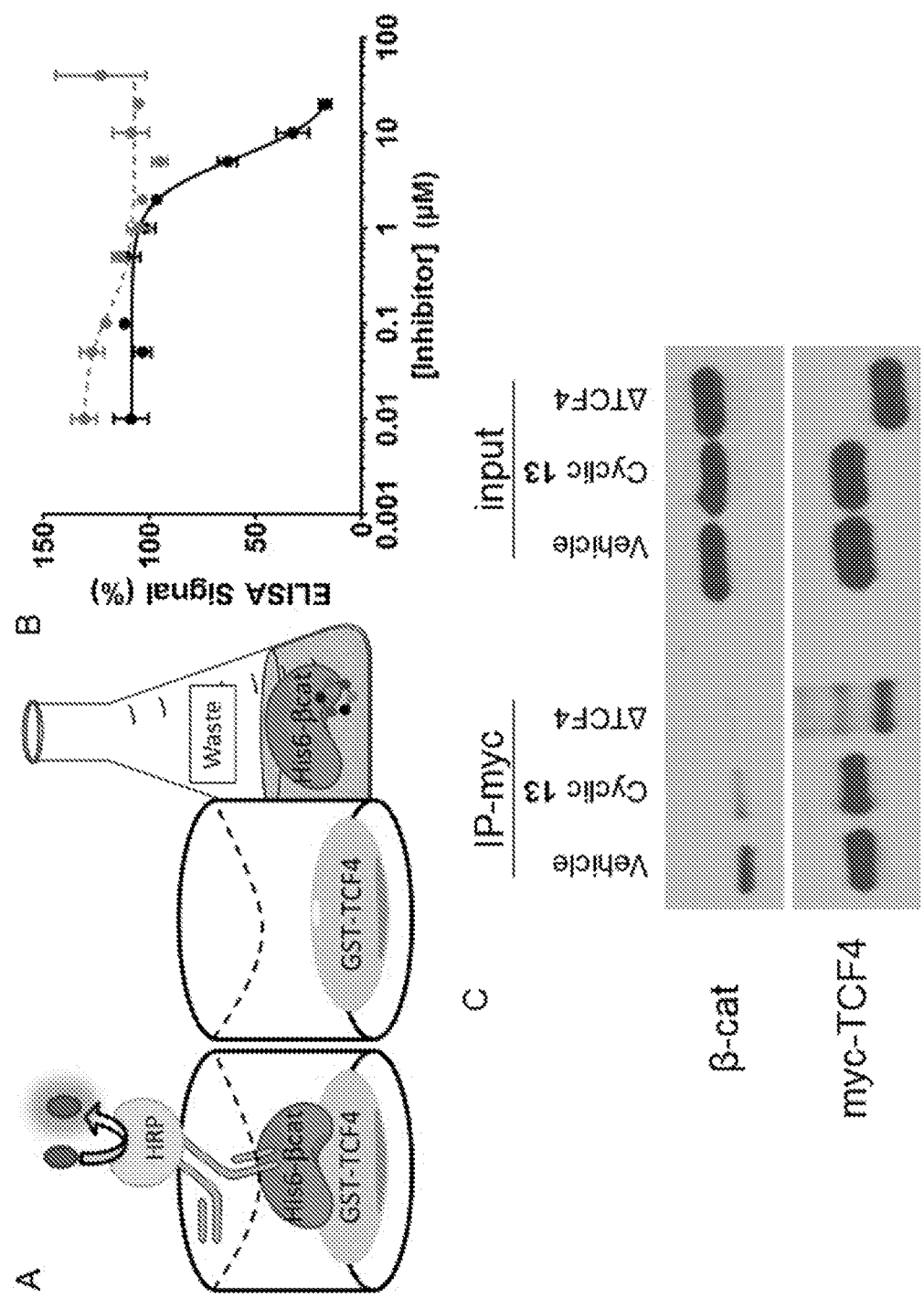
FIG. 7 shows the peptoid macrocycle inhibits the β-catenin:TCF4 interaction. (A) Schematic for ELISA-based detection of recombinant $His_6$-β-catenin binding to a GST-TCF4 N-terminal Catenin Binding Domain fusion protein (B) Dose response curves for the cyclic oligomer (black solid line) and linear oligomer (grey dashed line) in the ELISA assay (C) Western blot depicting a co-immunoprecipitation (IP) for myc-TCF4 and β-catenin treated with compound. ATCF4: A myc-TCF4 construct that lacks the β-catenin binding domain.

The hit oligomer macrocycle inhibits Wnt and AR signaling—The dose response curves for the hit compound 13 in the Wnt and AR luciferase reporters were characterized. The linear version of 13 (linear 13: $NH_2$-D-Ala-N-mpp, N-dmp, N-ipp, N-Smpe, N-Smpe-OH) was used as a control compound. It incorporates the identical chemical moieties as its cyclic counterpart, but is likely not arranged in an optimal binding conformation and was therefore anticipated to demonstrate weaker affinity. Indeed, as observed in luciferase assays (FIG. 6C), the $IC_{50}$ for Wnt luciferase inhibition was 0.105 μM+/−0.040 for 13 compared to 3.27 μM+/−0.99 for the linear oligomer. Compound 13 also showed better inhibition of the AR luciferase reporter ($IC_{50}$ of 1.02 μM+/−0.20) compared to linear 13 ($IC_{50}$ 7.63 μM+/−1.22). While these values may suggest that the compounds inhibit Wnt signaling with increased potency relative to the AR pathway, the experimental conditions used with each reporter, including siRNA knockdown of APC to activate the Wnt reporter and DHT treatment to activate AR signaling, confound direct comparison of the values. To confirm that 13 does inhibit the β-catenin:TCF protein interaction, we developed a sandwich ELISA that detected recombinant β-catenin binding to a peptide containing the TCF4 N-terminal β-catenin binding domain (FIG. 7A). In this assay, 13 inhibited binding with an $IC_{50}$ of 5.44 μM+/−0.82 (FIG. 7B). Inhibition of β-catenin:TCF4 protein interaction was also confirmed in cell culture. HEK293 cells were transiently transfected with a plasmid expressing full length, myc-tagged TCF4. After 48 hour treatment with either DMSO or 10 μM 13, cells were lysed and myc-TCF4 protein was immunoprecipitated. Western blotting was performed, revealing that endogenous β-catenin was co-immunoprecipitated. The β-catenin:TCF interaction was decreased in cells treated with 13 compared to DMSO treated cells (FIG. 7C).

Figure 8:
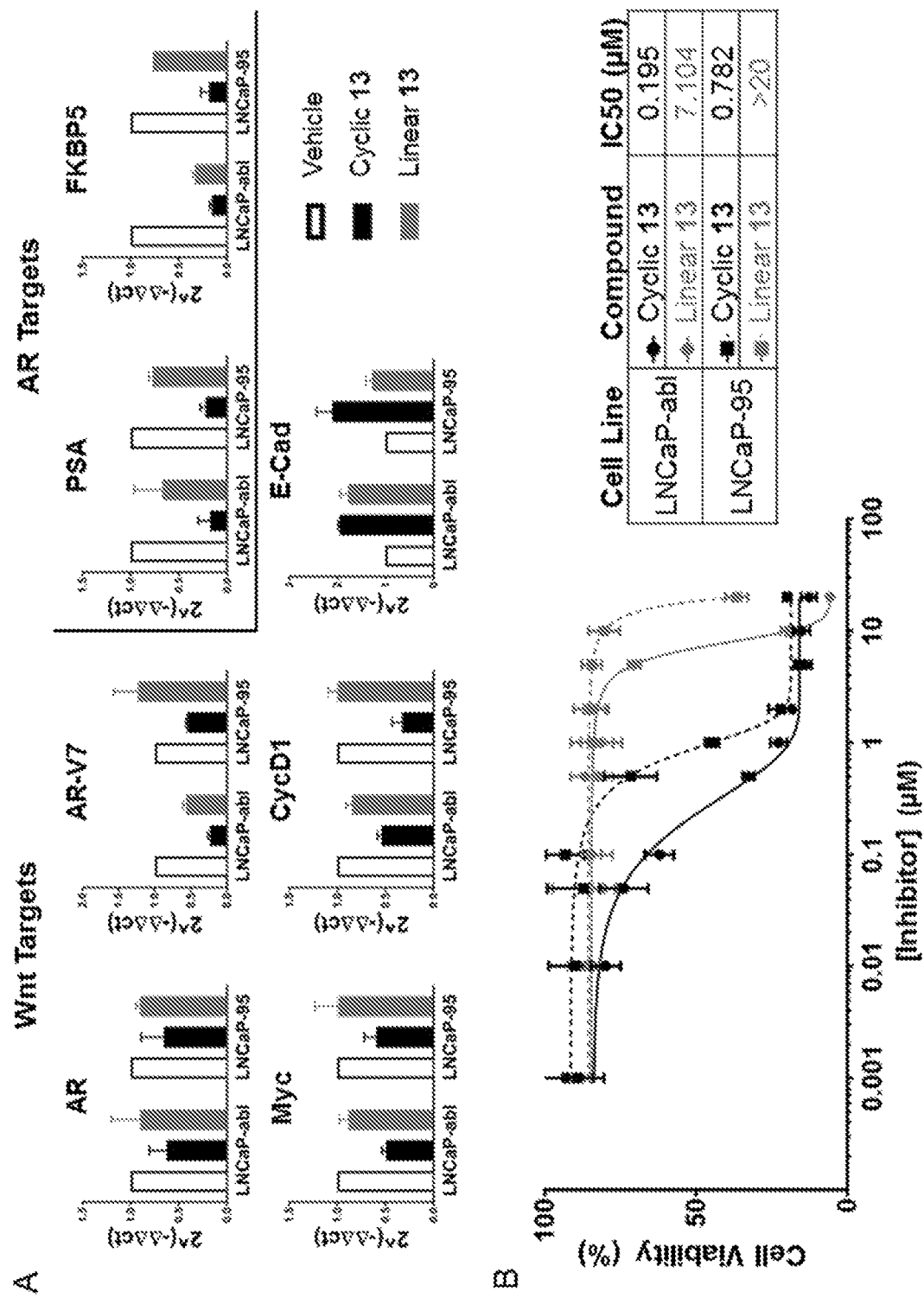
FIG. 8 shows the peptoid affects prostate cancer cell lines. (A) RT-qPCR of mRNA collected from LNCaP-abl or LNCaP-95 cells treated with 10 μM cyclic (black) or 10 μM linear (grey) oligomer for 24 hours. (B) Cell viability measurements using CellTiter-Fluor reagent with 5 day oligomer treatment.

The hit oligomer macrocycle inhibits prostate cancer cell growth—To test the effect of 13 in prostate cancer, we used the LNCaP-abl and LNCaP-95 cell lines. These cell lines were derived from androgen-sensitive LNCaP cells, and passaged in androgen-deprived media to mimic the development of castration resistance in patient tumors. mRNA from LNCaP-abl and LNCaP-95 cells treated with DMSO (vehicle) was isolated, 10 μM 13 and linear 13 for 24 hours to check the expression of endogenous Wnt and AR target genes (FIG. 8A). The mRNA of Wnt target genes cMYC, Cyclin D1, and the AR were all decreased. Transcription of E-cadherin, which has been found to be repressed by Wnt signaling, increased following treatment by 13. AR target genes PSA and FKBP5 mRNA were also decreased. In addition, the transcription of an AR splice variant, AR-V7, which lacks the ligand binding domain and as a consequence is constitutively active, was also decreased. AR-V7 is particularly challenging to target as most AR antagonists target the ligand binding domain. Similar to experiments discussed above, the macrocycle again showed increased potency in transcriptional modulation compared to its linear analog. To check if the changes in Wnt and AR target gene expression translated into effects on growth, the viability of LNCaP-abl and LNCaP-95 cells was determined after five days of treatment (FIG. 8B). Compound 13 inhibited proliferation with an $IC_{50}$ of 195 nM+/−52 (LNCaP-abl) and 782 nM+/−34 (LNCaP-95).

Figure 9:
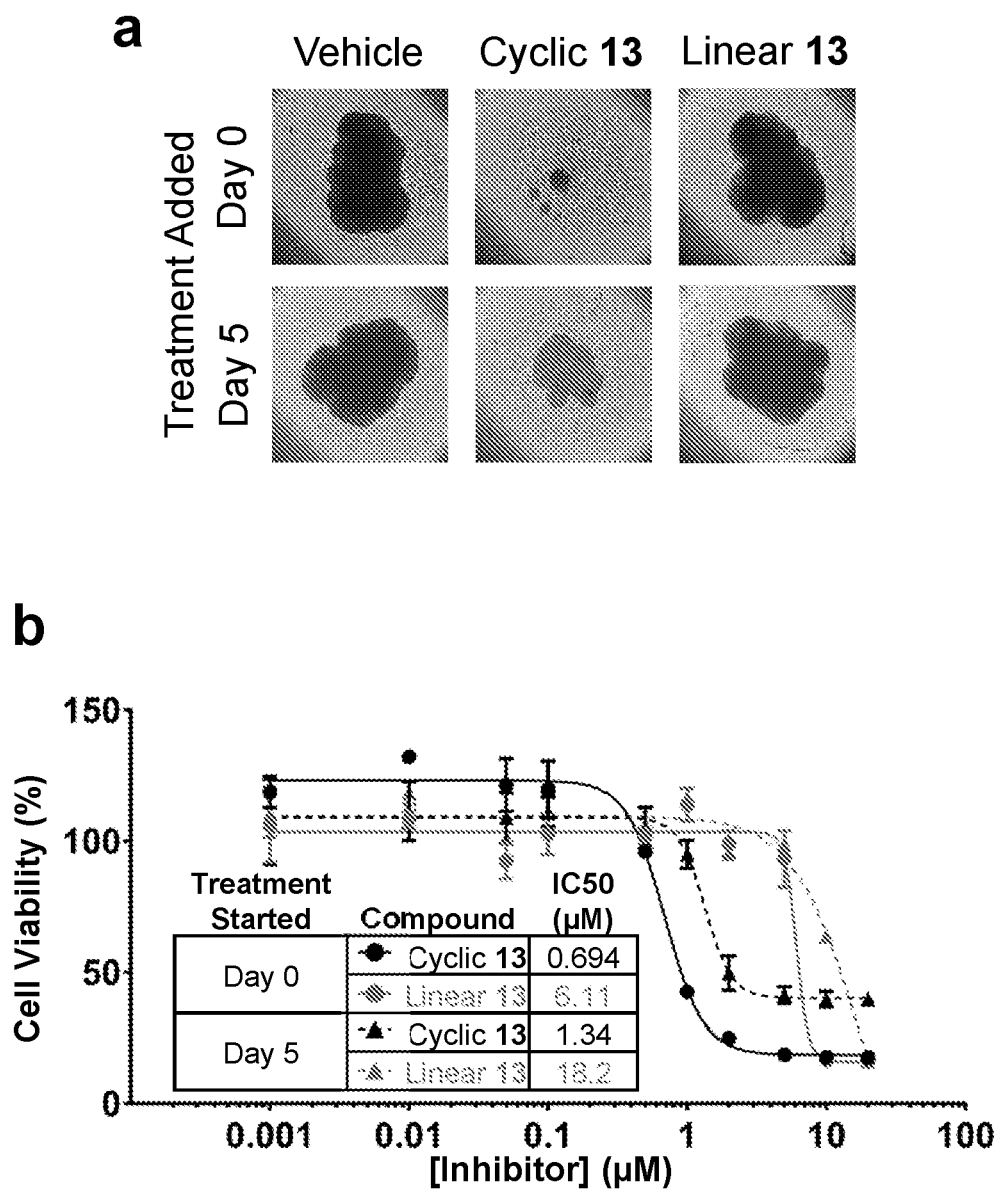
FIG. 9 shows the peptoid macrocycle slows prostate cancer spheroid cell growth. (A) Representative images of tumor spheroids imaged from above on day 20 and treated with vehicle or 2 μM oligomer. (B) End point viability measurements taken on day 22 using PrestoBlue. (C-F) Time course of spheroid areas calculated from images taken throughout the experiment.
Figure 9:
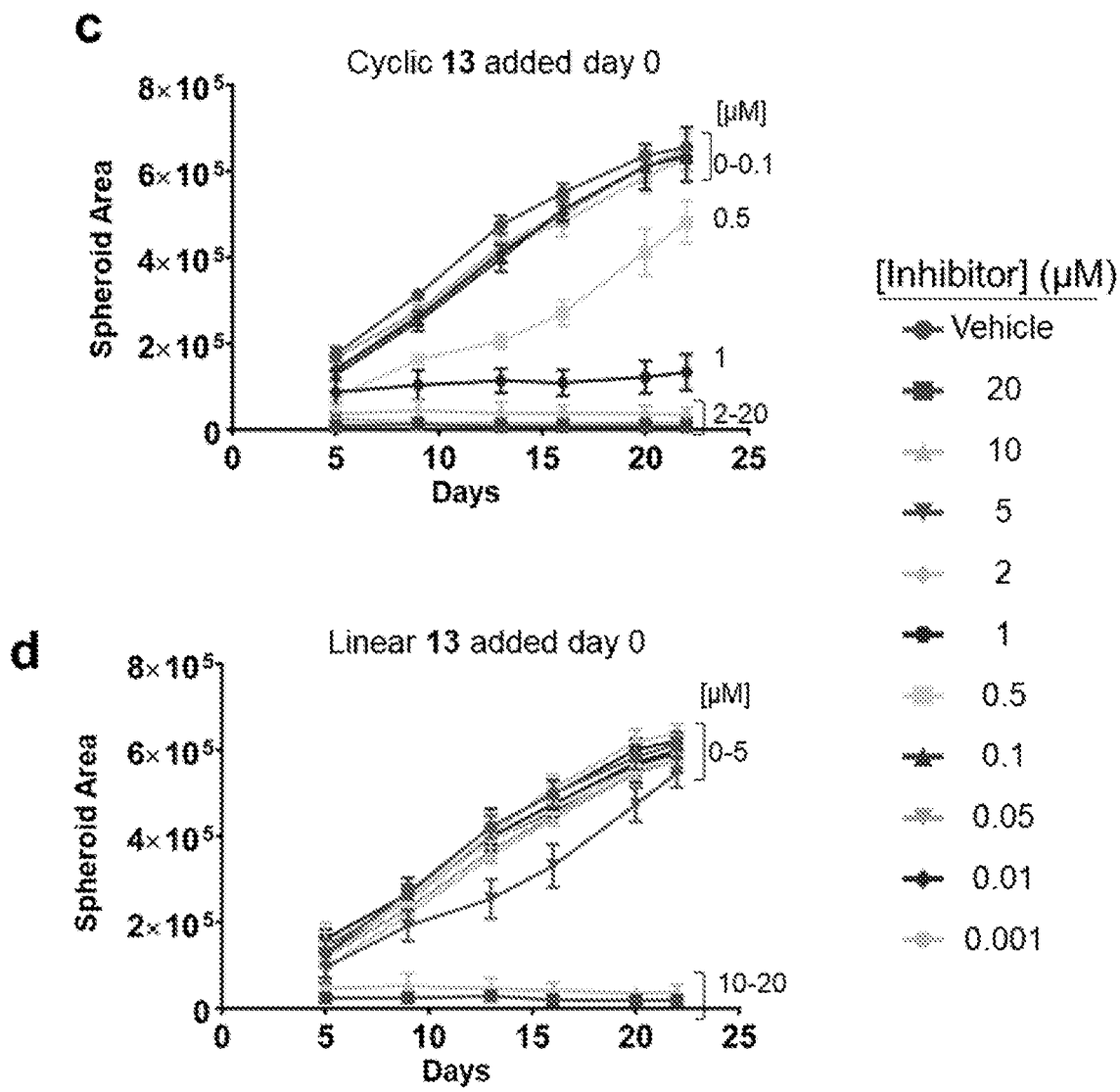
Figure 9:
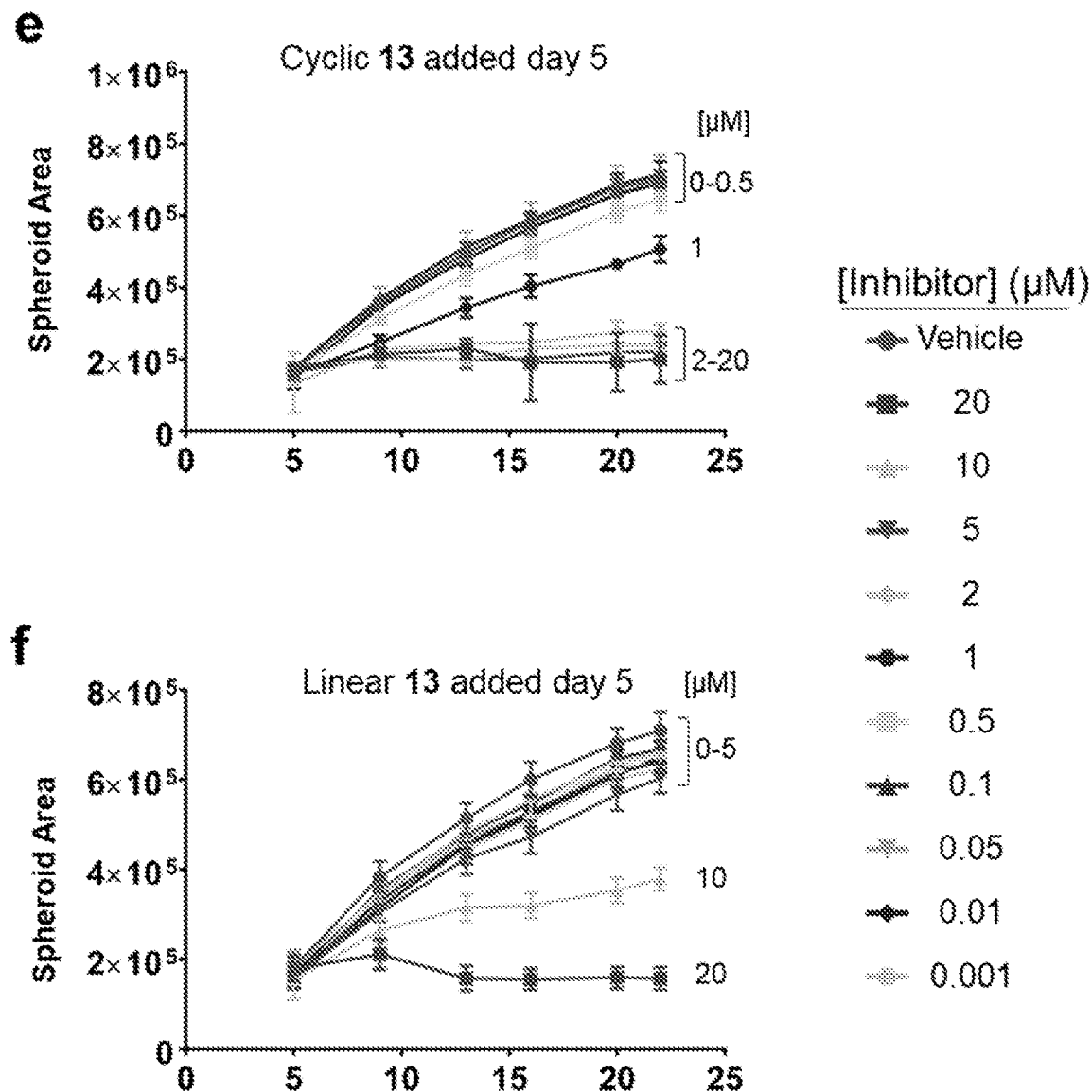

Growth of prostate cancer spheroids is slowed by the hit oligomer macrocycle—To evaluate the impact of the compounds under 3D cell culture conditions thought to be more representative of tumors, LNCaP-abl cells were grown in low attachment plates. The effects on spheroid formation and growth were evaluated following treatment with DMSO, 13, or linear 13 administered at the time of seeding at low cell density in a 384 well plate. In a separate experiment, to test the impact on pre-formed spheroids, cells were treated five days after initial seeding. Spheroids from both experiments were grown for 22 days, with compound refreshed on days 5, 9, 13, 16, and 20. FIG. 9A shows representative images of cells treated with DMSO, 2 µM 13, or 2 µM linear 13 at 20 days. PrestoBlue was used to measure cell viability on day 22 (FIG. 9B). Compound 13 reduced spheroid proliferation with an $IC_{50}$ of 0.694 µM+/−0.037when added in the initial seeding (Day 0). It also reduced spheroid proliferation when added on day 5, with somewhat lower potency and efficacy and an $IC_{50}$ of 1.34 µM+/−0.11. FIG. 9C-F depicts spheroid area over time based on size measurements from the images taken throughout the experiment. Higher concentrations of compound 13 (20 µM, 10 µM, 5 µM, 2 µM and 1 µM) prevented spheroid formation when added on day 0 with seeding and 0.5 µM 13 also slowed the growth (FIG. 9C). Concentrations of 13 between 0.001 UM and 0.1 µM had little effect. In the case of compound addition to previously formed spheroids (treatment started at day 5), concentrations of 13 at or above 2 µM stalled the growth of preformed spheroids but caused less of a decrease in spheroid area (FIG. 9E) than addition at day 0. The linear 13 compound had similar effects but with significantly reduced potency (FIGS. 9D and 9F).

Figure 10:
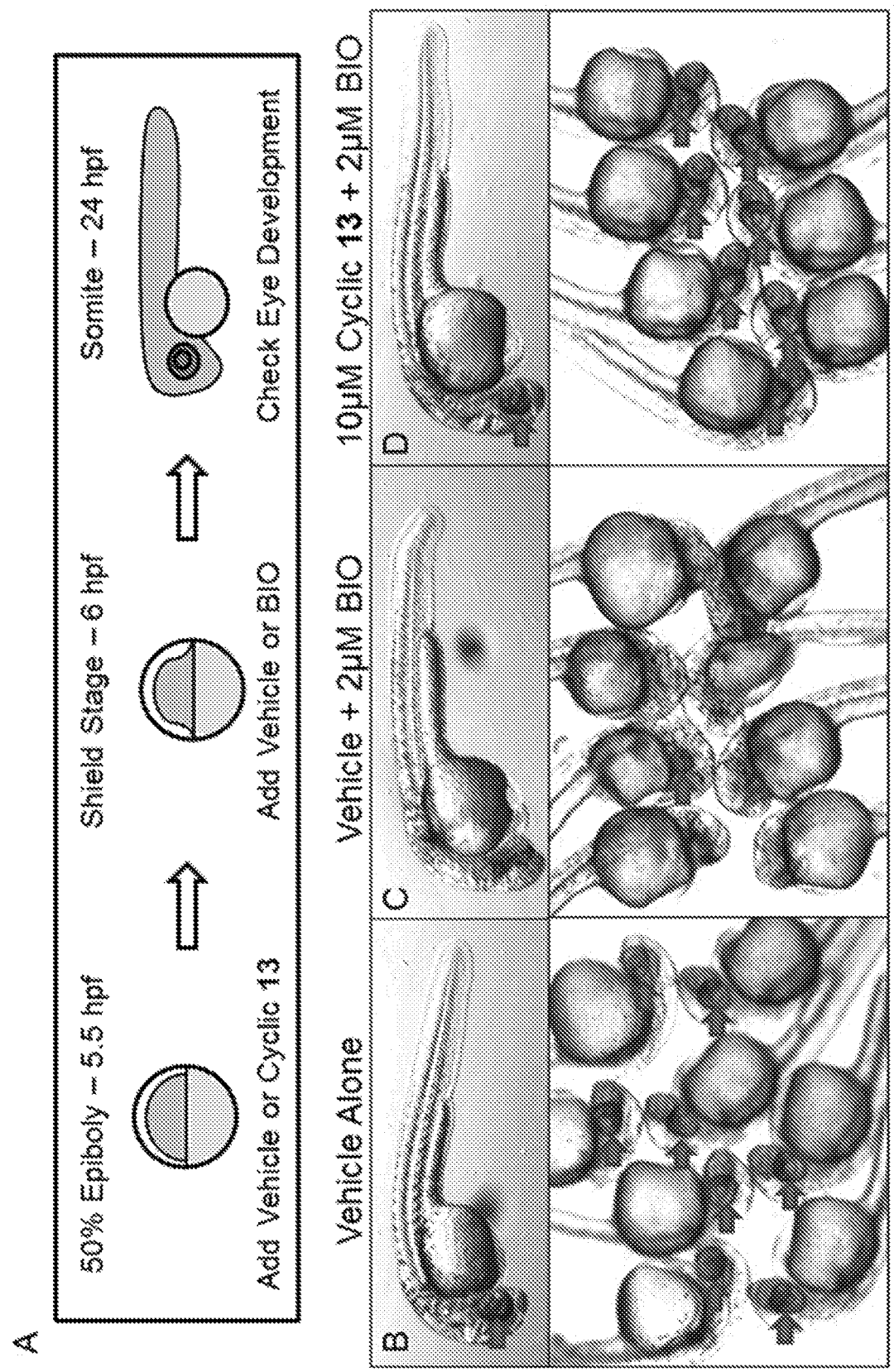
FIG. 10 shows Zebrafish phenotypic assay of Wnt signaling. (A) Schematic for experimental design. (B-D) Images of 24 hour post-fertilization of zebrafish embryos treated with vehicle alone (B), vehicle plus the small molecule "BIO" to activate Wnt signaling (C), or oligomeric macrocycle inhibitor in combination with BIO (D). Arrows point to developing eye structures. The presence of BIO activates Wnt signaling and disrupts typical development of eye structures. The addition of the oligomeric macrocycle abrogates Wnt signaling and restores eye development.
Figure 11:
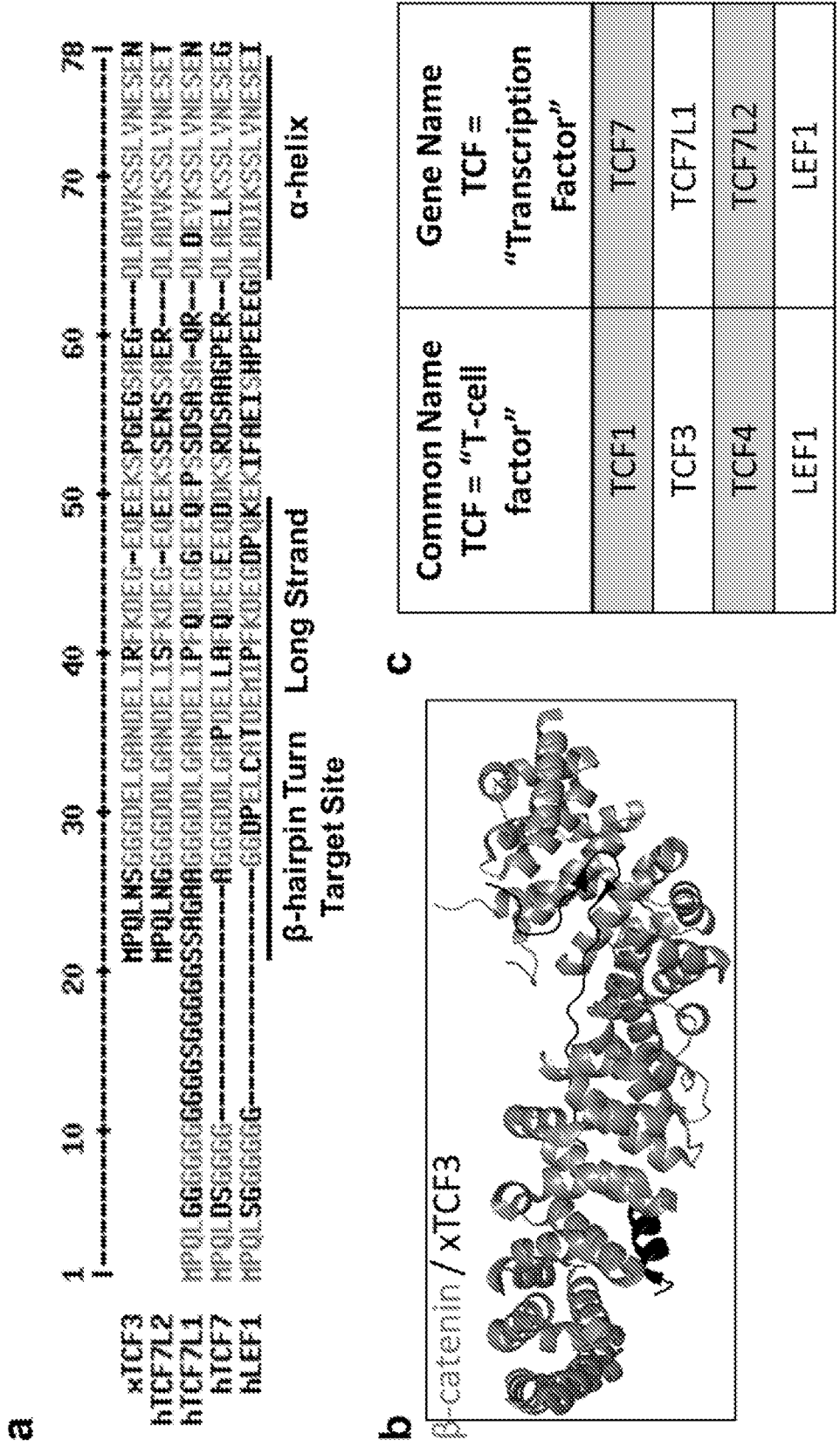
FIG. 11 shows (A) sequence alignment of the catenin binding domains for human TCF/LEF family members with *xenopus* TCF3. The following amino acid sequences are described in (A) MPQLNSGGGDELGANDELIRFKDEG (SEQ ID NO:1), EQEEKSPGEGSAEG (SEQ ID NO:2), DLADVKSSLVNESEN (SEQ ID NO:3), MPQLNGGGGDDLGANDELISFKDEG (SEQ ID NO:4), EQEEKSSENSSAER (SEQ ID NO:5), DLADVKSSLVNESET (SEQ ID NO:6), MPQLGGGGGGGGGSGGGGGS-SAGAAGGGDDLGANDELIPFQDEGGEEQEPSSDS ASA (SEQ ID NO:7), DLDEVKSSLVNESEN (SEQ ID NO:8), MPQLDSGGGG (SEQ ID NO:9), AGGGDDL-GAPDELLAFQDEGEEQDDKSRDSAAGPER (SEQ ID NO:10), DLAELKSSLVNESEG (SEQ ID NO:11), MPQLSGGGGGG (SEQ ID NO:12), and GGDPELCAT-DEMIPFKDEGDPQKEKIFAEISHPEEEGDLADIKSSL VNESEI (SEQ ID NO:13). (B) Code for comparing common TCF/LEF "T-Cell Factor" names to "Transcription Factor" gene names.
Figure 12:
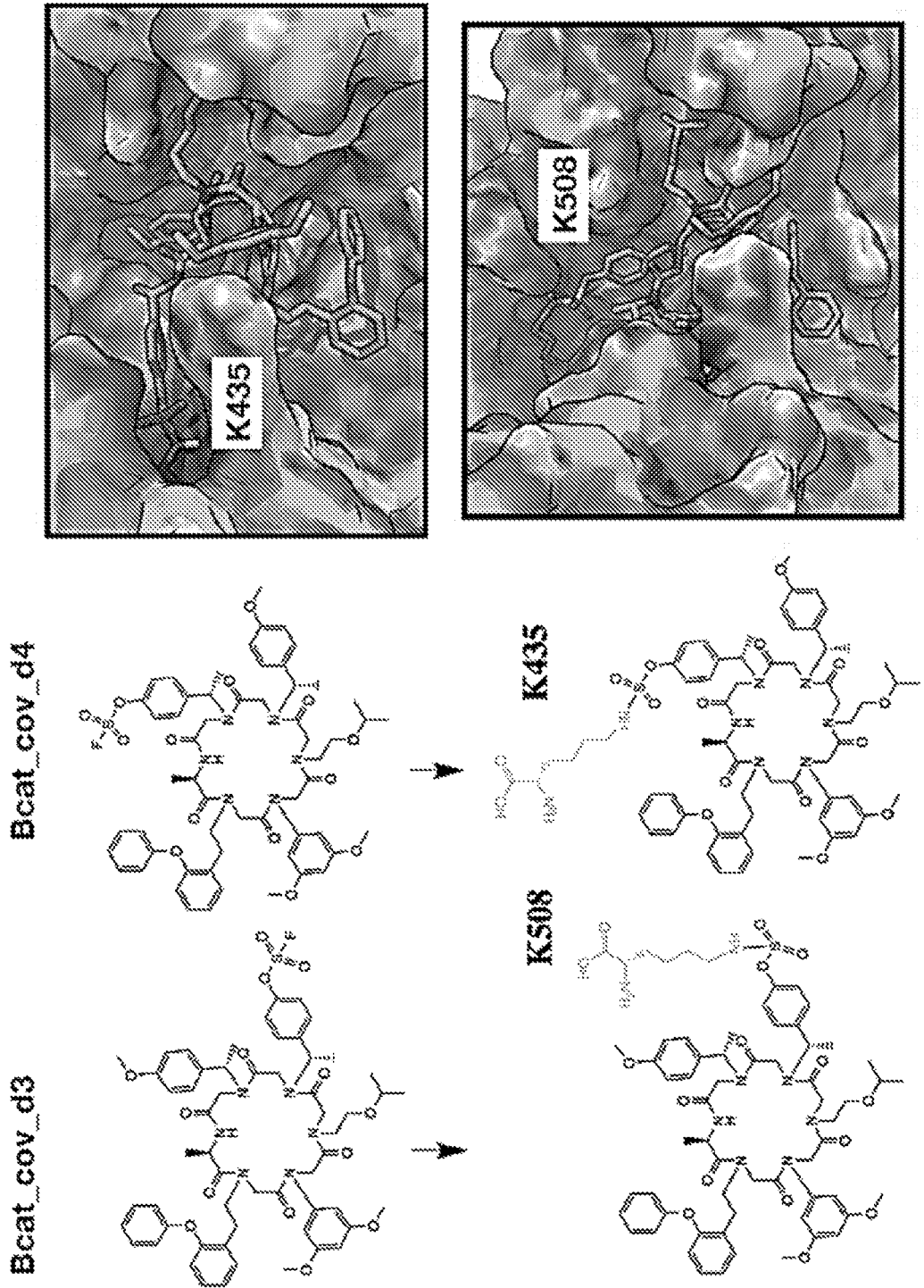
FIG. 12 shows covalent B-catenin binder design.
Figure 13:
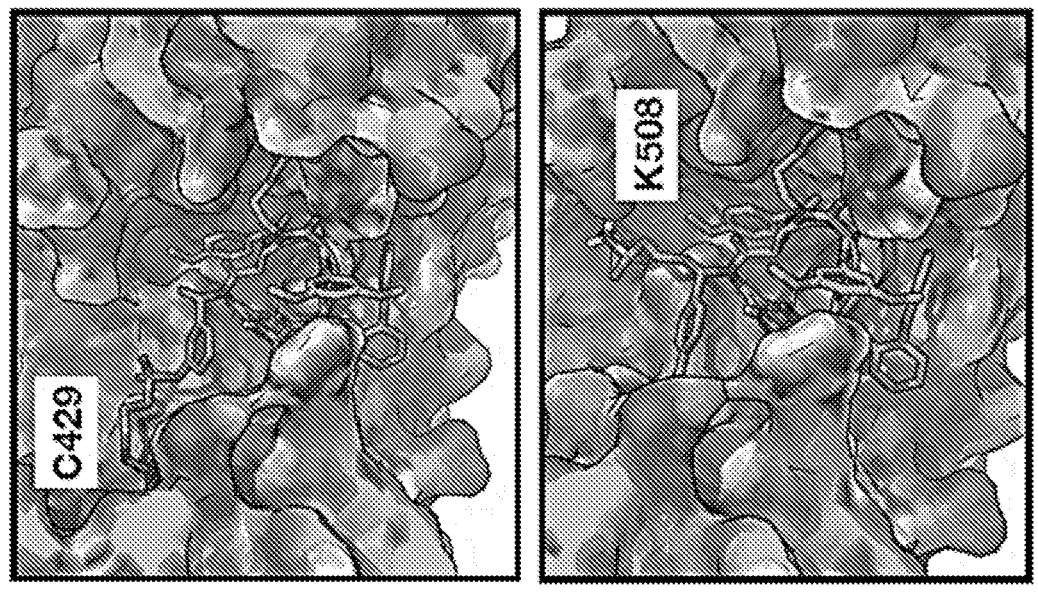
FIG. 13 shows covalent B-catenin binder design.
Figure 13:
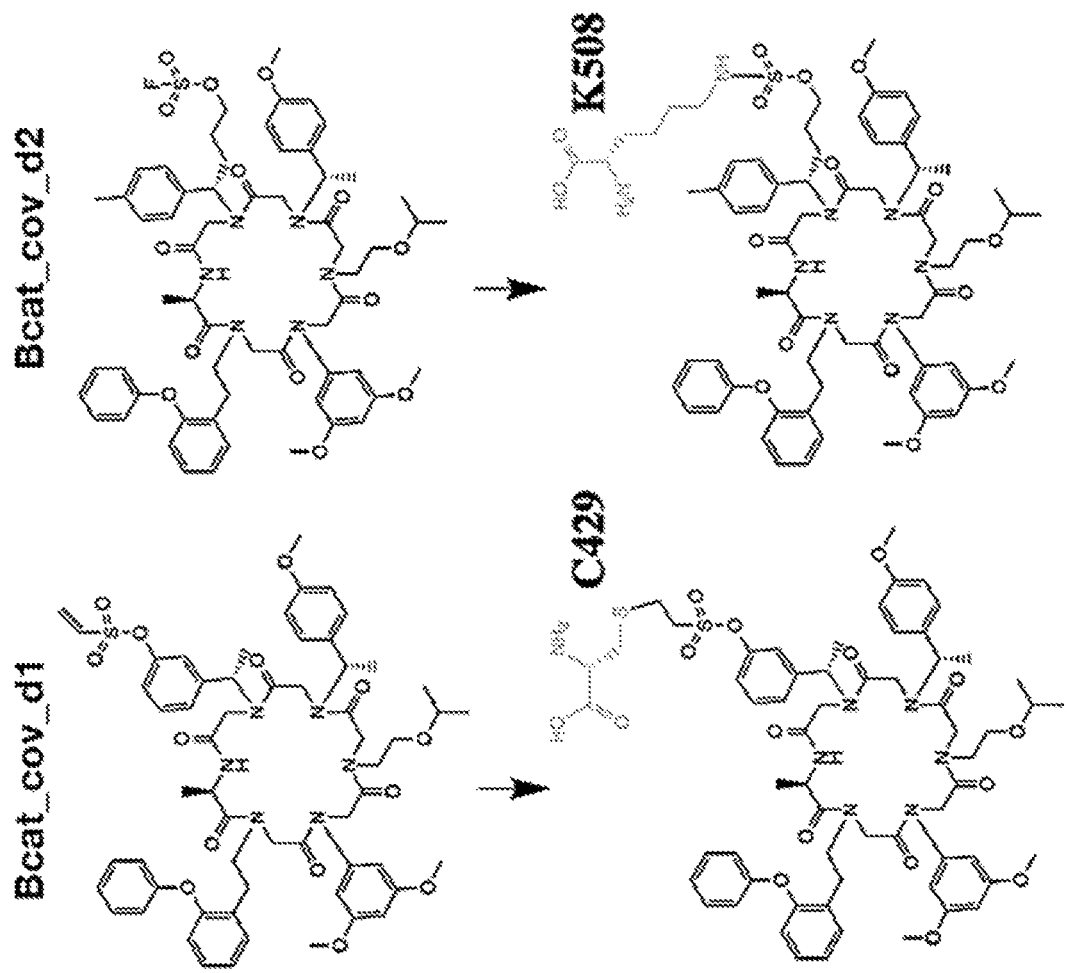
Figure 15:
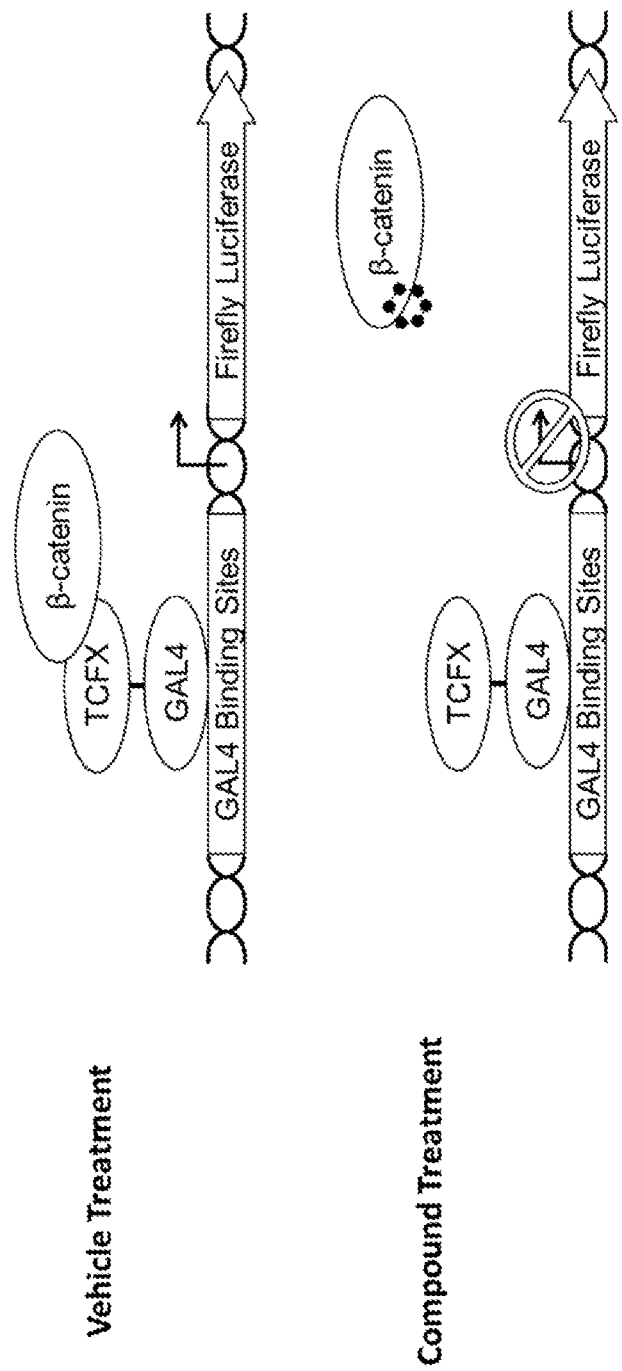
FIG. 15 shows a two-hybrid like assay to examine β-catenin:TCF family member interactions.
Figure 16:
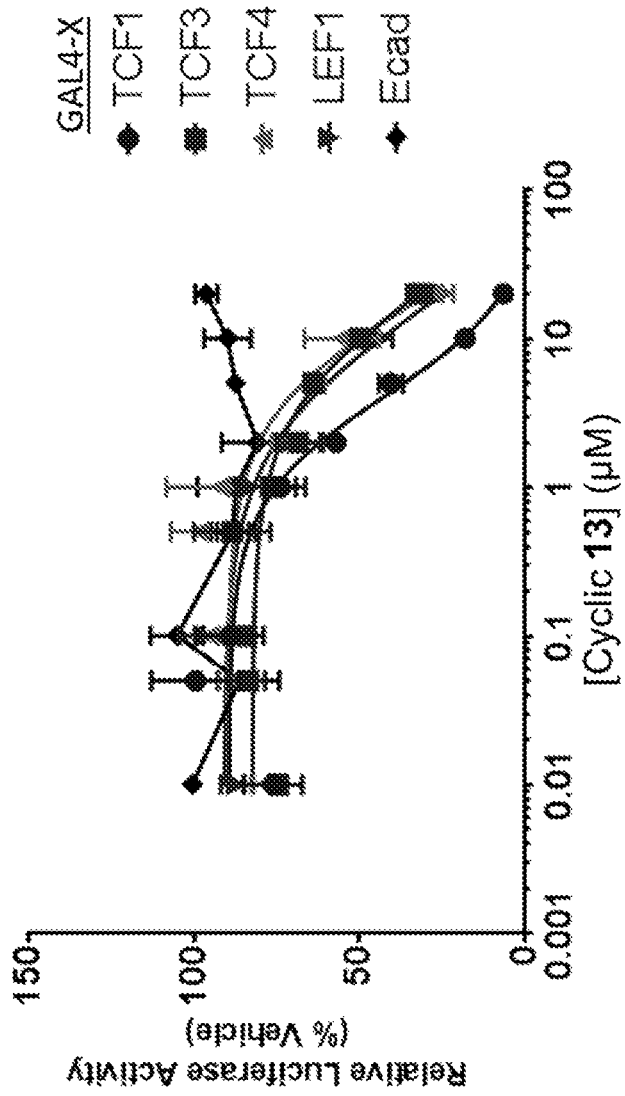
FIG. 16 shows cyclic 13 inhibits TCF family interaction but not E-cadherin with β-catenin.
Figure 17:
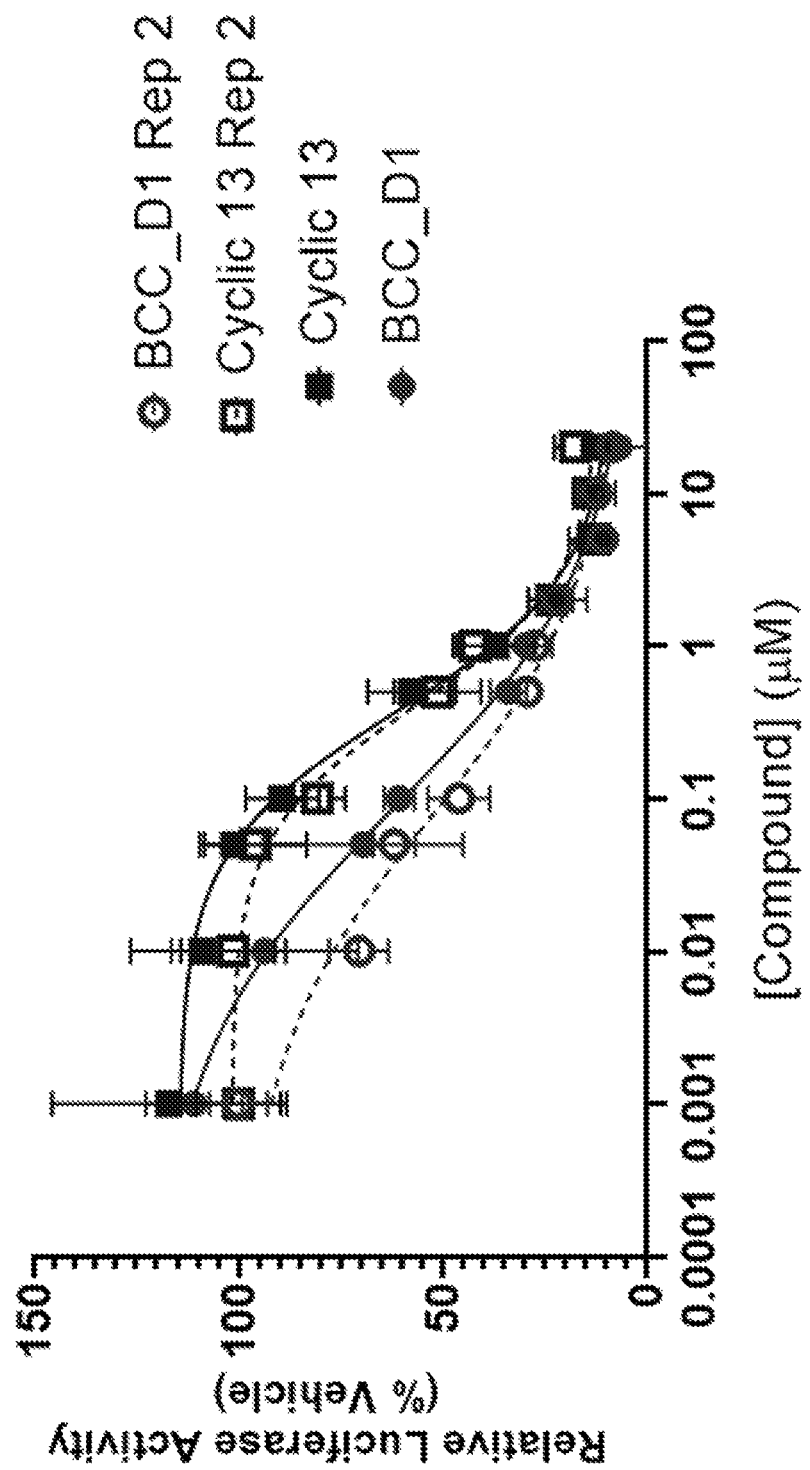
FIG. 17 shows the effect of cyclic 13 compared to the covalent β-catenin binder on Wnt/luciferase reporter gene activity.

Rescue of eye development in Wnt-activated zebrafish embryos by the hit oligomer macrocycle—To evaluate the efficacy of 13 in vivo, a zebrafish model was utilized. The relevance of the model for our studies is that zebrafish embryos with Wnt activating mutations in the AXIN gene, a component of the β-catenin destruction complex, fail to develop eyes or a forebrain. The phenotype can be recapitulated by treatment with an inhibitor (termed BIO) for another β-catenin destruction complex member, GSK3, in embryos at 6 hours post-fertilization (hpf). It would then be anticipated that 13 inhibits the chemically over-activated Wnt signal, and potentially rescue eye development. To test this compound BIO was added to zebrafish embryos at 6 hpf with and without 13 as described in FIG. 10A. Indeed, 13 inhibited Wnt signaling, as anticipated, as only one of the eight fish treated with GSK3 inhibitor BIO alone developed eyes, while all the fish treated with both BIO and 13 developed eyes (FIG. 10B-D). This result was reproduced in 3 additional independent experiments each showing that 0/8 BIO treated fish developed eyes while 8/8 BIO plus 13 treated fish developed eyes.

Discussion—The Wnt pathway remains a tantalizing but elusive target for drug discovery. Chemical inhibition of Wnt signaling has been achieved through multiple strategies. For example, Wnt secretion and function necessitates the post-translational addition of a palmitoyl group, catalyzed by the acyltransferase porcupine. Enzymatic inhibitors of porcupine have been developed and shown to inhibit the secretion of Wnts. In addition, antibodies against frizzled receptors have also been developed to inhibit Wnt signaling at the cell surface. Both of these strategies have therapeutic potential for tumors bearing mutations in R-spondin or the ubiquitin ligases ZNRF3 and RNF43 which cause amplification of Wnt signals. Clinical trials for such Wnt inhibitory agents have been initiated. Nevertheless, the majority of activating Wnt mutations occur in the APC gene or the phosphorylation domain of β-catenin, downstream of both porcupine and frizzled. Thus, it is desirable to identify inhibitors downstream of these mutations. Multiple interactions have been described between β-catenin and components of the Wnt "enhancesome" on promotors of Wnt target genes. The central interaction between β-catenin and TCF is critical to its Wnt activation and represents an attractive target for the general inhibition of canonical Wnt signaling.

How computational tools can facilitate the design of oligomers that bind to β-catenin and disrupt its interaction with TCF was demonstrated. Peptoid-peptide macrocycles designed to fold into structures complementary to a region on the β-catenin surface that interacts with TCF were evaluated. It was demonstrated that an oligomeric macrocycle exhibits potent antiproliferative effects on prostate cancer cell lines in both 2D and 3D models. In vivo efficacy of this hit compound (13) is established in a zebrafish model of Wnt signaling. The hypothesis that conformational ordering of the macrocyclic oligomer enforces steric and chemical complimentarity for the β-catenin surface is strongly supported by comparisons to a linear analog, which exhibits markedly diminished activities in vitro and in vivo.

Figure 5:
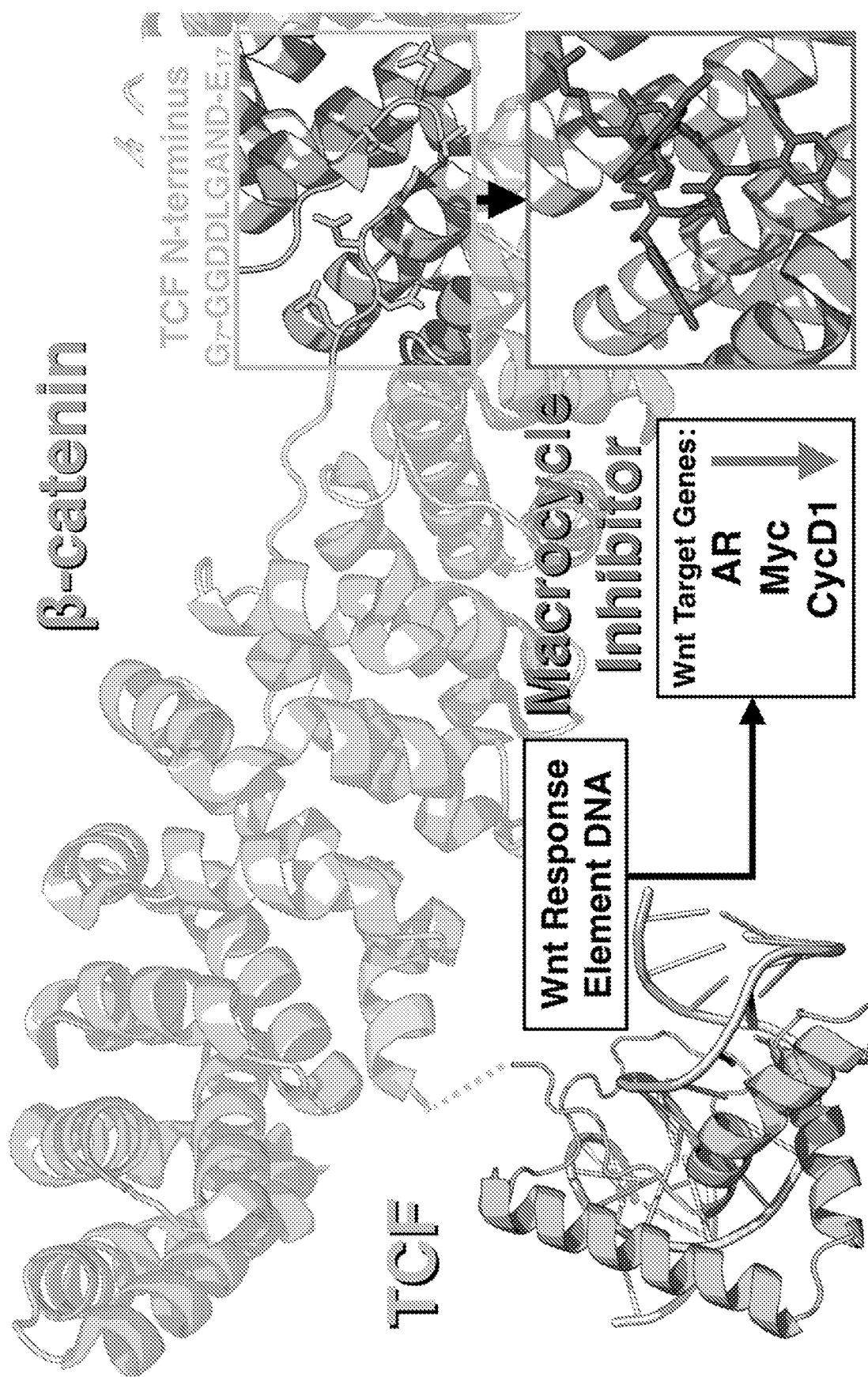
FIG. 5 shows proposed mechanism by which designed macrocycles inhibit the interaction of the N-terminal region of TCF and β-catenin resulting in a downregulation of AR (Androgen Receptor), Myc, and CycD1 (Cyclin-D1).

FIG. 5 depicts a proposed mechanism whereby the oligomer macrocycle inhibits canonical Wnt target gene expression via inhibiting the interaction between β-catenin and TCF. It was also observe that decreased AR pathway target gene expression, which could result either from direct inhibition of the β-catenin: AR interaction or indirectly through the decrease in AR gene transcript levels upon Wnt signal inhibition. It remains to be shown which pathway when inhibited, Wnt or AR, plays a critical role in the proliferation inhibition phenotype. There may be a synergistic effect of inhibiting both pathways concurrently.

The β-catenin:TCF protein-protein interaction has been targeted previously. However, there does not appear to be rapid clinical implementation of this pharmacological approach. Future testing with 13 in mouse xenograft models of prostate cancer will be important to determine its therapeutic potential, as demonstrated for other bioactive peptoid oligomers. The ability to introduce a broad range of alternative oligomer side chains should facilitate further improvements of activity along with enhanced pharmacokinetic and pharmacodynamic properties towards the identification of an optimized lead compound. In addition to promising activity versus prostate cancer, macrocycles targeting β-catenin:TCF could also be of therapeutic benefit in other forms of cancer for which Wnt signaling is similarly pro-tumorigenic, such as colon and breast cancers.

Materials and Methods

Synthesis of Compounds 1-13: 2-chlorotrityl resin (Anaspec) was incubated with Fmoc-D-Alanine (Sigma) for 1.5 hours followed by washing 5× with DMF. Deprotection was carried out with 20% piperidine in DMF. Peptoid residues were then added with iterative steps of 1.2 M bromoacetic acid+DIC for 20 minutes and 1 M amine for 1 hour. Compound 13 used the following amines: S-(−)-4-methoxy-α-methyl-benzyl-amine (Sigma), 3-isopropoxy-propyl-amine (Sigma), 3,5-dimethoxy-aniline (Sigma, overnight incubation), and 2-phenoxy-phenyl-ethyl-amine (Sigma). The resin was cleaved with 8:1:1 DCM:Acetic Acid:HFIP for 1 hour. The DCM was removed via rotary evaporation and the remaining solid was dissolved in 50:50 water:ACN and lyophilized overnight. Reverse phase HPLC was used to purify the linear product. Cyclization was carried out using 25 mg of linear compound with 5× Pybop and 10×DIEA in dry DCM with less than 1 mg/ml compound overnight under argon. The DCM was removed via rotary evaporation and the remaining solid was dissolved in 50:50 water: ACN and lyophilized overnight. The final product was purified to >95% by reverse phase HPLC and verified by electrospray ionization mass spectrometry (Agilent LCMSD Trap XCT).

Cell Culture LNCaP-abl and LNCaP-95 cells were cultured in indicator free RPMI 1640 media (Life) supplemented with 10% charcoal stripped FBS, 1% penn/strep, and 1% L-Glutamine. HEK-293 Cells were cultured in DMEM media (Life) supplemented with 10% FBS and 1% penn/strep. Luciferase assays were conducted using stably transfected TOP-flash and 3×ARE LNCaP-abl cell lines. For the Wnt pathway, TOP-Flash LNCaP-abl cells were treated with siAPC for 24 hours followed by 24 hours treatment with compound. For the AR-pathway, 3×ARE LNCaP-abl cells were treated for 48 hours with compound, with the addition of R1881 for the final 8 hours. Both were measured using the ONE-Glo detection kit (Promega) and reported data is standardized to the cell-titer control values. Co-immunoprecipitation was carried out using HEK293 cells transfected with either myc-TCF (addgene #32738) or myc-TCF dominant negative (addgene #32739) followed by 48 hours of treatment with compound. Cells were lysed using trition lysis buffer and 1 mg total protein was incubated overnight at 4 C with 40 μl anti-cMyc magnetic beads (Thermo). The beads were washed 3× with lysis buffer then boiled in 2× sample loading dye. SDS-PAGE and western blotting were performed using anti-myc (CST 2276) and anti-β-catenin (CST 8480). RT-qPCR was performed using RNA isolated with the RNEasy kit (Qiagen) from LNCaP-abl and LNCaP-95 cells after 24 hour treatment with 10 μM compound. The Verso cDNA synthesis kit (Thermo) with 1 μg total RNA was used, and qPCR data was collected using Fast SYBR Green Master Mix on a QuantiStudio 6 Flex (Life Technologies). 2D proliferation assays were conducted using 384 well plates seeded with 2000 cells/well LNCaP-abl or LNCaP-95 cells. After 5 days of treatment the cell viability was measured with the CellTiter-Fluor Cell Viability Assay (Promega) and data is reported standardized to DMSO control.

Recombinant Proteins and ELISA The ELISA was conducted using recombinant GST-tagged catenin binding domain (CBD) of TCF4 and $His_6$-β-catenin armadillo domain. Both proteins were expressed in BL21 DL3 (NEB) bacteria grown to OD600 0.6 and induced with 0.5 mM IPTG (Sigma) for β-catenin and 0.1 mM IPTG for TCF. The cells were then shaken for 8 hours at 30 C. Proteins were incubated overnight with Ni-NTA or glutathione affixed resin (Thermo), washed with TBS, and eluted using 250 mM imidazole or 20 mM glutathione in 20 mM Tris-HCL pH8.0 and 200 mM NaCl. The imidazole or glutathione were removed by dialysis into a buffer containing 20 mM Tris-HCL pH 8.0, 200 mM NaCl, and 10% glycerol. The ELISA was initiated with adsorption of 5 μg/ml GST-TCF CBD into a 96 well Nunc Maxisorp plate (Fisher) overnight at 4 C. BSA was adsorbed to control wells. The wells were washed, blocked with 5% milk for 1 hour, washed, incubated with 5 nM $His_6$-β-catenin with varying concentrations of compound in washing buffer for 1 hour, washed, incubated with anti-HIS (Thermo MA1-135) diluted 1:10000 in blocking buffer for 1 hour, washed, incubated with anti-mouse-HRP (Santa Cruz) diluted 1:15000 in blocked buffer for 1 hour, washed, and then developed using 1-Step Ultra TMB-ELISA (Thermo).

Spheroid 3D Cell Culture LNCaP-abl cells were seeded into 384 well ultra-low attachment plates (Corning), 1000 cells/well. Varying concentrations of compound were added either on the same day as seeding or on day 5. Media was changed every 3-4 days using a Biotek automated media exchanger. Images were taken using an ArraySca VTI (Thermo) on days 5, 9, 13, 16, 20, and 22. A final viability measurement was taken on day 22 using PrestoBlue reagent (Thermo).

Zebrafish Experiments The zebrafish phenotypic assay was conducted using wildtype zebrafish embryos seeded into a 96 well round bottom plate in 50 μl of blue zebrafish embryo media. At 50% epiboly, roughly 5.5 hours post fertilization, 50 ul of 30 μM cyclic peptoid compound was added. About 30 minutes later at shield stage, 50 μl 6 nM (3×) BIO was added. The embryos were then visualized for the presence of eyes and imaged at 30 hours post fertilization.

From the foregoing description, various modifications and changes in the compositions and methods of this disclosure will occur to those skilled in the art. All such modifications coming within the scope of the appended claims are intended to be included therein.

At least some of the chemical names of compounds of the disclosure as given and set forth in this application, may have been generated on an automated basis by use of a commercially available chemical naming software program, and have not been independently verified. Representative programs performing this function include the Lexichem naming tool sold by Open Eye Software, Inc., the Autonom Software tool sold by MDL, Inc. and the structure-to-name tool in the ChemDraw software sold by PerkinElmer, Inc. In the instance where the indicated chemical name and the depicted structure differ, the depicted structure will control.

Chemical structures shown herein were prepared using either ChemDraw® or ISIS®/DRAW. Any open valency appearing on a carbon, oxygen or nitrogen atom in the structures herein indicates the presence of a hydrogen atom. Where a chiral center exists in a structure but no specific stereochemistry is shown for the chiral center, both enantiomers associated with the chiral structure are encompassed by the structure.

The invention claimed is:

1. A peptoid-peptide macrocycle having the following structure:

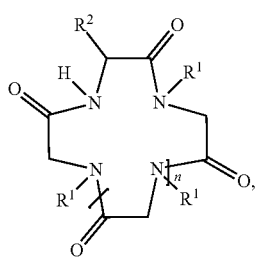

I wherein R² is an amino acid sidechain of glycine, D-alanine, D-valine, D-leucine, D-isoleucine, D-tyrosine, D-proline, D-serine, D-glutamic acid, D-tryptophan, D-phenylalanine, D-methionine, D-arginine, D-histidine, D-glutamine, D-lysine, D-aspartic acid, D-threonine, D-cysteine, D-asparagine, L-alanine, L-valine, L-leucine, L-isoleucine, L-tyrosine, L-proline, L-serine, L-glutamic acid, L-tryptophan, L-phenylalanine, L-methionine, L-arginine, L-histidine, L-glutamine, L-lysine, L-aspartic acid, L-threonine, L-cysteine, or L-asparagine; each $R^1$ is independently chosen from methoxy-ethyl

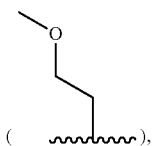

4-methoxy-phenyl-ethyl

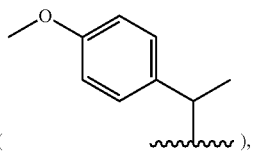

3,5-dimethoxy-phenyl

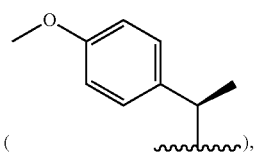 [SMILES: *[C@H](C)c1ccc(OC)cc1]

(S)-4-methoxy-phenyl-ethyl (S)-4-fluoro-phenyl-ethyl

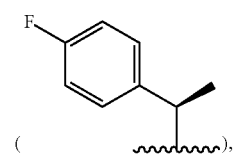 [SMILES: *[C@H](C)c1ccc(F)cc1]

2-phenoxy-ethyl
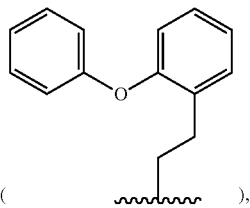 [SMILES: *CCc1ccccc1Oc1ccccc1]
(  ),
isopropoxy-propyl
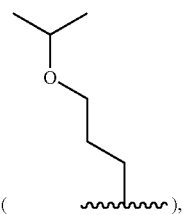
(  ),
methoxy-propyl
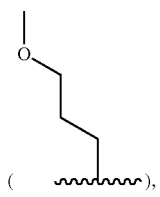 [SMILES: *CCCOC]
(  ),
and 3,4-dimethoxyphenyl
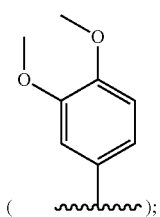
(  );
and the subscript n is an integer from 0 to 15.
2. The peptoid-peptide macrocycle of claim 1, wherein n is 1, 2, or 3.
3. The peptoid-peptide macrocycle of claim 1, wherein the peptoid-peptide macrocycle is:
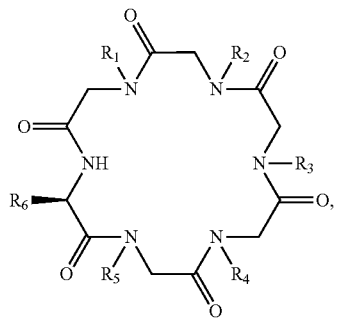
wherein
$R_1$ is
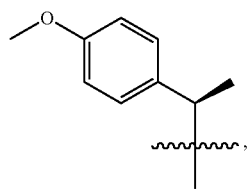 [SMILES: *[C@H](C)c1ccc(OC)cc1]
$R_2$ is
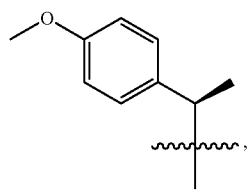
$R_3$ is
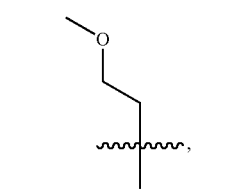 [SMILES: *CCOC]
$R_4$ is
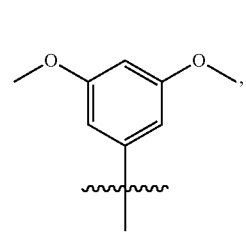

151
$R_5$ is
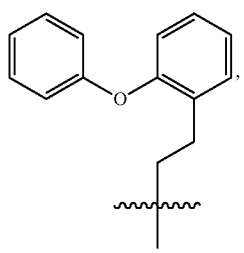 [SMILES: *CCc1ccccc1Oc1ccccc1],
and $R_6$ is
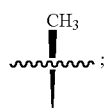;
$R_1$ is
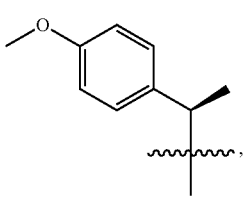 [SMILES: *[C@H](C)c1ccc(OC)cc1],
$R_2$ is
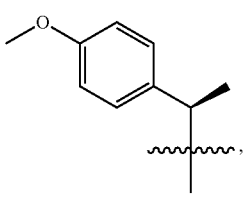 [SMILES: *[C@H](C)c1ccc(OC)cc1],
$R_3$ is
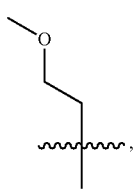 [SMILES: *CCOC],
$R_4$ is
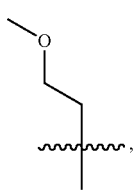 [SMILES: *CCOC],
152
$R_5$ is
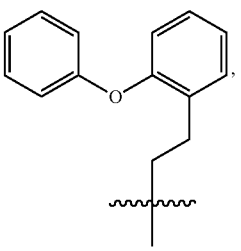,
and $R_6$ is
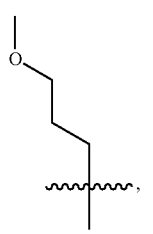;
$R_1$ is
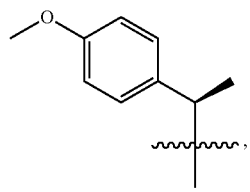,
$R_2$ is
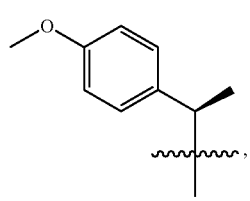 [SMILES: *[C@H](C)c1ccc(OC)cc1],
$R_3$ is

153
R₄ is
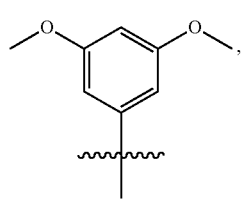
R₅ is
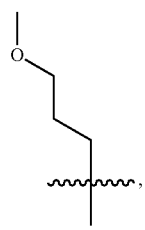
and R₆ is
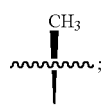
R₁ is
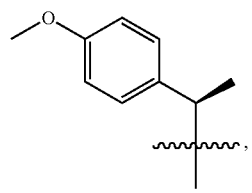 [SMILES: *[C@H](C)c1ccc(OC)cc1]
R₂ is
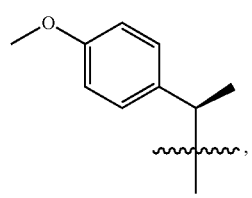 [SMILES: *[C@H](C)c1ccc(OC)cc1]
154
R₃ is
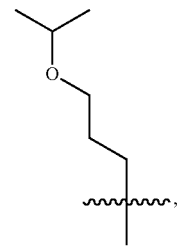 [SMILES: *CCCOC(C)C]
R₄ is
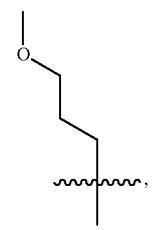
R₅ is
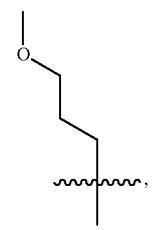
and R₆ is
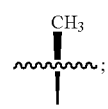
R₁ is
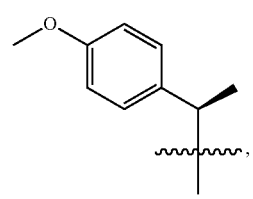 [SMILES: *[C@H](C)c1ccc(OC)cc1]
R₂ is
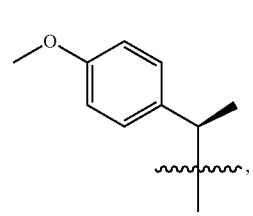 [SMILES: *[C@H](C)c1ccc(OC)cc1]

155
R₃ is
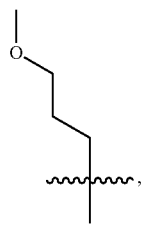
R₄ is
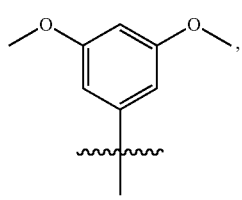
R₅ is
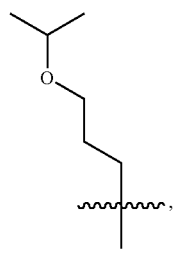 [SMILES: *CCCOC(C)C]
and R₆ is
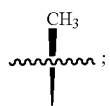
R₁ is
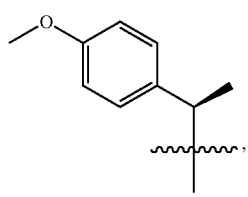 [SMILES: *[C@H](C)c1ccc(OC)cc1]
156
R₂ is
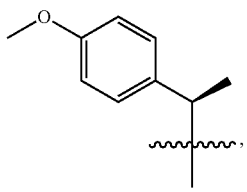 [SMILES: *[C@H](C)c1ccc(OC)cc1]
R₃ is
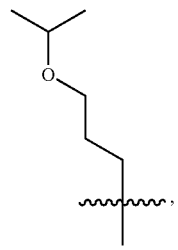 [SMILES: *CCCOC(C)C]
R₄ is
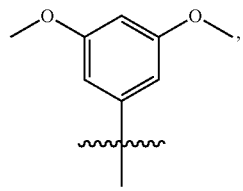
R₅ is
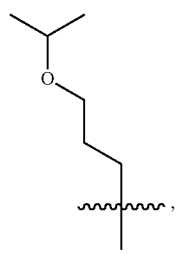 [SMILES: *CCCOC(C)C]
and R₆ is
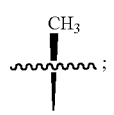

or

R₁ is

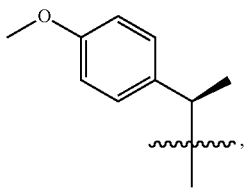 [SMILES: *[C@H](C)c1ccc(OC)cc1]

R₂ is

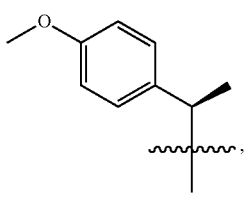 [SMILES: *[C@H](C)c1ccc(OC)cc1]

R₃ is

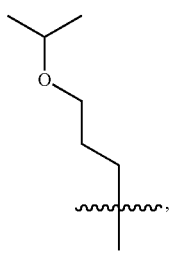 [SMILES: *CCCOC(C)C]

R₄ is

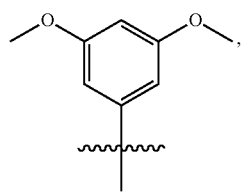

R₅ is

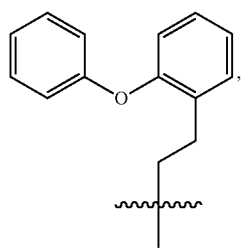 [SMILES: *CCc1ccccc1Oc1ccccc1]

and R₆ is

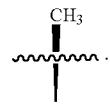

4. A composition comprising the peptoid-peptide macrocycle of claim 1 and a pharmaceutically acceptable carrier.

5. The composition of claim 4, wherein the pharmaceutically acceptable carrier is a parenteral, oral, or topical carrier.

6. The peptoid-peptide macrocycle of claim 3, wherein the peptoid-peptide macrocycle is:

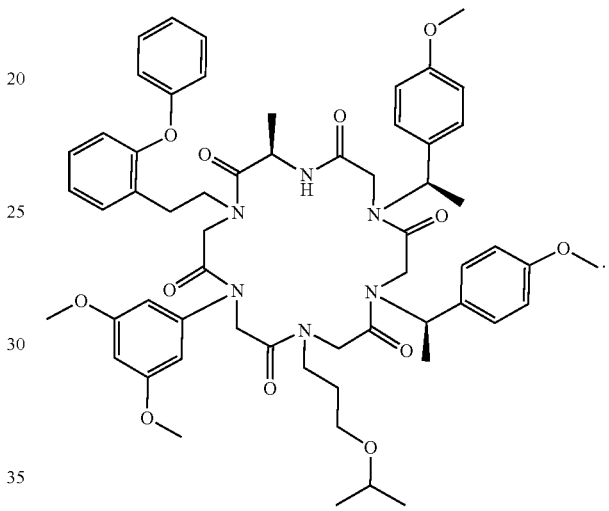

7. A peptoid-peptide macrocycle having the following structure:

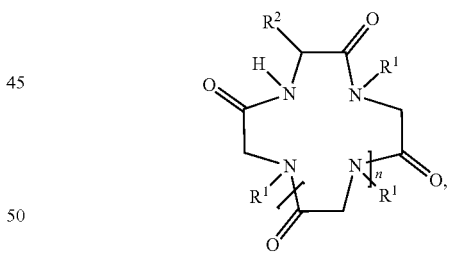

I wherein $R^2$ is an amino acid sidechain of D-alanine, D-valine, D-leucine, D-isoleucine, D-tyrosine, D-proline, D-serine, D-glutamic acid, D-tryptophan, D-phenylalanine, D-methionine, D-arginine, D-histidine, D-glutamine, D-lysine, D-aspartic acid, D-threonine, D-cysteine, D-asparagine, L-alanine, L-valine, L-leucine, L-isoleucine, L-tyrosine, L-proline, L-serine, L-glutamic acid, L-tryptophan, L-phenylalanine, L-methionine, L-arginine, L-histidine, L-glutamine, L-lysine, L-aspartic acid, L-threonine, L-cysteine, or L-asparagine; each $R^1$ is independently substituted or unsubstituted alkyl, substituted or unsubstituted cycloalkyl, substituted or unsubstituted heterocycloalkyl, substituted or unsubstituted aryl, or substituted or unsubstituted heteroaryl; and the subscript n is 0 or an integer from 2 to 15, wherein $R^1$ is not methyl.

8. The peptoid-peptide macrocycle of claim 7, wherein $R^2$ is methyl.

9. The peptoid-peptide macrocycle of claim 7, wherein n is 2 or 3.

* * * * *

SEQUENCE LISTING

<160> NUMBER OF SEQ ID NOS: 14

<210> SEQ ID NO 1
<211> LENGTH: 25
<212> TYPE: PRT
<213> ORGANISM: Xenopus laevis

```
<400> SEQUENCE: 1

Met Pro Gln Leu Asn Ser Gly Gly Gly Asp Glu Leu Gly Ala Asn Asp
1               5                   10                  15

Glu Leu Ile Arg Phe Lys Asp Glu Gly
            20                  25

<210> SEQ ID NO 2
<211> LENGTH: 14
<212> TYPE: PRT
<213> ORGANISM: Xenopus laevis

<400> SEQUENCE: 2

Glu Gln Glu Glu Lys Ser Pro Gly Glu Gly Ser Ala Glu Gly
1               5                   10

<210> SEQ ID NO 3
<211> LENGTH: 15
<212> TYPE: PRT
<213> ORGANISM: Xenopus laevis

<400> SEQUENCE: 3

Asp Leu Ala Asp Val Lys Ser Ser Leu Val Asn Glu Ser Glu Asn
1               5                   10                  15

<210> SEQ ID NO 4
<211> LENGTH: 25
<212> TYPE: PRT
<213> ORGANISM: Homo sapiens

<400> SEQUENCE: 4

Met Pro Gln Leu Asn Gly Gly Gly Gly Asp Asp Leu Gly Ala Asn Asp
1               5                   10                  15

Glu Leu Ile Ser Phe Lys Asp Glu Gly
            20                  25

<210> SEQ ID NO 5
<211> LENGTH: 14
<212> TYPE: PRT
<213> ORGANISM: Homo sapiens

<400> SEQUENCE: 5

Glu Gln Glu Glu Lys Ser Ser Glu Asn Ser Ser Ala Glu Arg
1               5                   10

<210> SEQ ID NO 6
<211> LENGTH: 15
<212> TYPE: PRT
<213> ORGANISM: Homo sapiens

<400> SEQUENCE: 6

Asp Leu Ala Asp Val Lys Ser Ser Leu Val Asn Glu Ser Glu Thr
1               5                   10                  15

<210> SEQ ID NO 7
<211> LENGTH: 58
<212> TYPE: PRT
<213> ORGANISM: Homo sapiens

<400> SEQUENCE: 7

Met Pro Gln Leu Gly Gly Gly Gly Gly Gly Gly Gly Gly Ser Gly
1               5                   10                  15

Gly Gly Gly Gly Ser Ser Ala Gly Ala Ala Gly Gly Asp Asp Leu
            20                  25                  30
```

Gly Ala Asn Asp Glu Leu Ile Pro Phe Gln Asp Glu Gly Gly Glu Glu
        35                  40                  45

Gln Glu Pro Ser Ser Asp Ser Ala Ser Ala
    50                  55

<210> SEQ ID NO 8
<211> LENGTH: 15
<212> TYPE: PRT
<213> ORGANISM: Homo sapiens

<400> SEQUENCE: 8

Asp Leu Asp Glu Val Lys Ser Ser Leu Val Asn Glu Ser Glu Asn
1               5                   10                  15

<210> SEQ ID NO 9
<211> LENGTH: 10
<212> TYPE: PRT
<213> ORGANISM: Homo sapiens

<400> SEQUENCE: 9

Met Pro Gln Leu Asp Ser Gly Gly Gly Gly
1               5                   10

<210> SEQ ID NO 10
<211> LENGTH: 36
<212> TYPE: PRT
<213> ORGANISM: Homo sapiens

<400> SEQUENCE: 10

Ala Gly Gly Gly Asp Asp Leu Gly Ala Pro Asp Glu Leu Leu Ala Phe
1               5                   10                  15

Gln Asp Glu Gly Glu Glu Gln Asp Asp Lys Ser Arg Asp Ser Ala Ala
            20                  25                  30

Gly Pro Glu Arg
        35

<210> SEQ ID NO 11
<211> LENGTH: 15
<212> TYPE: PRT
<213> ORGANISM: Homo sapiens

<400> SEQUENCE: 11

Asp Leu Ala Glu Leu Lys Ser Ser Leu Val Asn Glu Ser Glu Gly
1               5                   10                  15

<210> SEQ ID NO 12
<211> LENGTH: 11
<212> TYPE: PRT
<213> ORGANISM: Homo sapiens

<400> SEQUENCE: 12

Met Pro Gln Leu Ser Gly Gly Gly Gly Gly
1               5                   10

<210> SEQ ID NO 13
<211> LENGTH: 52
<212> TYPE: PRT
<213> ORGANISM: Homo sapiens

```
<400> SEQUENCE: 13

Gly Gly Asp Pro Glu Leu Cys Ala Thr Asp Glu Met Ile Pro Phe Lys
1               5                   10                  15

Asp Glu Gly Asp Pro Gln Lys Glu Lys Ile Phe Ala Glu Ile Ser His
                20                  25                  30

Pro Glu Glu Gly Asp Leu Ala Asp Ile Lys Ser Ser Leu Val Asn
        35                  40                  45

Glu Ser Glu Ile
    50

<210> SEQ ID NO 14
<211> LENGTH: 33
<212> TYPE: PRT
<213> ORGANISM: Homo sapiens

<400> SEQUENCE: 14

Gly Gly Gly Gly Gly Gly Gly Gly Gly Gly Gly Gly Ala Asn Asp
1               5                   10                  15

Glu Glu Glu Glu Glu Glu Glu Glu Glu Glu Glu Glu Glu Glu Glu
                20                  25                  30

Glu
```